United States Patent
Joung et al.

(10) Patent No.: US 9,822,407 B2
(45) Date of Patent: Nov. 21, 2017

(54) GENOMEWIDE UNBIASED IDENTIFICATION OF DSBS EVALUATED BY SEQUENCING (GUIDE-SEQ)

(71) Applicant: The General Hospital Corporation, Boston, MA (US)

(72) Inventors: J. Keith Joung, Winchester, MA (US); Shengdar Tsai, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/192,753

(22) Filed: Jun. 24, 2016

(65) Prior Publication Data

US 2016/0304950 A1 Oct. 20, 2016

Related U.S. Application Data

(63) Continuation of application No. PCT/US2015/037269, filed on Jun. 23, 2015.

(60) Provisional application No. 62/015,911, filed on Jun. 23, 2014, provisional application No. 62/077,844, filed on Nov. 10, 2014, provisional application No. 62/078,923, filed on Nov. 12, 2014, provisional application No. 62/088,223, filed on Dec. 5, 2014.

(51) Int. Cl.
  *C12Q 1/68* (2006.01)
(52) U.S. Cl.
  CPC ......... *C12Q 1/6869* (2013.01); *C12Q 1/6855* (2013.01)
(58) Field of Classification Search
  None
  See application file for complete search history.

(56) References Cited

U.S. PATENT DOCUMENTS

| | | |
|---|---|---|
| 7,803,550 B2 | 9/2010 | Makarov et al. |
| 8,071,312 B2 | 12/2011 | Makarov et al. |
| 8,399,199 B2 | 3/2013 | Makarov et al. |
| 8,420,319 B2 | 4/2013 | Mikawa |
| 8,728,737 B2 | 5/2014 | Makarov et al. |
| 2006/0292611 A1 | 12/2006 | Berka et al. |
| 2009/0082295 A1 | 3/2009 | Jungnelius et al. |
| 2010/0317722 A1 | 12/2010 | Lavon |
| 2011/0060493 A1 | 3/2011 | Miura et al. |
| 2011/0287545 A1* | 11/2011 | Cost ............ C12N 9/22 435/440 |
| 2013/0137605 A1 | 5/2013 | Shendure et al. |
| 2013/0143204 A1* | 6/2013 | Von Kalle ........ C12Q 1/6827 435/5 |
| 2013/0303461 A1 | 11/2013 | Iafrate et al. |
| 2013/0309668 A1 | 11/2013 | Makarov et al. |
| 2014/0024542 A1* | 1/2014 | Richards ........ C12Q 1/6806 506/9 |
| 2014/0295557 A1 | 10/2014 | Joung et al. |

FOREIGN PATENT DOCUMENTS

| | | | |
|---|---|---|---|
| WO | WO/2012/065143 | 5/2012 | |
| WO | WO 2013078470 A2 * | 5/2013 | ......... C12N 15/1093 |
| WO | WO 2014/093701 | 6/2014 | |
| WO | WO 2015/200378 | 12/2015 | |

OTHER PUBLICATIONS

Berg, JM, Tymoczko, JL, and Stryer, L. Section 7.1 Homologs Are Descended from a Common Ancestor. Biochemistry. 5th edition. New York: W H Freeman, 2002, printed as p. 1 of 1 from https://www.ncbi.nlm.nih.gov/books/NBK22355.*
PCR Methods-Top Ten Strategies, https://www.thermofisher.com/us/en/home/life-science/cloning/cloning-learning-center/invitrogen-school-of-molecular-biology/pcr-education/per-reagents-enzymes/pcr-methods.html, 2017, printed on Feb. 1, 2017 as pp. 1/10-10-10.*
Mullis et al. Specific synthesis of DNA in vitro via a polymerase-catalyzed chain reaction. Methods in Enzymology, vol. 155, pp. 335-350, 1987.*
Tsai et al. Nature Biotechnology, vol. 33, No. 2, pp. 187-197, 2015, and Supplementary Information pp. 1-40, all available online Dec. 16, 2014.*
Ran et al. Double nicking by RNA-guided CRISPR Cas9 for enhanced genome editing specificity. Cell, vol. 154, pp. 1380-1389, Sep. 12, 2013, including Supplemental Information pp. S1-S5.*
Bolukbasi et al., "Creating and evaluating accurate CRISPR-Cas9 scalpels for genomic surgery," Nat Meth, Jan. 2016, 13: 41-50.
Cox et al., "Therapeutic genome editing: prospects and challenges," Nat Med, 21: 121-131 (2015).
Frock et al., "Genome-wide detection of DNA double-stranded breaks induced by engineered nucleases," Nat Biotechnol, Feb. 2015, 33: 179-186.
Gori et al., "Delivery and Specificity of CRISPR-Cas9 Genome Editing Technologies for Human Gene Therapy," Hum Gene Ther, 2015, 26: 443-451.
Jiang et al., "Characterization of *Escherichia coli* Endonuclease VIII," J. Biol. Chem, 1997, 272:32230-32239.
Kim et al., "Digenome-seq: genome-wide profiling of CRISPR-Cas9 off-target effects in human cells," Nat Meth, Mar. 2015, 12: 237-243.
Kim et al., "Genome-wide target specificities of CRISPR-Cas9 nucleases revealed by multiplex Digenome-seq.," Genome Res, 2016, 26: 406-415.
Lindahl, "DNA repair enzymes," Annu. Rev. Biochem, 1982, 51:61-64.
Lindhal et al., "DNA N-glycosidases: properties of uracil-DNA glycosidase from *Escherichia coli*," J. Biol. Chem., May 1977, 252:3286-3294.
Melamede et al., "Isolation and characterization of endonuclease VIII from *Escherichia coli*," Biochemistry, Feb. 1994, 33:1255-1264.
Ochman et al., Genetic Applications of an Inverse Polymerase Chain Reaction, Genetics, Nov. 1998, 120: 621-623.
Ran et al., "In vivo genome editing using *Staphylococcus aureus* Cas9," Nature, Apr. 2015, 520, 186-191.
Tsai and Joung, "Defining and improving the genome- wide specificities of CRISPR-Cas9 nucleases," Nature, Apr. 2016, 17: 300-312.

(Continued)

*Primary Examiner* — Jennifer Dunston
(74) *Attorney, Agent, or Firm* — Fish & Richardson P.C.

(57) ABSTRACT

Unbiased, genomewide and highly sensitive methods for detecting mutations, e.g., off-target mutations, induced by engineered nucleases.

12 Claims, 55 Drawing Sheets

(56) References Cited

OTHER PUBLICATIONS

Yang et al., "Targeted and genome-wide sequencing reveal single nucleotide variations impacting specificity of Cas9 in human stem cells," Nature Communications, Nov. 2014, 5: 5507.
Cencic et al., "Protospacer Adjacent Motif (PAM)-Distal Sequences Engage CRISPR Cas9 DNA Target Cleavage," Oct. 2014, PLOS One, 9(10): e109213.
Cho et al., "Analysis of off-target effects of CRISPR/Cas-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choi & Meyerson, "Targeted genomic rearrangements using CRISPR/Cas technology," Nat Commun., Apr. 24, 2014, 5:3728, doi: 10.1038/ncomms4728.
Cong et al., "Multiplex genome engineering using CRISPR/Cas systems," Science, 2013, 339:819-823 (Author Manuscript).
Cradick et al., "CRISPR/Cas9 systems targeting beta-globin and CCR5 genes have substantial off-target activity," Nucleic Acids Res., 2013, 41(20):9584-92.
Crosetto et al, "Nucleotide-resolution DNA double-strand break mapping by next-generation sequencing," Apr. 2013, Nat Methods 10(4): 361-365.
DiCarlo et al., "Genome engineering in *Saccharomyces cerevisiae* using CRISPR-Cas systems," Nucleic Acids Res, 2013, 1-8.
Duan,et al., "Genome-wide identification of CRISPR/Cas9 off-targets in human genome," Cell Res, 2014, 24(8):1009-1012.
Fonfara et al., "Phylogeny of Cas9 determines functional exchangeability of dual-RNA and Cas9 among orthologous type II CRISPR-Cas systems," 2014, Nucleic Acids Res 42(4): 2577-2590.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat Biotechnol, Mar. 2014, 32(3): 279-284.
Gabriel et al., "An unbiased genome-wide analysis of zinc-finger nuclease specificity," Nat Biotechnol, Sep. 2011, 29(9): 816-823.
Gaj et al., "ZFN, TALEN and CRISPR/Cas-based methods for genome engineering," Trends Biotechnol, Jul. 2013, 31(7):397-405.
Ghezraoui et al., "Chromosomal translocations in human cells are generated by canonical nonhomologous end-joining," Mol Cell, Sep. 18, 2014, 55: 829-842.
Gnirke et al., "Solution hybrid selection with ultra-long oligonucleotides for massively parallel targeted sequencing," Nature Biotechnology, 2009, 27: 182-189.
Gostissa et al., "IgH class switching exploits a general property of two DNA breaks to be joined in cis over long chromosomal distances," Proc Natl Acad Sci, Feb. 18, 2014, 111(7): 2644-2649.
Guilinger et al., "Fusion of catalytically inactive Cas9 to FokI nuclease improves the specificity of genome modification," Nat Biotechnol, Jun. 2014, 32(6): 577-582.
Heigwer et al., "E-CRISP: fast CRISPR target site identification," Nat Methods, Feb. 2014, 11: 122-123.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Hwang et al., "Efficient In Vivo Genome Editing Using RNA-Guided Nucleases," Nat Biotechnol., 2013, 31:227-229 (Author Manuscript).

International Search Report and Written Opinion in International Application No. PCT/US15/37269, dated Oct. 15, 2015, 26 pages.
Jiang et al., "CRISPR-assisted editing of bacterial genomes," Nat Biotechnol, Mar. 2013, 31(3): 233-239.
Jinek et al., "A programmable dual-RNA-guided DNA endonuclease in adaptive bacterialimmunity," Science, 2012, 337:816-821.
Jinek et al., "RNA-programmed genome editing in human cells," Elife, 2013, 2:e00471, 9 pages.
Kuscu et al., "Genome-wide analysis reveals characteristics of off-target sites bound by the Cas9 endonuclease," Nat Biotechnol, Jul. 2014, 32 (7): 677-683.
Lin et al., "CRISPR/Cas9 systems have off-target activity with insertions or deletions between target DNA and guide RNA sequences," Nucleic Acids Res, 2014, 42(11): 7473-7485.
Mali et al, "CAS9 transcriptional activators for target specificity screening and paired nickases for cooperative genome engineering," Nat Biotechnol, Sep. 2013, 31(9): 833-838.
Mali et al., "RNA-guided human genome engineering via Cas9," Science, Feb. 2013, 339:823-826 (Author Manuscript).
Marx et al., "Gene editing: how to stay on-target with CRISPR," Nat Methods, 2014, 11:1021-1026.
Orlando et al., "Zinc-finger nuclease-driven targeted integration into mammalian genomes using donors with limited chromosomal homology," Nucleic Acids Res, 2010, 38(15): e152.
Osborn et al., "TALEN-based gene correction for epidermolysis bullosa," 2013, Mol Ther, 21: 1151-1159.
Pattanayak et al., "High-throughput profiling of off-target DNA cleavage reveals RNA-programmed Cas9 nuclease specificity," Nat Biotechnol., 2013, 31:839-843 (Author Manuscript).
Ran et al., "Genome engineering using the CRISPR-Cas9 system," Nat Protoc, Nov. 2013, 8(11): 2281-2308.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res, Oct. 2013, 41(19): e181.
Schmidt et al., "High-resolution insertion-site analysis by linear amplification-mediated PCR (LAM-PCR)," Nat Methods, Dec. 2007, 4(12): 1051-1057.
Shen et al., "Generation of gene-modified mice via Cas9/RNA-mediated gene targeting," Cell Res, 2013, 23:720-723.
Smith et al, "Whole-genome sequencing analysis reveals high specificity of CRISPR/Cas9 and Talen-based genome editing in human iPSCs," Cell Stem Cell, Jul. 3, 2014, 15(1):12-13.
Tsai et al., "Dimeric CRISPR RNA-guided FokI nucleases for highly specific genome editing," Nat Biotechnol, Jun. 2014, 32(6): 569-576.
Tsai et al., "What's changed with genome editing?," Jul. 2014, Cell Stem Cell, 15(1): 3-4.
Veres et al., "Low incidence of off-target mutations in individual CRISPR-Cas9 and TALEN targeted human stem cell clones detected by whole-genome sequencing," Cell Stem Cell, Jul. 3, 2014, 15: 27-30.
Wu et al., "Genome-wide binding of the CRISPR endonuclease Cas9 in mammalian cells," Nat Biotechnol. Jul. 2004; 32(7):670-6.
Zheng et al., "Anchored multiplex PCR for targeted next-generation sequencing," Nat Med, Nov. 10, 2014, 20(12): 1479-1484.
International Search Report and Written Opinion in International Application No. PCT/US16/51097, mailed on Jan. 24, 2017, 12 pages.
International Search Report and Written Opinion in International Application No. PCT/US16/54912, mailed on Jan. 24, 2017, 12 pages.

* cited by examiner

FIG. 2B

| Target | Intergenic | Exons | Introns |
|---|---|---|---|
| VEGFA site 1 | 8 | 1 | 12 |
| VEGFA site2 | 39 | 24 | 88 |
| VEGFA site3 | 19 | 6 | 34 |
| EMX1 | 9 | 1 | 5 |
| FANCF | 3 | 3 | 2 |
| RNF2 | 0 | 0 | 0 |
| HEK 293 site 1 | 6 | 1 | 2 |
| HEK 293 site 2 | 1 | 0 | 1 |
| HEK 293 site 3 | 2 | 1 | 2 |
| HEK 293 site 4 | 39 | 20 | 74 |

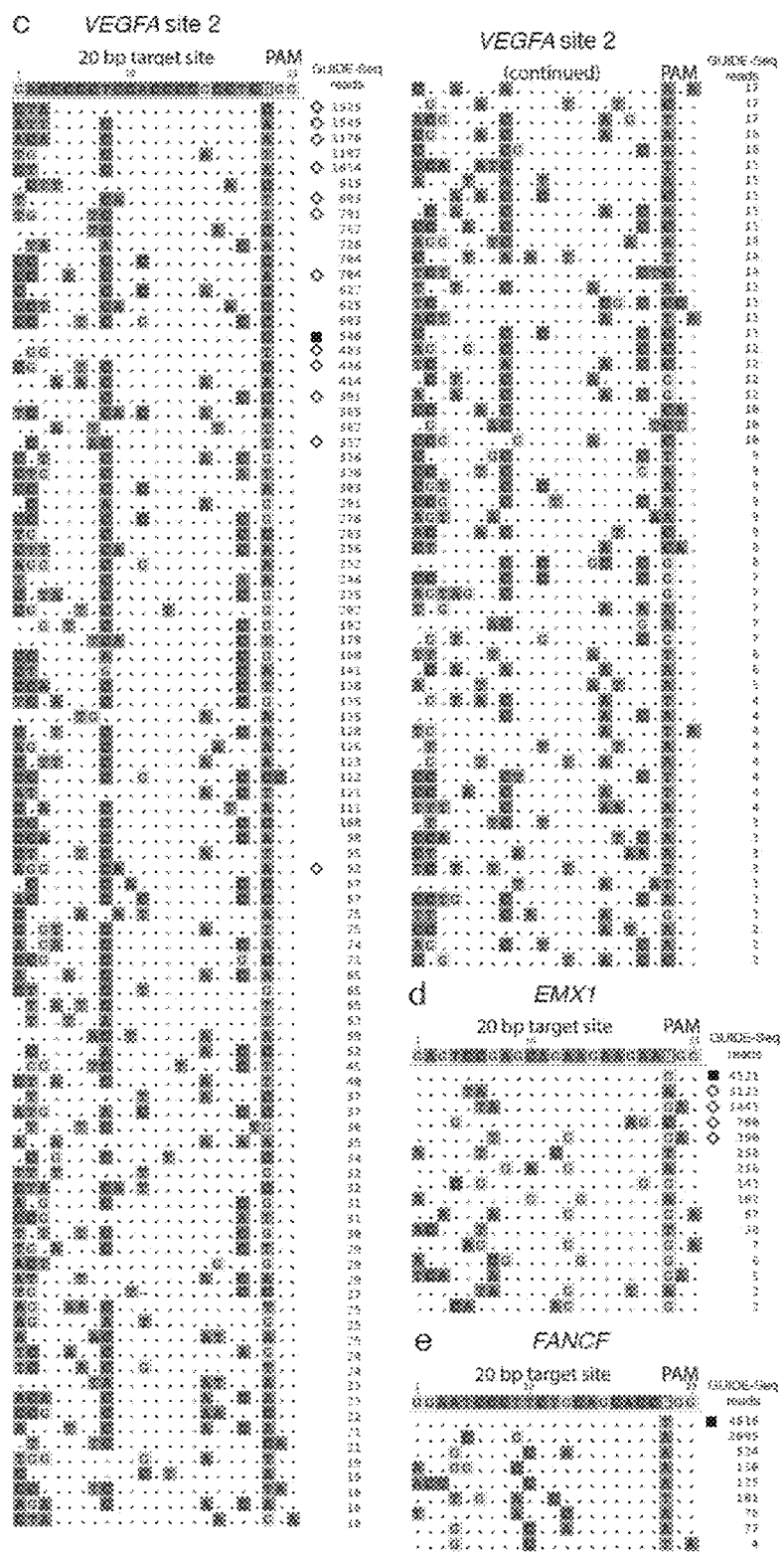
FIGs. 6C-E

FIG. 6F
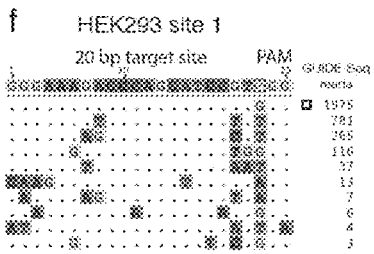
FIG. 6G
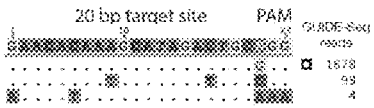
FIG. 6H
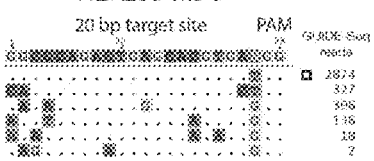
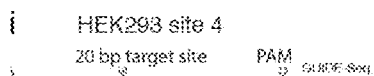
FIG. 6I
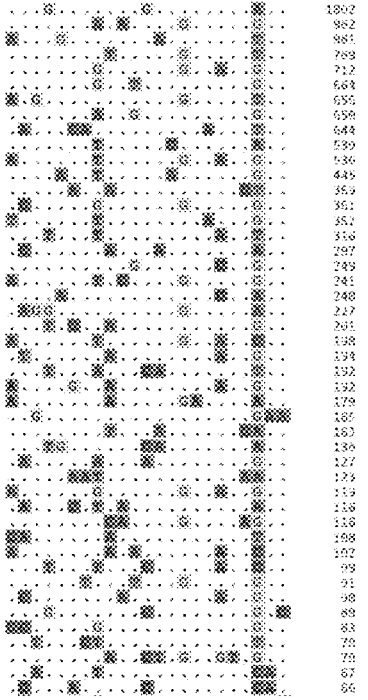
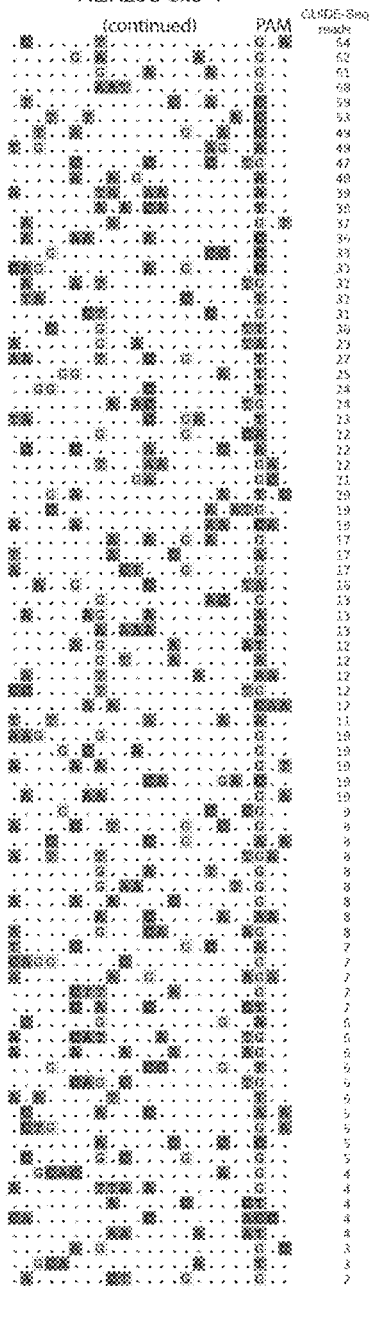
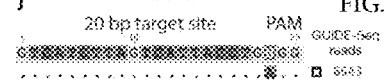
FIGs. 6F-J

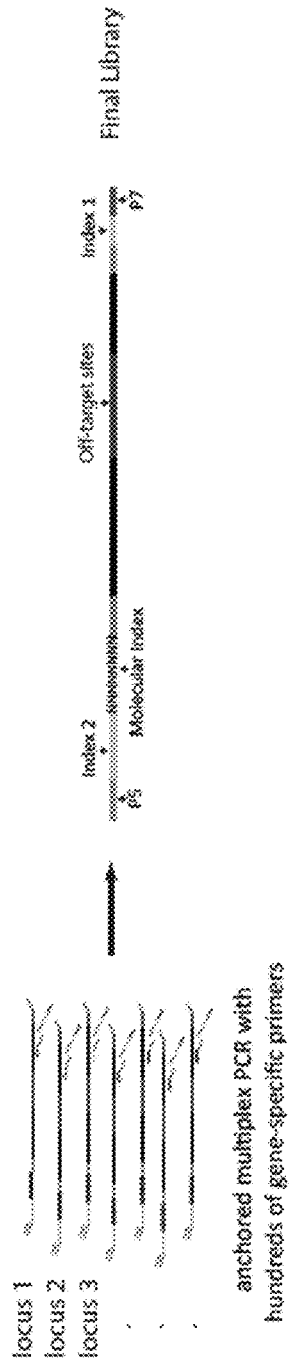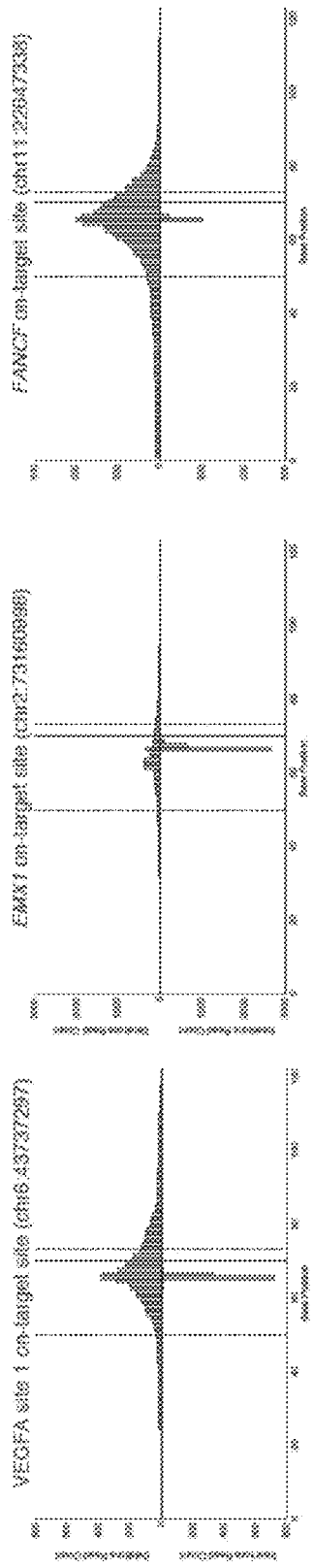
FIG. 7A

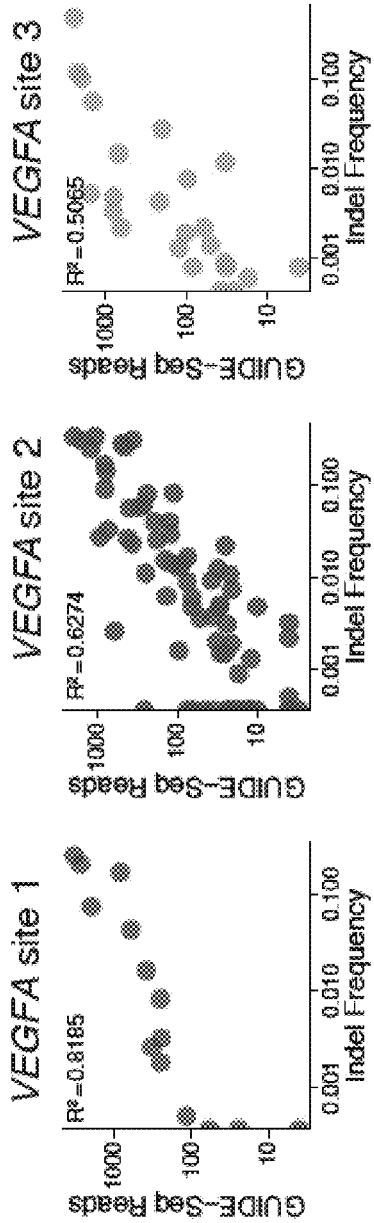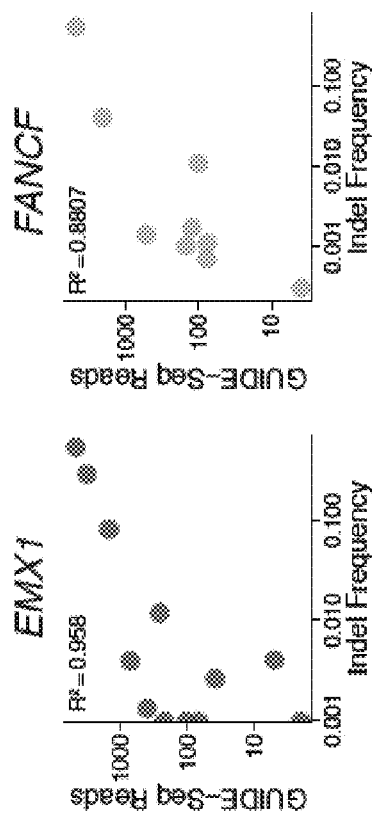

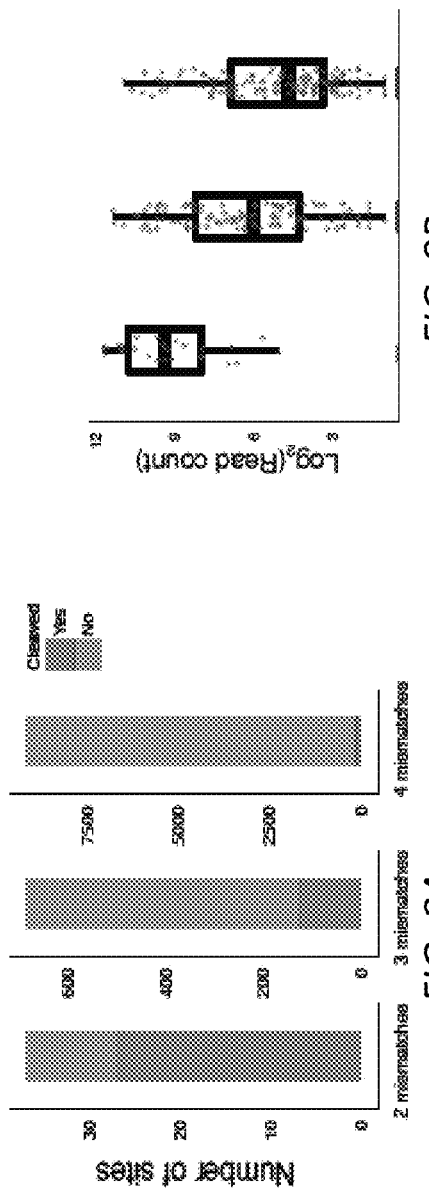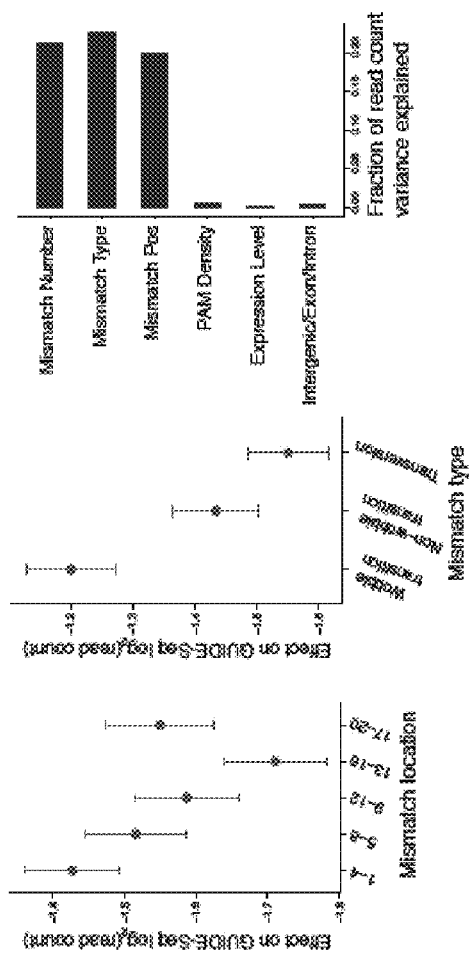

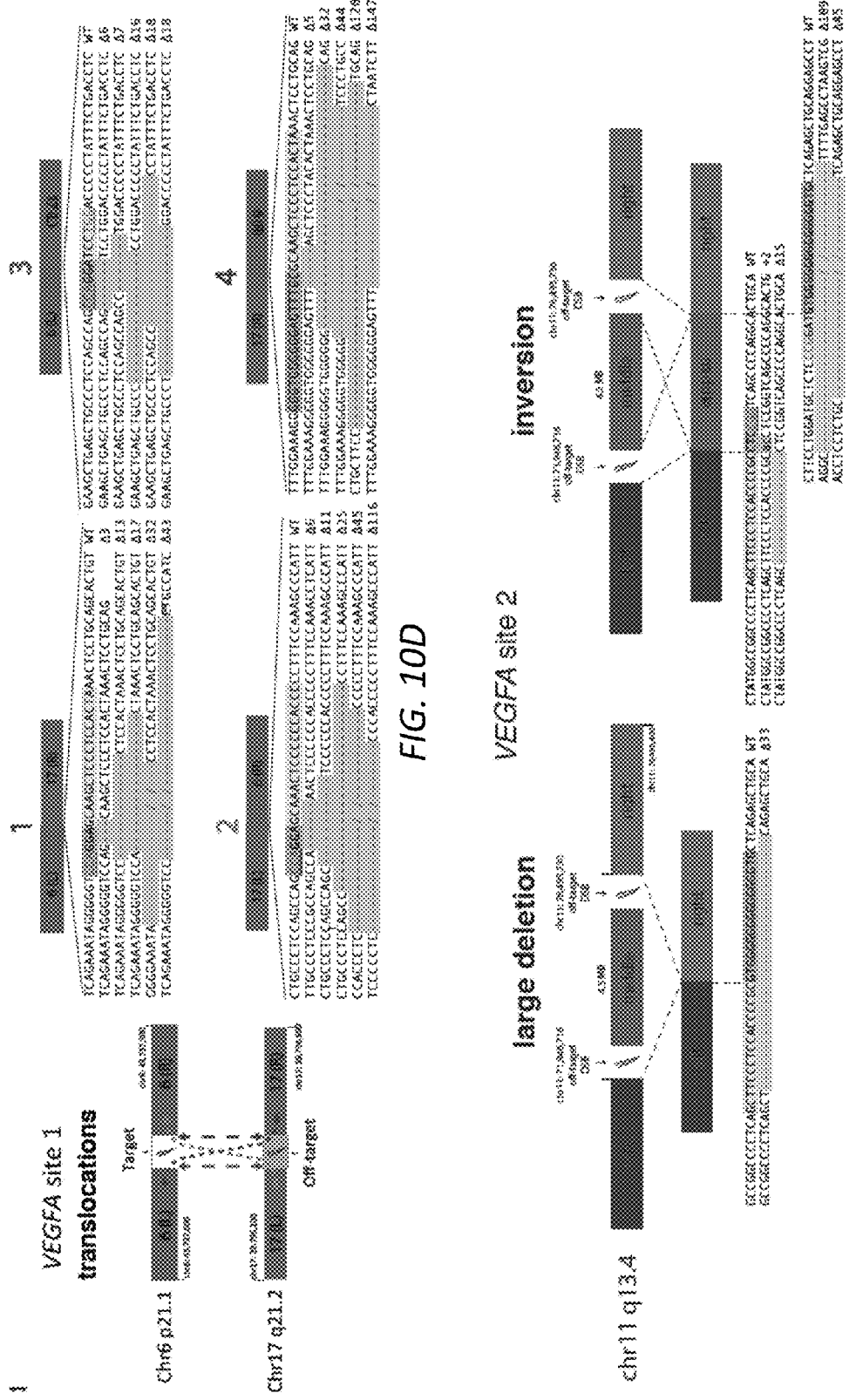

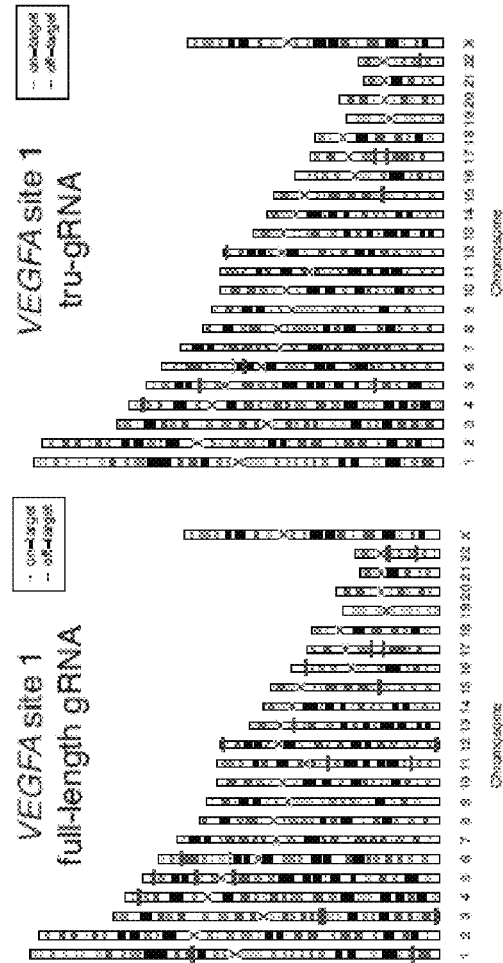
FIG. 10F
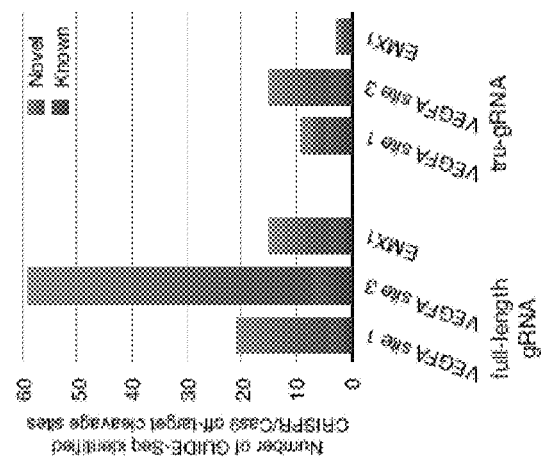
FIG. 11B
FIG. 11A

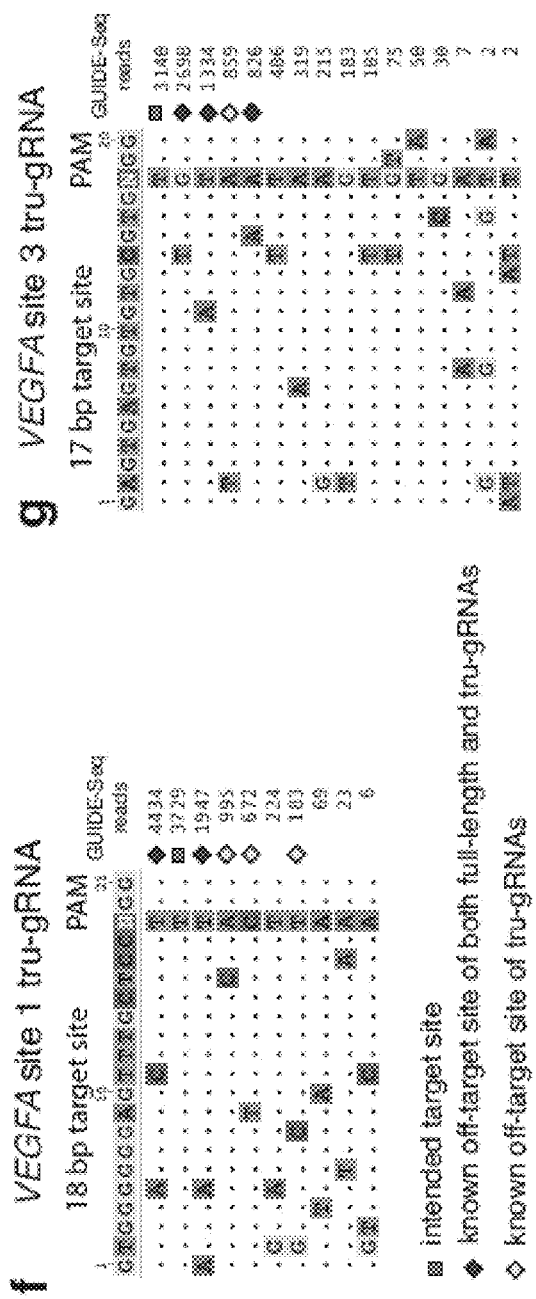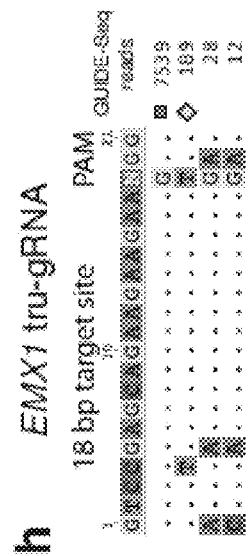
FIG. 11F
FIG. 11G
FIG. 11H

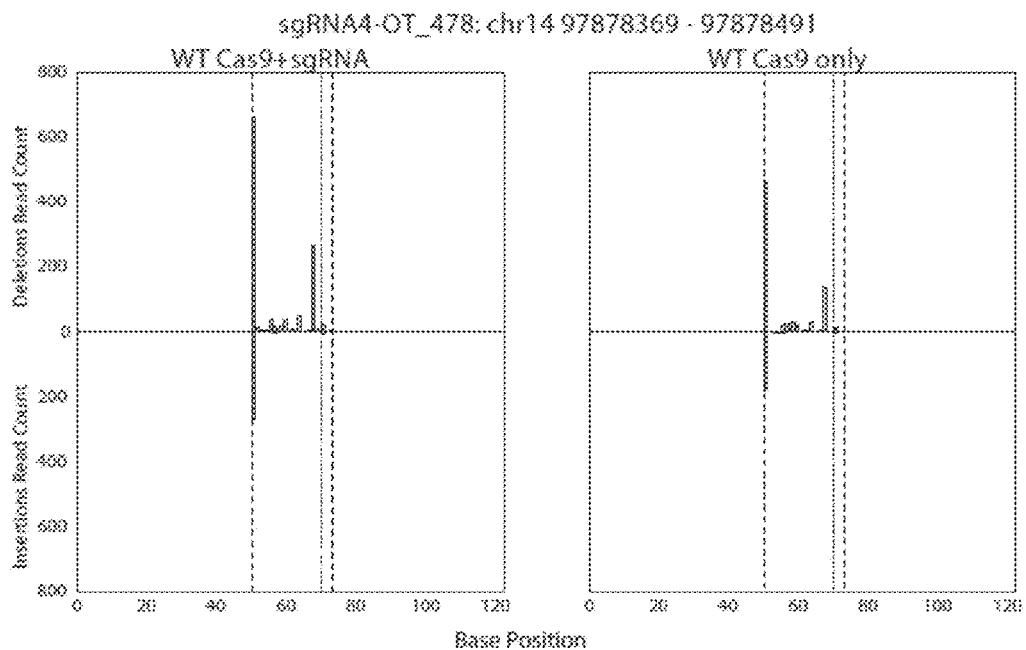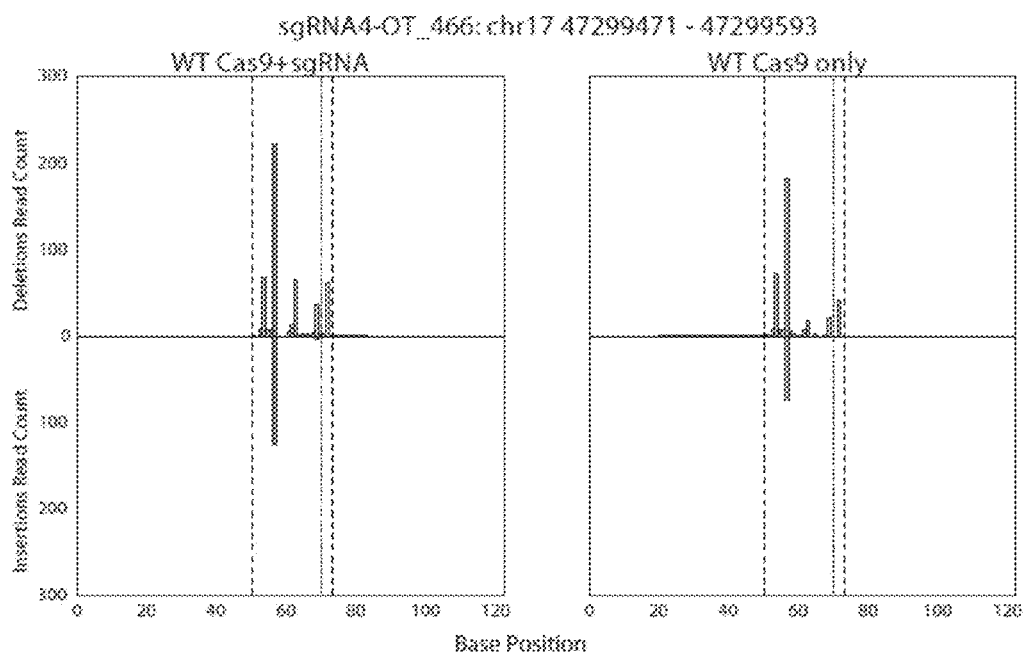
FIG. 15B

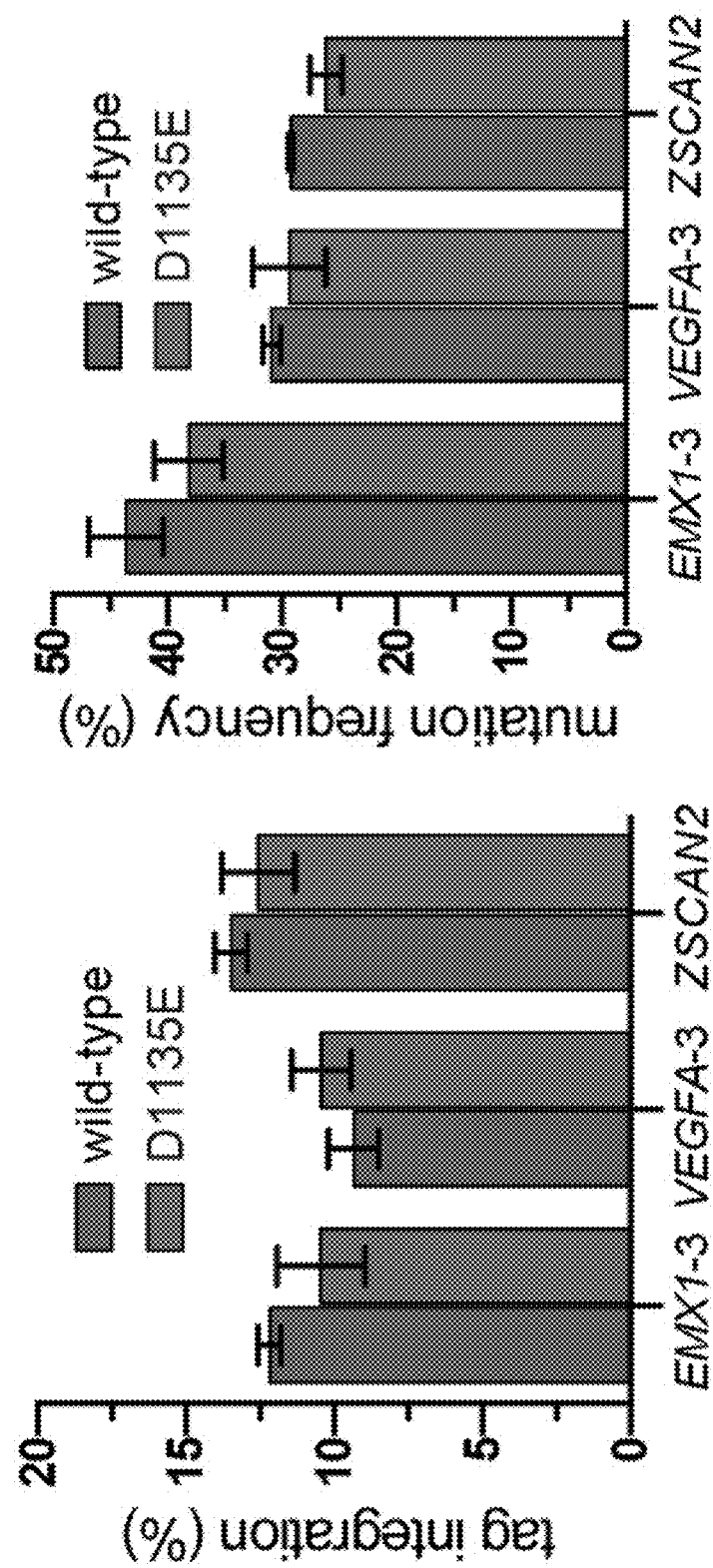

GENOMEWIDE UNBIASED IDENTIFICATION OF DSBS EVALUATED BY SEQUENCING (GUIDE-SEQ)

CLAIM OF PRIORITY

This application is a continuation of PCT/US2015/037269, filed on Jun. 23, 2015, which claims the benefit of U.S. Provisional Patent Application Ser. No. 62/015,911, filed on Jun. 23, 2014; 62/077,844, filed on Nov. 10, 2014; 62/078,923, filed on Nov. 12, 2014; and 62/088,223, filed on Dec. 5, 2014. The entire contents of the foregoing are hereby incorporated by reference.

SEQUENCE LISTING

The instant application contains a Sequence Listing which has been submitted electronically in ASCII format and is hereby incorporated by reference in its entirety. Said ASCII copy, created on Aug. 4, 2015, is named 00786-0786WO1_SL.txt and is 194,742 bytes in size.

FEDERALLY SPONSORED RESEARCH OR DEVELOPMENT

This invention was made with Government support under Grant No. GM105378 awarded by the National Institutes of Health. The Government has certain rights in the invention.

TECHNICAL FIELD

Provided are highly sensitive, unbiased, and genome-wide methods for identifying the locations of engineered nuclease cleavage sites in living cells.

BACKGROUND

A long-held goal of human medicine has been to treat inherited genetic disorders. Genome editing encompasses the powerful concept of directly correcting mutations in endogenous genes to cure or prevent disease. An emerging example of this approach is the clinical trial of a zinc finger nuclease (ZFN) therapeutic engineered to disrupt CCR5, a co-receptor for HIV (1). This ex vivo autologous cell therapy approach attempts to recapitulate the successful cure of HIV in Timothy Brown, the "Berlin Patient," who was transplanted with bone marrow cells from an individual bearing homozygous mutations in CCR5. Another recent example is the correction of X-linked severe combined immunodeficiency disorder by gene targeting with ZFNs in hematopoietic stem cells derived from a 6-month old subject (2).

There are four main classes of engineered nucleases: 1) meganucleases, 2) zinc-finger nucleases, 3) transcription activator effector-like nucleases (TALEN), and 4) Clustered Regularly Interspaced Short Palindromic Repeats (CRISPR) Cas RNA-guided nucleases (RGN).

However, adoption of these new therapeutic and research tools may depend on a demonstration of their specificity. Understanding and identifying off-target effects in human and other eukaryotic cells will be critically essential if these nucleases are to be used widely for research and therapeutic applications.

SUMMARY

GUIDE-Seq provides an unbiased, genomewide and highly sensitive method for detecting mutations, e.g., off-target mutations, induced by engineered nucleases. Thus, the method provides the most comprehensive unbiased method for assessing mutations on a genomewide scale in living mammalian cells. The method can be utilized in any cell type in which dsODNs can be efficiently captured into nuclease-induced DSBs.

Thus, in one aspect, the invention provides methods for detecting double stranded breaks (DSBs), e.g., off-target DSBs, e.g., induced by an exogenous engineered nucleases in genomic DNA of a cell. The methods include contacting the cell with a double-stranded oligodeoxynucleotide (dsODN), preferably wherein the dsODN is between 15 and 75 nts long, e.g., 15-50 nts, 50-75 nts, 30-35 nts, 60-65 nts, or 50-65 nts long, wherein both strands of the dsODN are orthogonal to the genome of the cell; preferably, the 5' ends of the dsODN are phosphorylated; and also preferably, phosphorothioate linkages are present on both 3' ends, or two phosphorothioate linkages are present on both 3' ends and both 5' ends; expressing or activating the exogenous engineered nuclease in the cell, for a time sufficient for the nuclease to induce DSBs in the genomic DNA of the cell, and for the cell to repair the DSBs, integrating a dsODN at one or more DSBs;

amplifying a portion of genomic DNA comprising an integrated dsODN; and sequencing the amplified portion of the genomic DNA, thereby detecting a DSB in the genomic DNA of the cell.

In some embodiments, amplifying a portion of the genomic DNA comprises:

fragmenting the DNA, e.g., by shearing;

ligating ends of the fragmented genomic DNA from the cell with a universal adapter; performing a first round of polymerase chain reaction (PCR) on the ligated DNA with a primer complementary to the integrated dsODN (primer A) and a primer complementary to the universal adapter (primer B);

then performing a second round of PCR using a 3' nested primer complementary to primer A (primer C), a 3' nested primer complementary to primer B (primer D), and a primer complementary to primer D (primer E). In some embodiments, primer E comprises one or more of:

a purification or binding sequence, e.g., a flow-cell binding sequence; and an identification sequence, e.g., a barcode or random molecular index.

In some embodiments, the engineered nuclease is selected from the group consisting of meganucleases, zinc-finger nucleases, transcription activator effector-like nucleases (TALEN), and Clustered Regularly Interspaced Short Palindromic Repeats (CRISPR)/Cas RNA-guided nucleases (CRISPR/Cas RGNs).

In another aspect, the invention provides methods for determining which of a plurality of guide RNAs is most specific, i.e., induces the fewest off-target DSBs. The methods include contacting a first population of cells with a first guide RNA and a double-stranded oligodeoxynucleotide (dsODN), preferably wherein the dsODN is between 15 and 75 nts long, e.g., 15-50 nts, 50-75 nts, 60-65 nts, 30-35 nts or 50-65 nts long, wherein both strands of the dsODN are orthogonal to the genome of the cell; preferably, the 5' ends of the dsODN are phosphorylated; and also preferably, phosphorothioate linkages are present on both 3' ends, or two phosphorothioate linkages are present on both 3' ends and both 5' ends; expressing or activating an exogenous Cas9 engineered nuclease in the first population of cells, for a time sufficient for the nuclease to induce DSBs in the genomic DNA of the cells, and for the cells to repair the DSBs, integrating a dsODN at one or more DSBs;
amplifying a portion of genomic DNA from the first population of cells comprising an integrated dsODN; and
sequencing the amplified portion of the genomic DNA from the first population of cells;
determining a number of sites at which the dsODN integrated into the genomic DNA of the first population of cells;
contacting a second population of cells with a second guide RNA and a double-stranded oligodeoxynucleotide (dsODN), preferably wherein the dsODN is between 15 and 75 nts long, e.g., 15-50 nts, 50-75 nts, 30-35 nts, 60-65 nts, or 50-65 nts long, wherein both strands of the dsODN are orthogonal to the genome of the cell; preferably, the 5' ends of the dsODN are phosphorylated; and also preferably, two phosphorothioate linkages are present on both 3' ends and both 5' ends;
expressing or activating an exogenous Cas9 engineered nuclease in the second population of cells, for a time sufficient for the nuclease to induce DSBs in the genomic DNA of the second population of cells, and for the cells to repair the DSBs, integrating a dsODN at one or more DSBs;
amplifying a portion of genomic DNA comprising an integrated dsODN from the second population of cells; and
sequencing the amplified portion of the genomic DNA from the second population of cells;
determining a number of sites at which the dsODN integrated into the genomic DNA of the second population of cells;
comparing the number of sites at which the dsODN integrated into the genomic DNA of the first population of cells to the number of sites at which the dsODN integrated into the genomic DNA of the second population of cells; wherein the dsODN that integrated at fewer (off-target) sites is more specific. The methods can be repeated for a third, fourth, fifth, sixth, or more populations of cells. "Fewer" off target sites can include both a lesser number of DSB sites and/or reduced frequency of occurrence of a DSB at (one or more) individual sites.

Also provided herein are methods for efficiently integrating a short dsDNA of interest into the site of a DSB by use of an end-protected dsODN as described herein.

In some embodiments, the cell is a mammalian cell.

In some embodiments, wherein the engineered nuclease is a Cas9 nuclease, and the methods also include expressing in the cells a guide RNA, e.g., a single guide or a tracrRNA/crRNA pair, that directs the Cas9 nuclease to a target sequence in the genome.

In some embodiments, the dsODN is biotinylated, e.g., comprises biotin covalently attached to the dsODN, and/or comprises a randomized DNA barcode or Cre or Lox site. The method of any of the above claims, wherein the dsODN is biotinylated.

In some embodiments, the methods described herein include shearing the genomic gDNA into fragments; and isolating fragments comprising a dsODN by binding to the biotin.

In some embodiments, the dsODN is blunt-ended or has 1, 2, 3, or 4 nts overhanging on the 5' end; is phosphorylated on the 5' ends; and/or is phosphorothioated on the 3' ends.

In some embodiments, the dsODN is blunt-ended, is phosphorylated on the 5' ends, and is phosphorothioated on the 3' ends.

In some embodiments, the dsODN contains a randomized DNA barcode, Lox recognition site, restriction enzyme recognition site, and/or tag sequence.

In some embodiments, the methods include shearing the genomic gDNA into fragments; and preparing the fragments for sequencing, e.g., high-throughput sequencing, by end-repair/a-tailing/ligation of a sequencing adapter, e.g., a single-tailed sequencing adapter.

In some embodiments, the DSB is a background genomic DSB (e.g., at a fragile site) or a DSB caused by small-molecule inhibitors of key cellular proteins.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

SEQUENCE LISTING

The instant application contains a Sequence Listing which has been submitted electronically in ASCII format and is hereby incorporated by reference in its entirety. Said ASCII copy, created on Aug. 4, 2015, is named 00786-0786001 SL.txt and is 194,742 bytes in size.

DESCRIPTION OF DRAWINGS

FIGS. 2A-B. Characterization of integration for VEGF site 1. (A) RFLP assay is shown for VEGF site 1, as analyzed on a QIAXCEL capillary electrophoresis instrument, demonstrating successful incorporation of the dsODN bearing the NdeI restriction site. (B) Sanger sequencing data is shown for dsODN integrations at the intended VEGF site 1 target site (SEQ ID NOs:90-103, in order of appearance). The dsODN sequence is highlighted in grey. The site recognized by the guide RNA/Cas9 complex targeted to VEGFA site 1 is highlighted in bold text with the adjacent protospacer adjacent motif (PAM) sequence underlined. The location of the expected double-stranded break induced by Cas9 at this site is indicated with a small black arrow.

Figure 1A:
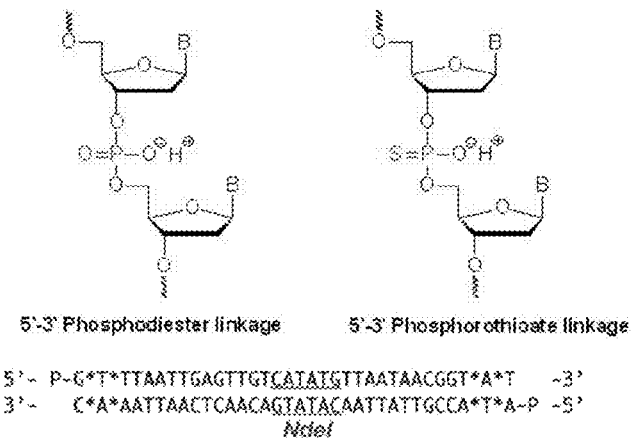
FIGS. 1A-B. Optimization of CRISPR-Cas nuclease-mediated dsODN capture. (a) The sequence of the short oligonucleotide tag used is shown (SEQ ID NOs:1-2, respectively, in order of appearance). All oligonucleotides used are 5' phosphorylated. The tag oligonucleotide also contains a diagnostic NdeI restriction sites that enables estimation of integration frequencies by RFLP. (b) The bottom graph shows integration (%) of the short dsODN by RFLP. The integration rate for dsODNs with both 5' and 3' phosphorothioate linkages (left hand bar in each set) is compared with dsODNs with only 5' phosphorothioate linkage (middle bar in each set) and control without dsODN (right hand bar in each set).

(A) Schematic overview of an exemplary GUIDE-Seq method.

(B) Optimization of dsODN integration into RGN-induced DSBs in human cells. Rates of integration for different modified oligonucleotides as measured by RFLP assay are shown. Control reactions were transfected with only the RGN-encoding plasmids (i.e., without dsODN).

(C) Schematic illustrating how mapping of genomic sequence reads enabled identification of DSB position. Bidirectionally mapping reads or reads mapping to the same direction but amplified by different primers are signatures of DSBs in the GUIDE-seq assay. See also FIG. 1A.

(D) GUIDE-Seq-based identification of RGN-induced DSBs. Start sites of GUIDE-Seq reads mapped to genome enable mapping of the DSB to within a few base pairs. Mapped reads for the on-target sites of the ten RGNs we assessed by GUIDE-Seq are shown. In all cases, the target site sequence is shown with the 20 bp protospacer sequence to the left and the PAM sequence to the right on the x-axis. Note how in all cases the highest peak falls within 3 to 4 bps of the 5'-edge of the NGG PAM sequence, the expected position of an RGN cleavage event.

| TARGET SITE | SEQ ID NO: |
|---|---|
| VEGFA SITE 1 | 273 |
| VEGFA SITE 2 | 274 |
| RNF2 | 275 |
| HEK293 SITE 1 | 276 |
| VEGFA SITE 3 | 277 |
| EMX1 | 278 |
| HEK293 SITE 2 | 279 |
| HEK293 SITE 3 | 280 |
| FANCF | 281 |
| HEK293 SITE 4 | 282 |

(E) Numbers of previously known and novel off-target cleavage sites identified by GUIDE-Seq for the ten RGNs analyzed in this study. All previously known off-target cleavage for 4 RGNs were identified by GUIDE-seq.

(F) Scatterplot of on-target site orthogonality to the human genome (y-axis) versus total number of off-target sites detected by GUIDE-Seq for the ten RGNs of this report. Orthogonality was calculated as the total number of sites in the human genome bearing 1 to 6 mismatches relative to the on-target site.

(G) Scatterplot of on-target site GC content (y-axis) versus total number of off-target sites detected by GUIDE-Seq for the ten RGNs of this report.

(H) Chromosome ideogram of CRISPR/Cas9 on- and off-target sites for the RGN that targets EMX1. Additional ideograms for the remaining RGNs can be found in FIG. 13.

(I) Genomic locations of off-target cleavage sites identified by GUIDE-Seq for the ten RGNs examined in this study.

FIGS. 6A-J. Sequences of off-target sites identified by GUIDE-Seq for ten RGNs. For each RGN, the intended target sequence is shown in the top line with cleaved sites shown underneath and with mismatches to the on-target site shown and highlighted in color. GUIDE-Seq sequencing read counts are shown to the right of each site. The on-target site is marked with a square and previously known off-target sites with a diamond. Data is shown for RGNs targeting the following sites: (A) VEGFA site 1 (SEQ ID NOs:37 and 283-304, respectively, in order of appearance), (B) VEGFA site 3 (SEQ ID NOs:39 and 305-364, respectively, in order of appearance), (C) VEGFA site 2 (SEQ ID NOs:38 and 365-516, respectively, in order of appearance), (D) EMX1 (SEQ ID NOs:36 and 517-532, respectively, in order of appearance), (E) FANCF (SEQ ID NOs:41 and 533-541, respectively, in order of appearance), (F) HEK293 site 1 (SEQ ID NOs:42 and 542-551, respectively, in order of appearance), (G) HEK293 site 2 (SEQ ID NOs:43 and 552-554, respectively, in order of appearance), (H) HEK293 site 3 (SEQ ID NOs:44 and 555-560, respectively, in order of appearance), (I) HEK293 site4 (SEQ ID NO:45 and 561-694, respectively, in order of appearance), (J) RNF2 (SEQ ID NOs:40 and 695, respectively, in order of appearance). No off-target sites were found for the RGN targeted to the RNF2 site.

FIGS. 7A-F. GUIDE-Seq cleavage sites are bona fide RGN off-target mutation sites.

(A) Schematic overview of the AMP-based sequencing method used to confirm indel mutations at GUIDE-Seq cleavage sites is shown in the top half of the figure. Histogram plots of mapped indel mutations are shown for three RGN on-target sites. Deletions are shown above the X-axis whereas insertions are shown below. Boundaries of the overall target site (i.e., protospacer and PAM sequence) are shown with dotted lines and the boundary between the protospacer and PAM sequence is shown as a dotted line between the other two. RGN cleavage is predicted to occur 3 to 4 bps from the 5' edge of the protospacer.

(B)-(F) Scatterplots of indel frequencies (x-axis) and GUIDE-Seq sequencing read counts (y-axis) for cleavage sites identified by GUIDE-Seq for RGNs targeted to: VEGFA site 1, VEGFA site 2, VEGFA site 3, EMX1, and FANCF.

FIG. 8A-E Analysis of RGN-induced off-target sequence characteristics (A) Fraction of potential RGN off-target sites bearing a certain number of mismatches that are cleaved (as detected by GUIDE-Seq).

(B) Plots of GUIDE-Seq read counts (log-scale) for RGN off-target cleavage sites bearing a certain number of mismatches (C) Effects of mismatch position within the protospacer on GUIDE-Seq read counts for RGN off-target sites. Bases are numbered 1 to 20 with 20 being the base adjacent to the PAM.

(D) Effects of wobble transition, non-wobble transition, and transversion mismatches estimated by linear regression analysis.

(E) Fraction of GUIDE-Seq read count variance explained by individual univariate analyses for the effect of mismatch number, mismatch type, mismatch position, PAM density, expression level, and genomic position (intergenic/exon/intron).

FIGS. 9A-F. Comparisons of GUIDE-Seq with computational prediction or ChIP-Seq methods for identifying RGN off-target sites
- (A) Venn diagrams illustrating overlap between off-target sites predicted by the MIT CRISPR Design Tool and GUIDE-Seq for nine RGNs.
- (B) Venn diagrams illustrating overlap between off-target sites predicted by the E-CRISP computational prediction program and GUIDE-Seq for nine RGNs.
- (C) Histogram showing the numbers of bona fide RGN off-target sites identified by GUIDE-Seq that are predicted, not predicted, and not considered by the MIT CRISPR Design Tool. Sites predicted by the MIT CRISPR Design Tool are divided into quintiles based on the score provided by the program. Each bar has the sites sub-classified based on the number of mismatches relative to the on-target site. Bulge sites are those that have a skipped base position at the gRNA-protospacer DNA interface.
- (D) Histogram showing the numbers of bona fide RGN off-target sites identified by GUIDE-Seq that are predicted, not predicted, and not considered by the E-CRISP computational prediction tool. Sites are subdivided as described in (c).
- (E) Venn diagrams illustrating overlap between dCas9 binding sites identified by ChIP-Seq and RGN off-target cleavage sites identified by GUIDE-Seq.
- (F) Histogram plots of RGN off-target sites identified by GUIDE-Seq and dCas9 binding sites identified by ChIP-Seq classified by the number of mismatches in the sequence relative to the intended on-target site. Kernel density estimation of GUIDE-Seq and ChIP-Seq mismatches is depicted. Dotted lines indicate the mean number of mismatches for each class of sites.

FIG. 10A-F Large-scale structural alterations induced by RGNs
- (A) Schematic overview of AMP strategy for detecting translocations. Additional details in Methods.
- (B) Circos plots of structural variation induced by RGNs. Data for five RGNs and a control of cells are shown. Chromosomes are arranged in a circle with translocations shown as arcs between two chromosomal locations. Deletions or inversions greater than 1 kb in length are shFwn as straight lines. Sites that are not on-target, off-target, or breakpoint hotspots are classified as "other".
- (C) Example of a translocation detected between the VEGFA site 1 on-target site on chromosome 6 and an off-target site on chromosome 17. All four possible reciprocal translocations were detected using AMP.
- (D) Examples of large deletion and inversion between two off-target sites in VEGFA site 2 detected by AMP. Sequences in section 1 disclosed as SEQ ID NOS 696-703, respectively, in order of appearance, sequences in section 2 disclosed as SEQ ID NOS 704-711, respectively, in order of appearance, sequences in section 3 disclosed as SEQ ID NOS 712-717, respectively, in order of appearance, and sequences in section 4 disclosed as SEQ ID NOS 718-726, respectively, in order of appearance.
- (e) Summary table of different RGN-induced and RGN-independent structural variations observed with five RGNs. Controls with Cas9 only, dsODN oligo only, and cells only are also shown. Sequences in section labeled "large deletion" disclosed as SEQ ID NOS 727-728, respectively, in order of appearance and sequences in section labeled "inversion" disclosed as SEQ ID NOS 729-736, respectively, in order of appearance.
- (F) Chromosome ideogram illustrating the locations of breakpoint hotspots in U2OS and HEK293 cells. Two hotspots overlap at the centromeric regions of chromosomes 1 and 10.

FIG. 11A-H. GUIDE-Seq profiles of RGNs directed by tru-gRNAs
- (A) Numbers of previously known and novel off-target cleavage sites identified for RGNs directed to the to VEGFA site 1, VEGFA site 3, and EMX1 target sites by matched full-length gRNAs and truncated gRNAs. Note that the data for the RGNs directed by full-length gRNAs are the same as those presented in FIGS. 1e and is shown again here for ease of comparison.
- (B)-(D) Chromosome ideograms showing on- and off-target sites for RGNs directed to the VEGFA site 1, VEGFA site 3, and EMX1 target sites by matched full-length gRNAs and truncated gRNAs. Note that the ideograms for the RGNs directed by full-length gRNAs are the same as those presented in FIG. 1h and FIGS. 13A-B and are shown again here for ease of comparison.
- (E) GUIDE-Seq-based identification of DSBs induced by RGNs directed by tru-gRNAs. Mapped reads for the on-target sites of the three RGNs directed by tru-gRNAs we assessed by GUIDESeq are shown (SEQ ID NOS 737-739, respectively, in order of appearance). In all cases, the target site sequence is shown with the 20 bp protospacer sequence to the left and the PAM sequence to the right on the x-axis. As with RGNs directed by full-length gRNAs, note how the highest peak falls within 3 to 4 bps of the 5'-edge of the NGG PAM sequence, the expected position of an RGN cleavage event.
- (F)-(H) Sequences of off-target sites identified by GUIDE-Seq for RGNs directed by tru-gRNAs. For each RGN, the intended target sequence is shown in the top line with cleaved sites shown underneath and with mismatches to the on-target site shown and highlighted in color. GUIDESeq sequencing read counts are shown to the right of each site. The intended on-target site is marked with a square, previously known off-target sites of RGNs directed by both a full length gRNA and a tru-gRNA are marked with a dark grey diamond, and previously known off-target sites found only with RGNs directed by a tru-gRNA are marked with a light grey diamond. Previously known off-target sites were those that were shown to have a mutagenesis frequency of 0.1% or higher in an earlier report FU et al., Nat Biotechnol 32, 279-284 (2014)). Data is shown for RGNs directed by tru-gRNAs to the (f) VEGFA site 1 (SEQ ID NOS 87 and 740-749, respectively, in order of appearance), (g) VEGFA site 3 (SEQ ID NOS 88 and 750-765, respectively, in order of appearance), and (h) EMX1 (SEQ ID NOS 89 and 766-769, respectively, in order of appearance) target sites.

Figure 12:
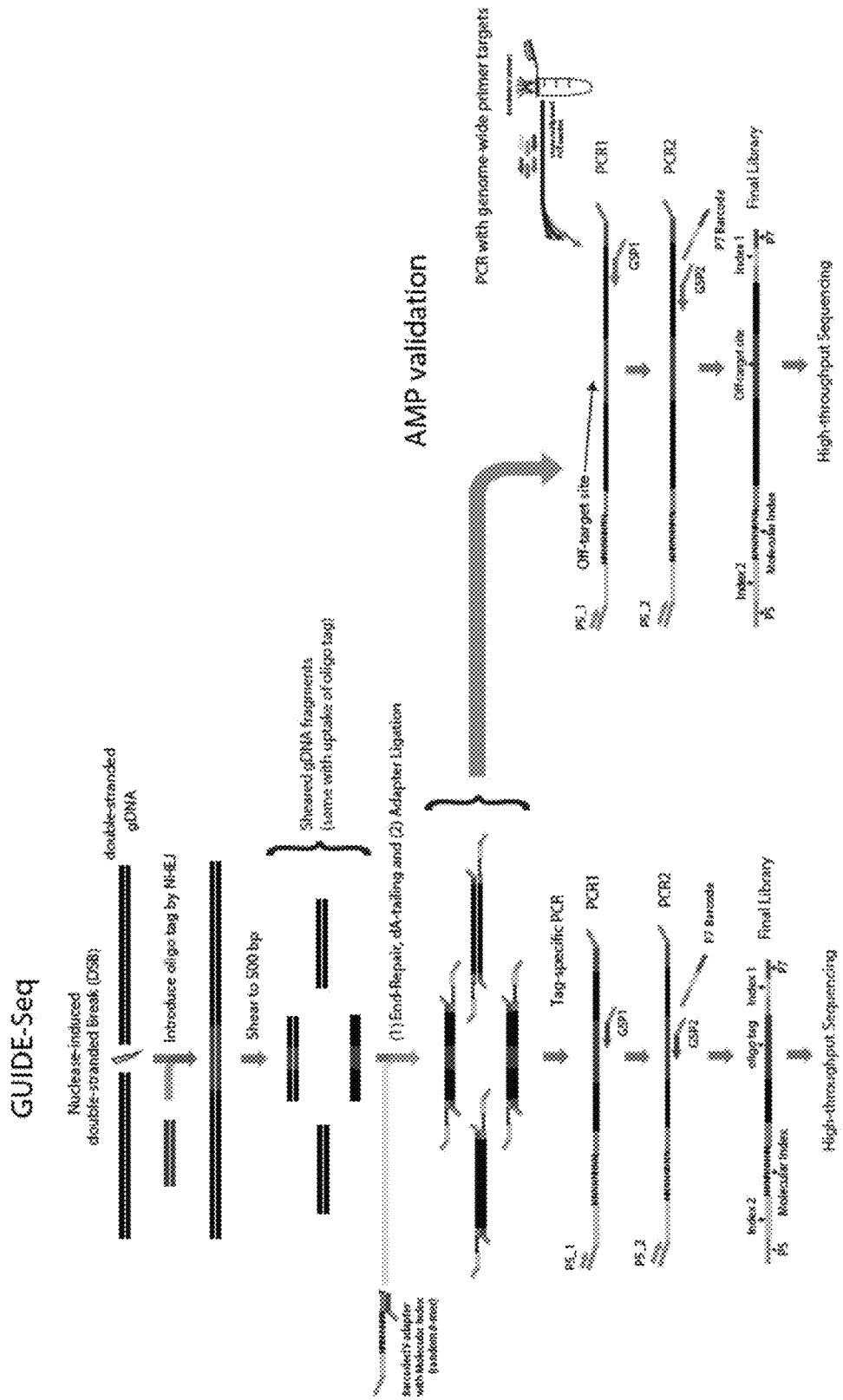
Figures 13A, 13B, 13C:
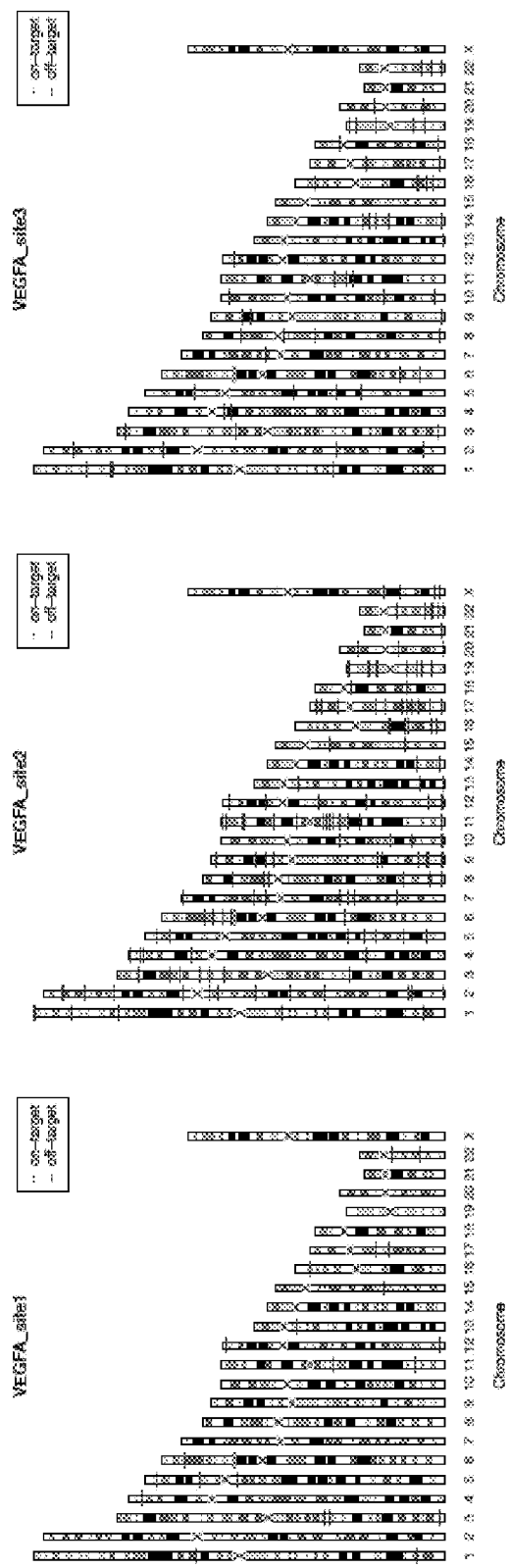
Figures 13D, 13E, 13F:
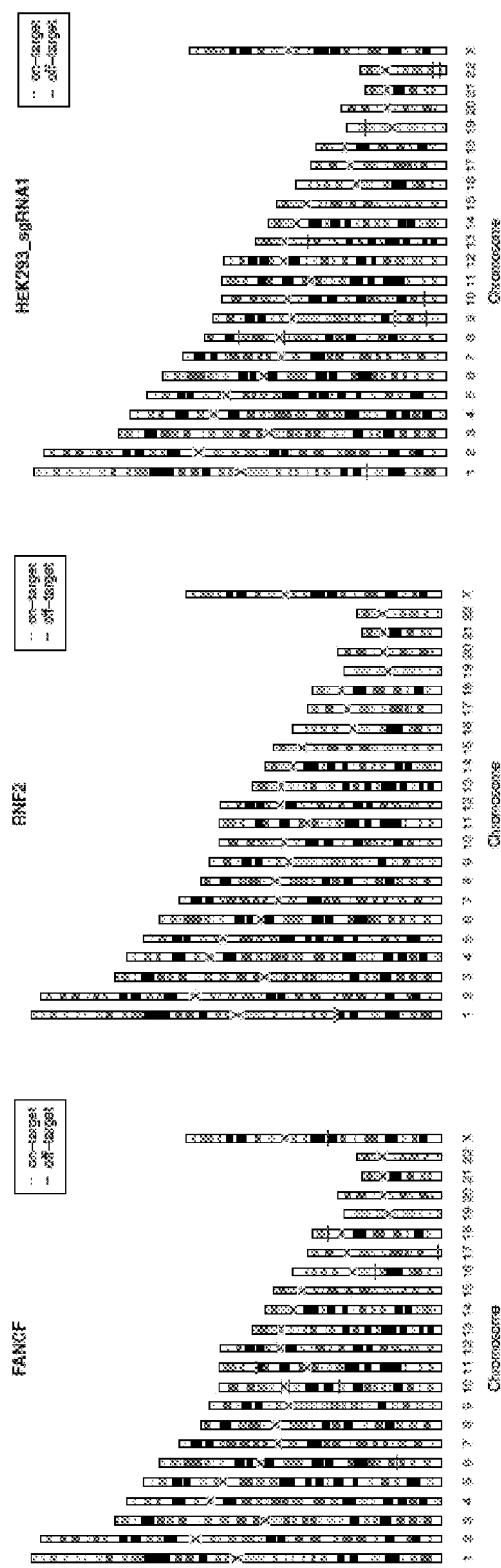
Figure 13I:
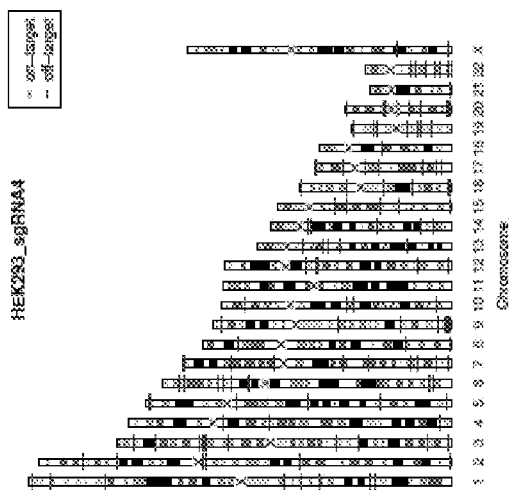
Figure 13H:
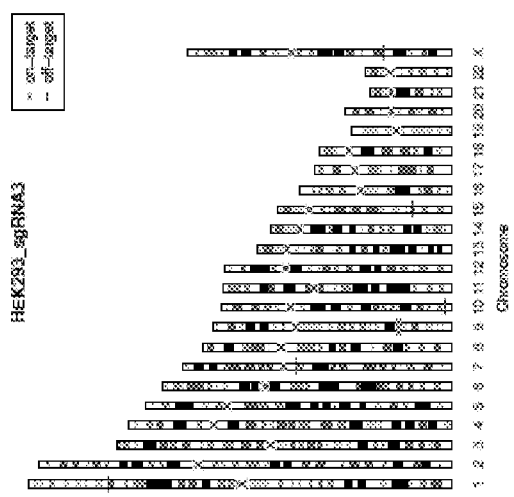
Figure 13G:
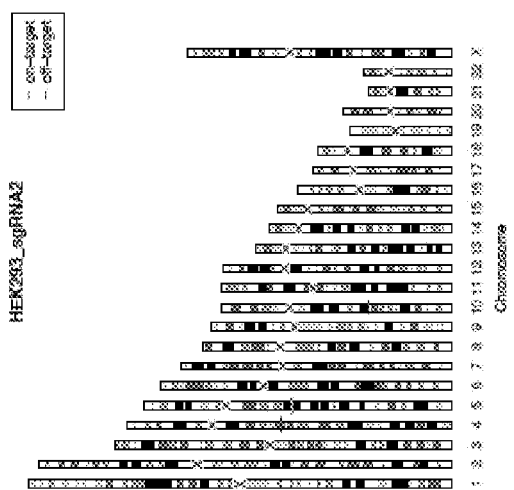
Figure 13J:
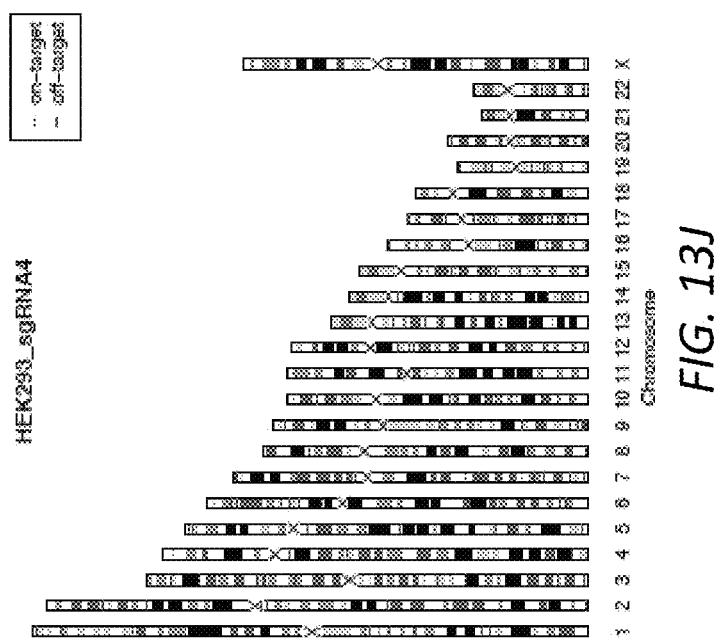

FIG. 12. Detailed schematic overview of GUIDE-Seq and AMP-based sequencing for validation of dsODN insertions and indel mutations. Details for both protocols can be found in Methods.

FIG. 13A-J. Chromosome ideograms of CRISPR/Cas9 on- and off-target sites for all ten RGNs evaluated by GUIDE-Seq FIG. 14. Multi-factor linear regression model to show independent effects of factors on GUIDE-Seq read count FIGS. 15A-D. Histogram plots of mapped indel mutations for seven ChIP-Seq binding sites previously characterized as off-target cleavage sites Experimental and control samples are shown side-by-side for each site.

Figure 16A:
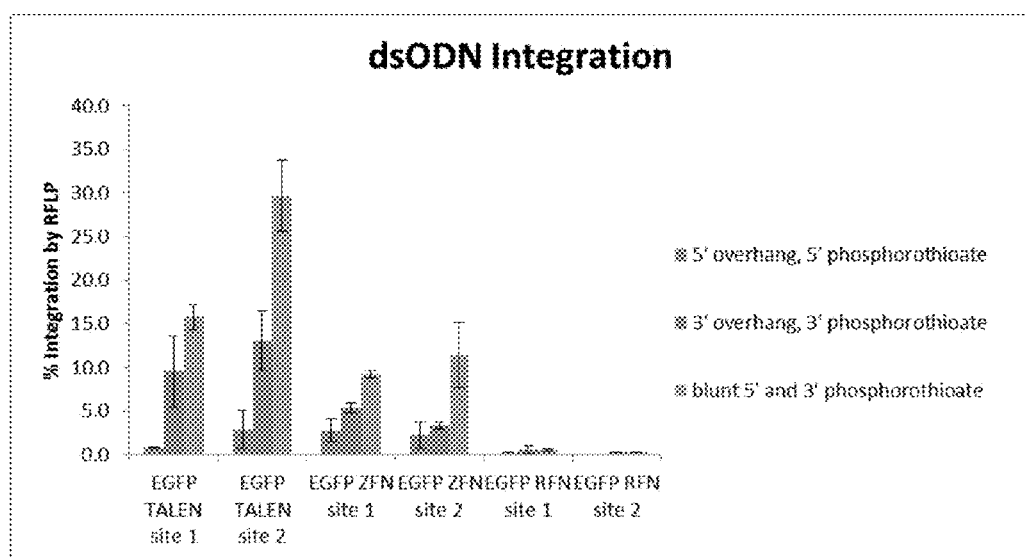

FIG. 16A is a graph showing integration frequencies of 3 types of dsODNs using TALENs, ZFNs, and RFNs targeted against EGFP. All of the dsODNs were 5' phosphorylated. The dsODNs had either a randomized 5'- or 3'-4-bp overhang or were blunt, as indicated.

Figures 16B, 16C:
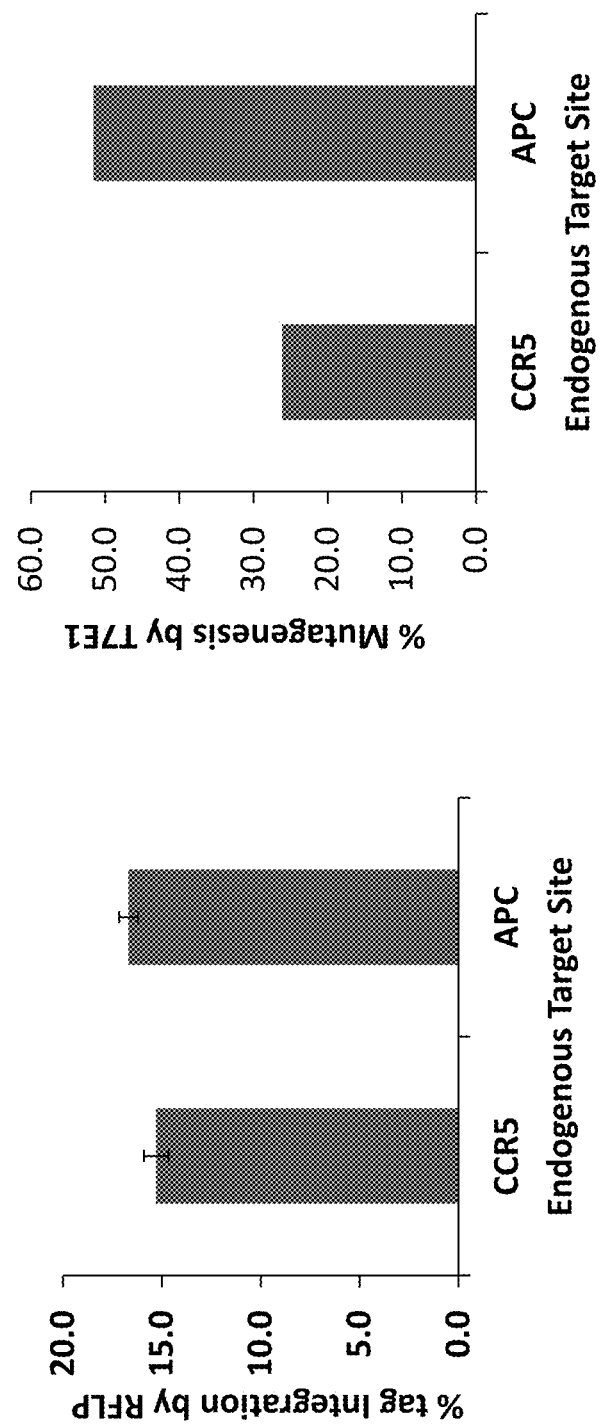

FIGS. 16B-C are graphs showing efficient integration of a blunt, 5'-phosphorylated, 34-bp double-stranded oligodeoxynucleotide (dsODN) (oSQT685/686) into double-stranded breaks (DSBs) induced by TALENs at 2 endogenous target sites, CCR5 and APC in U2OS cells. (16B) RFLP analysis shows % integration of dsODN tag oSQT685/686 into DSBs induced by TALENs at 2 endogenous sites, CCR5 and APC. (16C) Cumulative mutagenesis frequencies are measured by T7E1 assay at these 2 endogenous target sites.

Figure 17A:
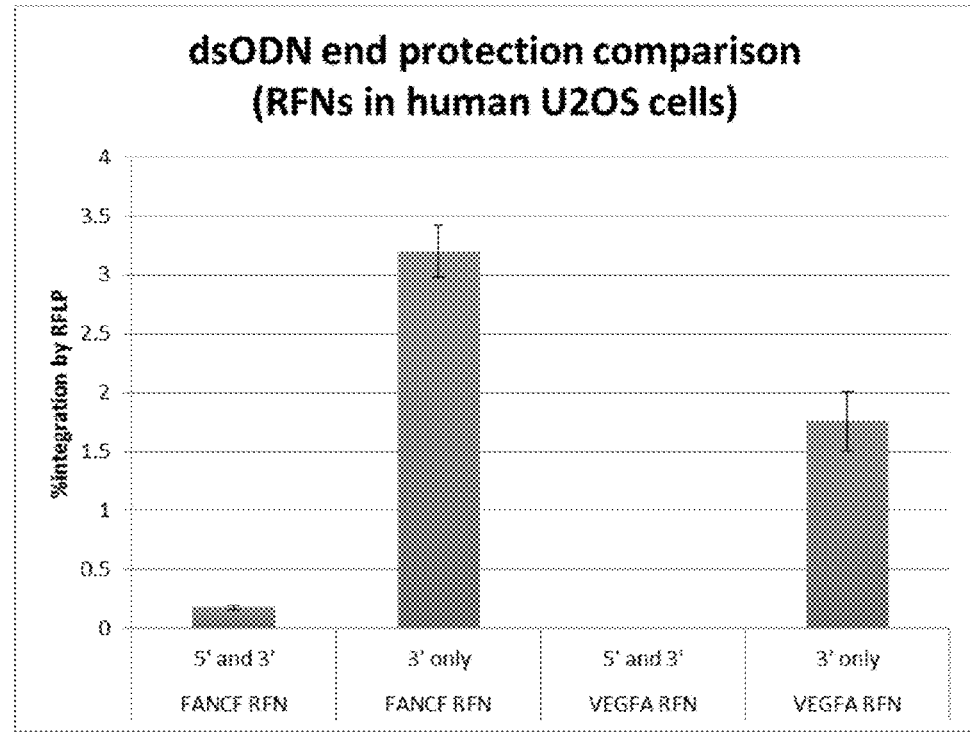
Figure 17B:
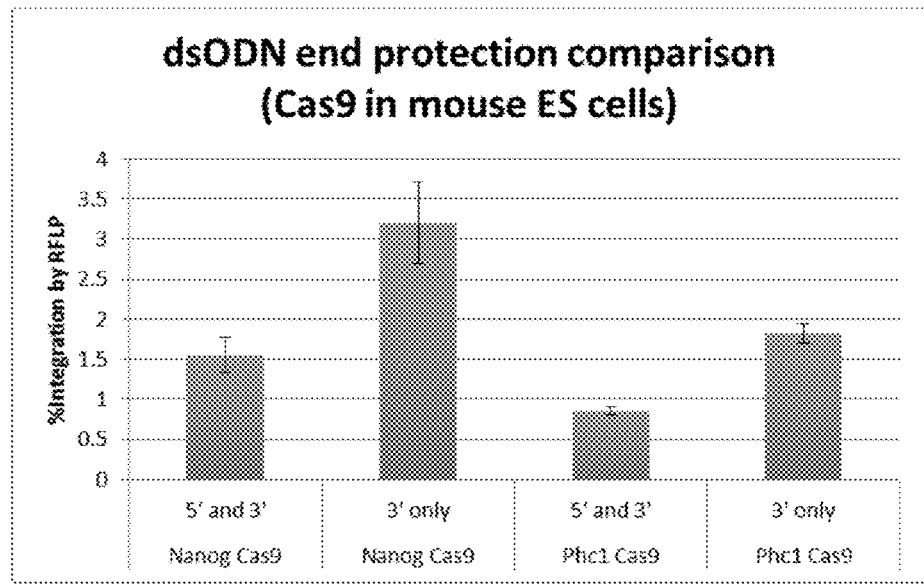

FIGS. 17A and 17B are bar graphs showing a comparison of different dsODN end protections; dsODNs used in this experiment were phosphorylated and blunt and had either both 5' and 3' phosphorothioate modifications, or only 3' phosphorothioate modifications. 17A, RFNs in human U2OS cells; 17B, Cas9 in mouse ES cells.

Figure 18A:
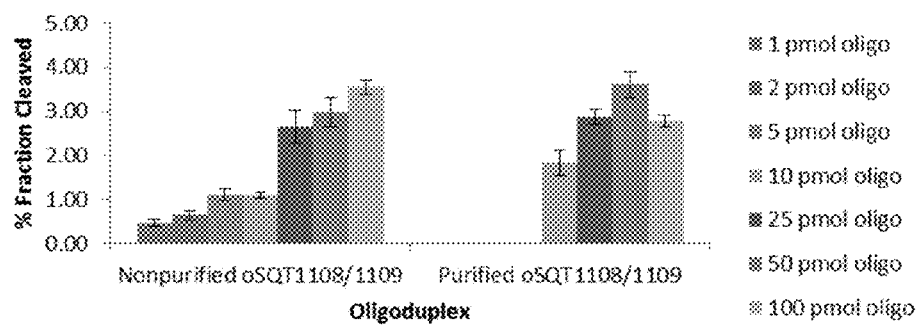
Figure 18B:
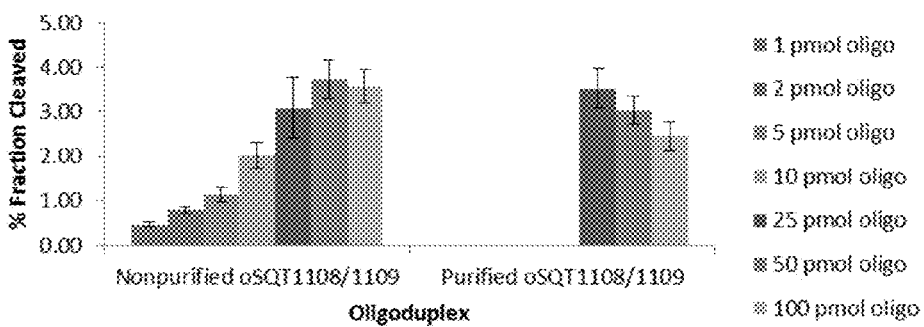

FIGS. 18A-B are graphs showing experiments at different concentrations of 3' phosphorothioate modified oligo in mouse ES cells. 18A, Nanog sgRNA/Cas9; 18B, Phc1 sgRNA/Cas9. The dsODNs were phosphorylated and blunt and had either both 5' and 3' phosphorothioate modifications, or only 3' phosphorothioate modifications. The experiments were conducted with dimeric RNA-guided FokI nucleases in human U2OS cells (FIG. 18A), or with standard Cas9 in mouse ES cells (FIG. 18B).

Figure 18C:
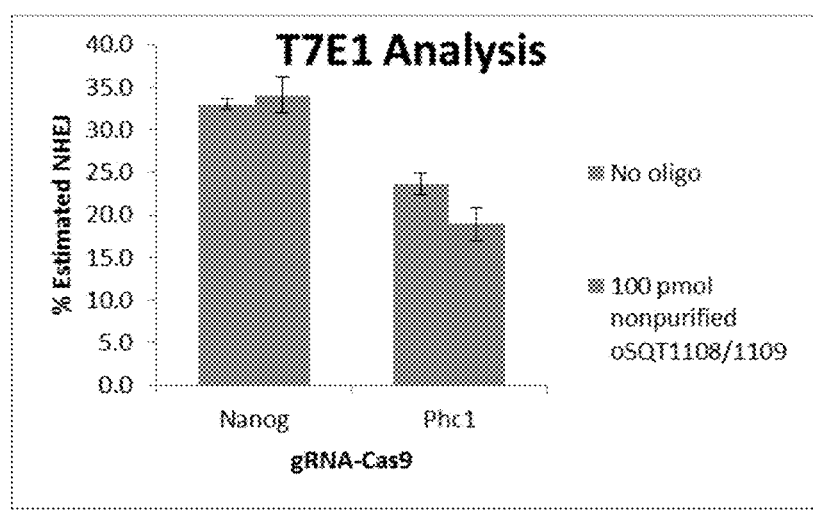

FIG. 18C is a graph showing T7E1 analysis of the rate of disruption in the presence of 3' phosphorothioate modified oligo in mouse ES cells.

Figures 19A, 19B:
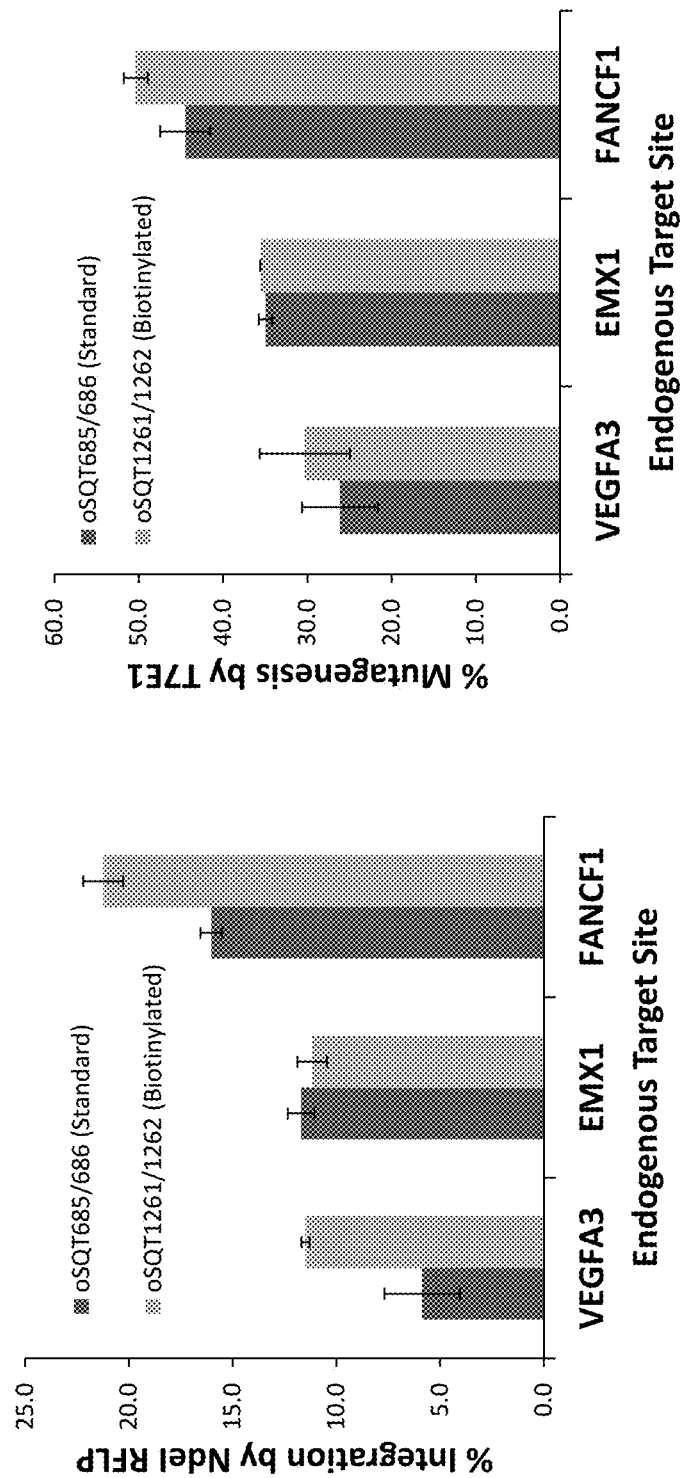

FIGS. 19A-B show efficient integration of biotinylated dsODN tags into double-stranded breaks (DSBs) induced by Cas9 at 3 endogenous target sites, VEGFA3, EMX1, and FANCF1 in U2OS cells. (19A) RFLP analysis shows % integration rates of biotinylated dsODN (oSQT1261/1262), compared to the standard dsODN (oSQT685/686) into DSBs induced by Cas9 at 3 endogenous sites, VEGFA3, EMX1, and FANCF1 in U2OS cells. (19B) T7EI shows % estimated mutagenesis frequencies with biotinylated dsODN (oSQT1261/1262), compared to the standard dsODN (oSQT685/686) at 3 endogenous sites, VEGFA3, EMX1, and FANCF1 in U2OS cells.

Figures 20A, 20B:
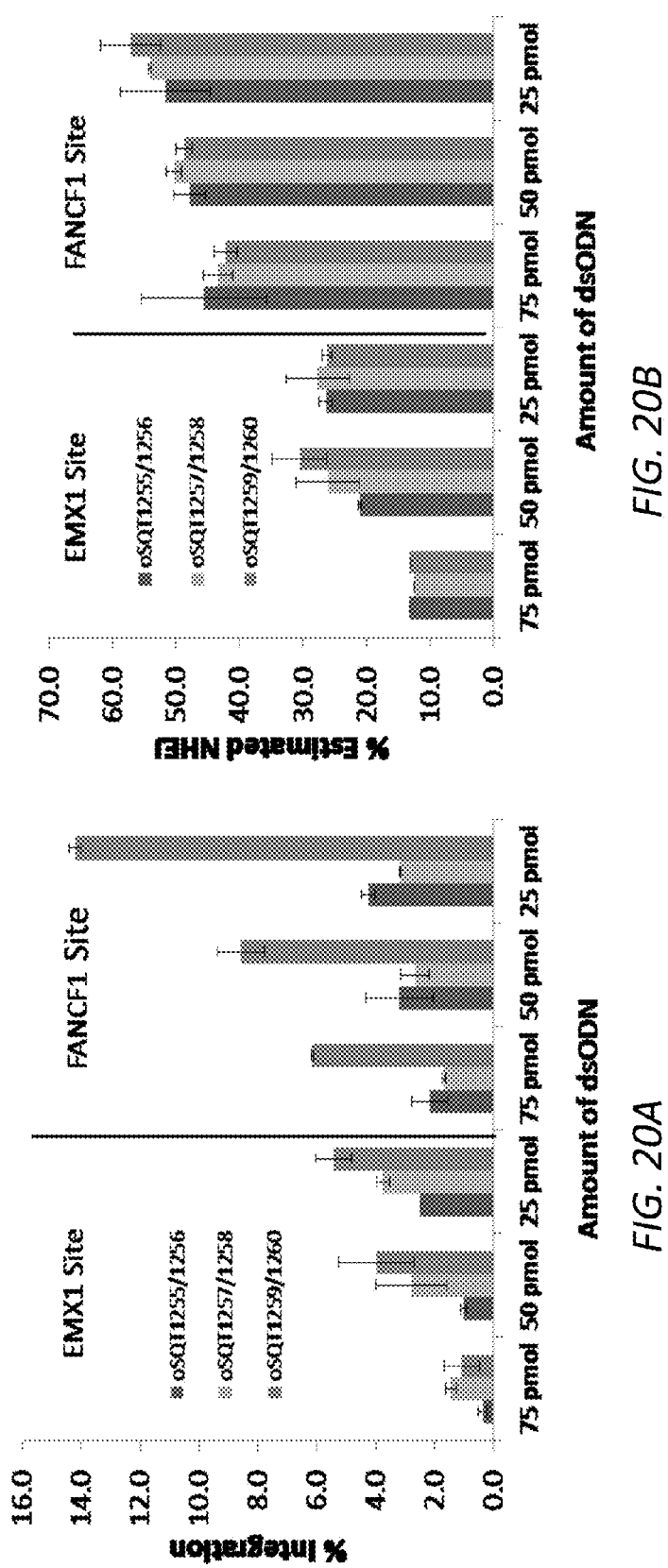

FIGS. 20A-B show that longer dsODN tags can be optimized to integrate efficiently at sites of CRISPR-Cas9 induced DSBs. (20A) RFLP analysis shows % integration rates of 60-bp dsODNs (oSQT1255/1256, oSQT1257/1258, and oSQT1259/1260) when being transfected with 75, 50, or 25 pmol. Tested at 2 endogenous sites, EMX1 and FANCF1 in U2OS cells. (20B) T7EI shows % estimated NHEJ rates of 60-bp dsODNs (oSQT1255/1256, oSQT1257/1258, oSQT1259/1260 when being transfected with 75, 50, or 25 pmol. Tested at 2 endogenous sites, EMX1 and FANCF1 in U2OS cells.

Figure 21:
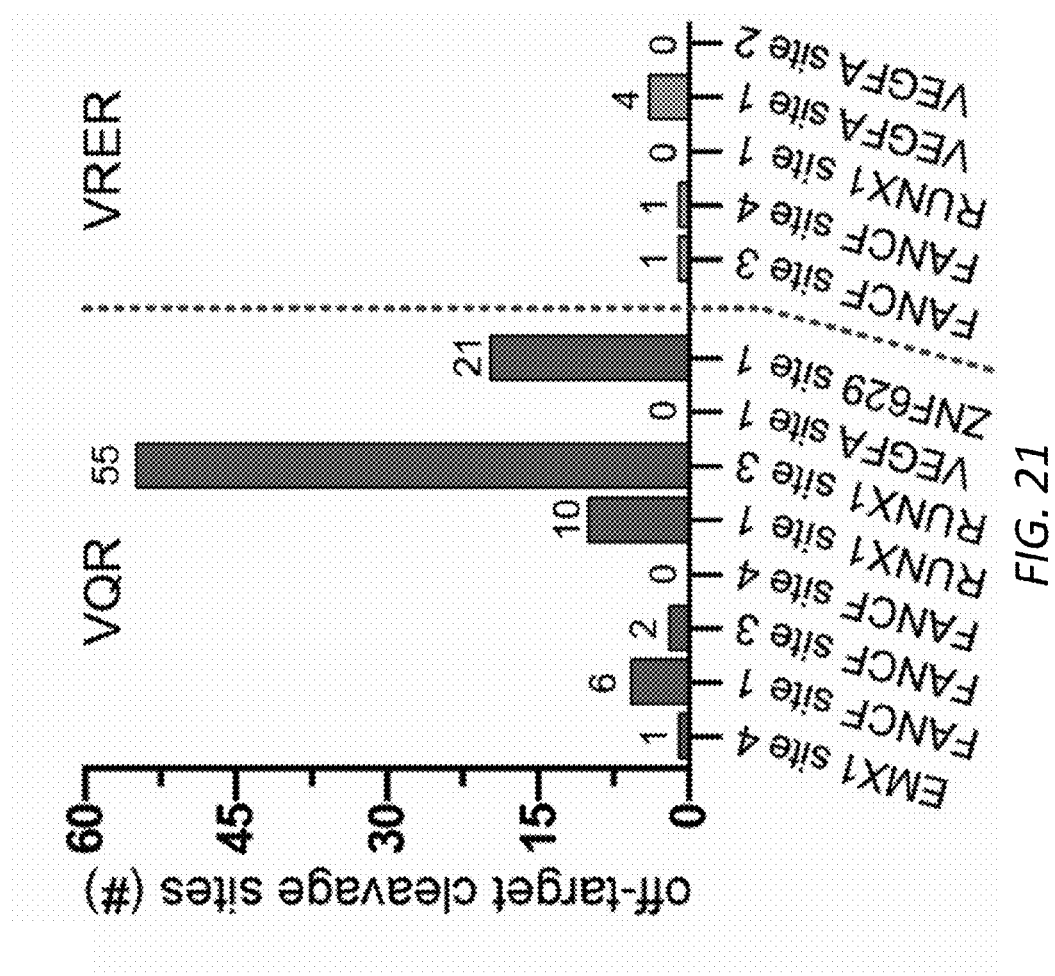

FIG. 21 is a graph showing the number of off-target cleavage sites identified by GUIDE-seq for the engineered VQR and VRER SpCas9 variants using different sgRNAs.

Figure 22:
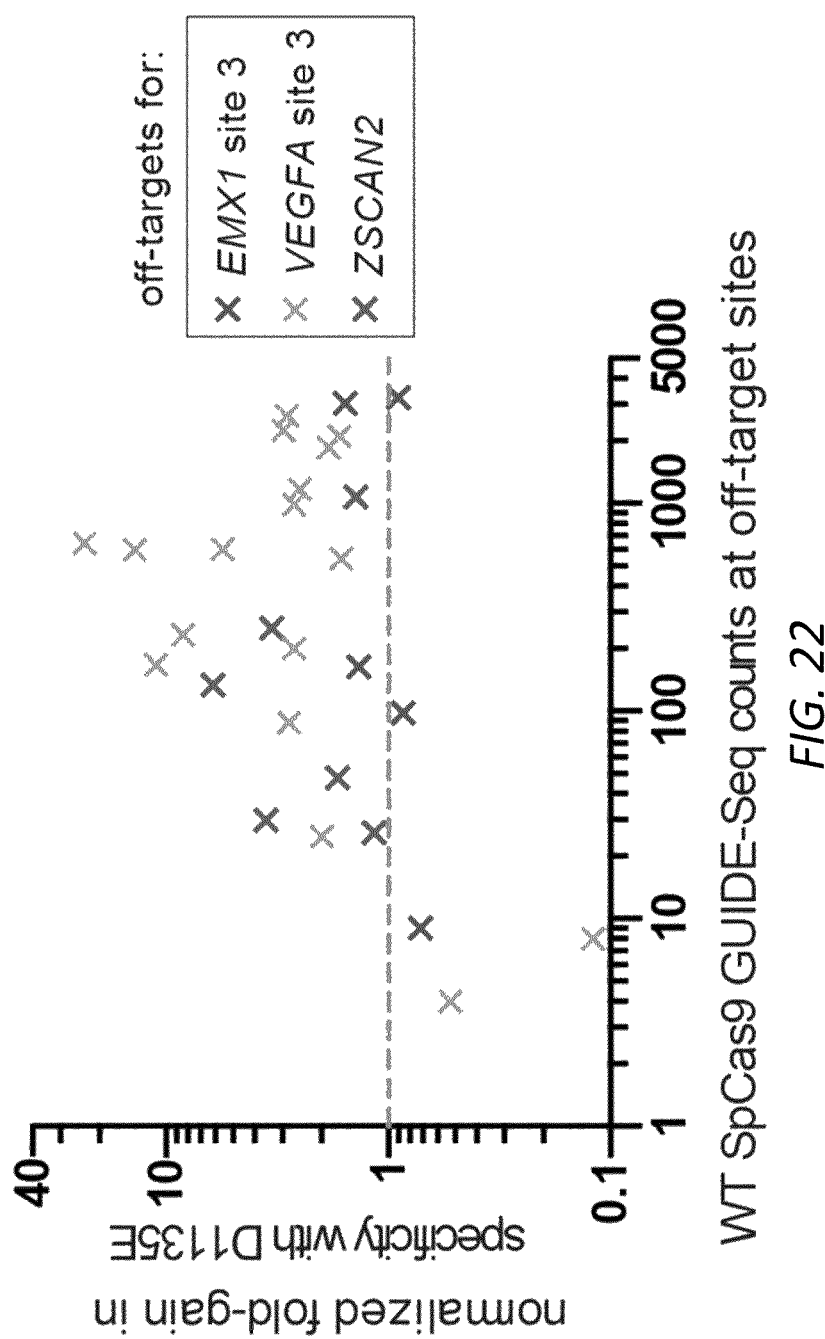

FIG. 22 is a graph summarizing GUIDE-seq detected changes in specificity between wild-type and D1135E SpCas9 variants at off-target sites. Estimated fold-gain in specificity at sites without read-counts for D1135E are not plotted.

FIGS. 23A-B are graphs showing (23A) Mean frequency of GUIDE-seq oligo tag integration at the on-target sites, estimated by restriction fragment length polymorphism analysis. Error bars represent s.e.m., n=4; (23B) Mean mutagenesis frequencies at the on-target sites detected by T7E1 for GUIDE-seq experiments. Error bars represent s.e.m., n=4.

DETAILED DESCRIPTION

The Genomewide Unbiased Identification of DSBs Evaluated by Sequencing (GUIDE-Seq) methods described herein provide highly sensitive, unbiased, and genome-wide methods for identifying the locations of engineered nuclease cleavage sites in living cells, e.g., cells in which the non-homologous end-joining (NHEJ) repair pathway is active. In some embodiments, the method relies on the capture of short double-stranded oligodeoxynucleotides (dsODNs) into nuclease-induced breaks (a process presumed to be mediated by the NHEJ pathway) and then the use of the inserted dsODN sequence to identify the sites of genomic insertion, e.g., using a PCR-based deep sequencing approach in which the inserted dsODN sequence is used to selectively amplify the sites of genomic insertion for high-throughput sequencing, or selectively pulling down genomic fragments including the inserted dsODNs using an attached tag such as biotin, e.g., using solution hybrid capture. Described herein is the development and validation of the GUIDE-Seq method in cultured human cells; the general approach described herein should work in all mammalian cells and in any cell type or organism in which the NHEJ pathway is active or presumed to be active.

The potential off-target sites identified by this initial sequencing process might also be analyzed for indel mutations characteristic of NHEJ repair in cells in which only the nuclease components are expressed. These experiments, which could be performed using amplification followed by deep sequencing, would provide additional confirmation and quantitation of the frequency of off-target mutations induced by each nuclease.

Double-Stranded Oligodeoxynucleotides (dsODNs)

In the methods described herein, a non-naturally occurring dsODN is expressed in the cells. In the present methods, both strands of the dsODN are orthogonal to the genome of the cell (i.e., are not present in or complementary to a sequence present in, i.e., have no more than 10%, 20%, 30%, 40%, or 50% identity to a sequence present in, the genome of the cell). The dsODNs can preferably be between 15 and 75 nts long, e.g., 15-50 nts, 50-75 nts, 30-35 nts, 60-65 nts, or 50-65 nts long, or between 15 and 50 nts long, e.g., 20-40 or 30-35, e.g., 32-34 nts long. Each strand of the dsODN should include a unique PCR priming sequence (i.e., the dsODN includes two PCR primer binding sites, one on each strand). In some embodiments, the dsODN includes a restriction enzyme recognition site, preferably a site that is relatively uncommon in the genome of the cell.

The dsODNs are preferably modified; preferably, the 5' ends of the dsODN are phosphorylated; and also preferably, two phosphorothioate linkages are present on both 3' ends and both 5' ends. In preferred embodiments, the dsODN is blunt ended. In some embodiments, the dsODNs include a random variety of 1, 2, 3, 4 or more nucleotide overhangs on the 5' or 3' ends.

The dsODN can also include one or more additional modifications, e.g., as known in the art or described in PCT/US2011/060493. For example, in some embodiments, the dsODN is biotinylated. The biotinylated version of the GUIDE-seq dsODN tag is used as a substrate for integration into the sites of genomic DSBs. The biotin can be anywhere internal to the dsODN (e.g., a modified thymidine residue (Biotin-dT) or using biotin azide), but not on the 5' or 3' ends. As shown in Example 4, it is possible to integrate such an oligo efficiently. This provides an alternate method of recovering fragments that contain the GUIDE-seq dsODN tag. Whereas in some embodiments, these sequences are retrieved and identified by nested PCR, in this approach they are physically pulled down by using the biotin, e.g., by binding to streptavidin-coated magnetic beads, or using solution hybrid capture; see, e.g., Gnirke et al., Nature Biotechnology 27, 182-189 (2009). The primary advantage is retrieval of both flanking sequences, which reduces the dependence on mapping sequences to a reference genome to identify off-target cleavage sites.

Engineered Nucleases

There are four main classes of engineered nucleases: 1) meganucleases, 2) zinc-finger nucleases, 3) transcription activator effector-like nucleases (TALEN), and 4) Clustered Regularly Interspaced Short Palindromic Repeats (CRISPR) Cas RNA-guided nucleases (RGN). See, e.g., Gaj et al., Trends Biotechnol. 2013 July; 31(7):397-405. The nuclease can be transiently or stably expressed in the cell, using methods known in the art; typically, to obtain expression, a sequence encoding a protein is subcloned into an expression vector that contains a promoter to direct transcription. Suitable eukaryotic expression systems are well known in the art and described, e.g., in Sambrook et al., *Molecular Cloning, A Laboratory Manual* (4th ed. 2013); Kriegler, *Gene Transfer and Expression: A Laboratory Manual* (2006); and *Current Protocols in Molecular Biology* (Ausubel et al., eds., 2010). Transformation of eukaryotic and prokaryotic cells are performed according to standard techniques (see, e.g., the reference above and Morrison, 1977, J. Bacteriol. 132:349-351; Clark-Curtiss & Curtiss, Methods in Enzymology 101:347-362 (Wu et al., eds, 1983).

Homing Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G, et al., Current Gene Therapy, 11:11-27, (2011); Arnould et al., Journal of Molecular Biology, 355:443-58 (2006); Arnould et al., Protein Engineering Design & Selection, 24:27-31 (2011); and Stoddard, Q. Rev. Biophys. 38, 49 (2005); Grizot et al., Nucleic Acids Research, 38:2006-18 (2010).

CRISPR-Cas Nucleases

Recent work has demonstrated that clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis of a simple and highly efficient method for performing genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas9 nuclease from *S. pyogenes* (hereafter simply Cas9) can be guided via simple base pair complementarity between 17-20 nucleotides of an engineered guide RNA (gRNA), e.g., a single guide RNA or crRNA/tracrRNA pair, and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)).

In some embodiments, the present system utilizes a wild type or variant Cas9 protein from *S. pyogenes* or *Staphylococcus aureus*, either as encoded in bacteria or codon-optimized for expression in mammalian cells. The guide RNA is expressed in the cell together with the Cas9. Either the guide RNA or the nuclease, or both, can be expressed transiently or stably in the cell.

TAL Effector Repeat Arrays

TAL effectors of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in U.S. Ser. No. 61/610,212, and Reyon et al., Nature Biotechnology 30, 460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

Zinc Fingers

Zinc finger proteins are DNA-binding proteins that contain one or more zinc fingers, independently folded zinc-containing mini-domains, the structure of which is well known in the art and defined in, for example, Miller et al., 1985, EMBO J., 4:1609; Berg, 1988, Proc. Natl. Acad. Sci. USA, 85:99; Lee et al., 1989, Science. 245:635; and Klug, 1993, Gene, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, Science, 252:809; Elrod-Erickson et al., 1998, Structure, 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, Gene 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, Gene Ther., 15:1463-68; Cathomen, 2008, Mol. Ther., 16:1200-07; Wu et al., 2007, Cell. Mol. Life Sci., 64:2933-44).

One existing method for engineering zinc finger arrays, known as "modular assembly," advocates the simple joining together of pre-selected zinc finger modules into arrays (Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277: 3850-56; Bae et al., 2003, Nat. Biotechnol., 21:275-280; Wright et al., 2006, Nat. Protoc., 1:1637-52). Although straightforward enough to be practiced by any researcher, recent reports have demonstrated a high failure rate for this method, particularly in the context of zinc finger nucleases (Ramirez et al., 2008, Nat. Methods, 5:374-375; Kim et al., 2009, Genome Res. 19:1279-88), a limitation that typically necessitates the construction and cell-based testing of very large numbers of zinc finger proteins for any given target gene (Kim et al., 2009, Genome Res. 19:1279-88).

Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

Cells

The methods described herein can be used in any cell that is capable of repairing a DSB in genomic DNA. The two major DSB repair pathways in eukaryotic cells are Homologous recombination (HR) and Non-homologous end joining (NHEJ). Preferably, the methods are performed in cells capable of NHEJ. Methods for detecting NHEJ activity are known in the art; for a review of the NHEJ canonical and alternative pathways, see Liu et al., Nucleic Acids Res. Jun. 1, 2014; 42(10):6106-6127.

Sequencing

As used herein, "sequencing" includes any method of determining the sequence of a nucleic acid. Any method of sequencing can be used in the present methods, including chain terminator (Sanger) sequencing and dye terminator sequencing. In preferred embodiments, Next Generation Sequencing (NGS), a high-throughput sequencing technology that performs thousands or millions of sequencing reactions in parallel, is used. Although the different NGS platforms use varying assay chemistries, they all generate sequence data from a large number of sequencing reactions run simultaneously on a large number of templates. Typically, the sequence data is collected using a scanner, and then assembled and analyzed bioinformatically. Thus, the sequencing reactions are performed, read, assembled, and analyzed in parallel; see, e.g., US 20140162897, as well as Voelkerding et al., Clinical Chem., 55: 641-658, 2009; and MacLean et al., Nature Rev. Microbiol., 7: 287-296 (2009). Some NGS methods require template amplification and some that do not. Amplification-requiring methods include pyrosequencing (see, e.g., U.S. Pat. Nos. 6,210,89 and 6,258,568; commercialized by Roche); the Solexa/Illumina platform (see, e.g., U.S. Pat. Nos. 6,833,246, 7,115,400, and 6,969,488); and the Supported Oligonucleotide Ligation and Detection (SOLiD) platform (Applied Biosystems; see, e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476,503). See, e.g., US 20130274147; US20140038831; Metzker, Nat Rev Genet 11(1): 31-46 (2010).

Alternatively, hybridization-based sequence methods or other high-throughput methods can also be used, e.g., microarray analysis, NANOSTRING, ILLUMINA, or other sequencing platforms.

EXAMPLES

The invention is further described in the following examples, which do not limit the scope of the invention described in the claims.

Example 1

Figure 1B:
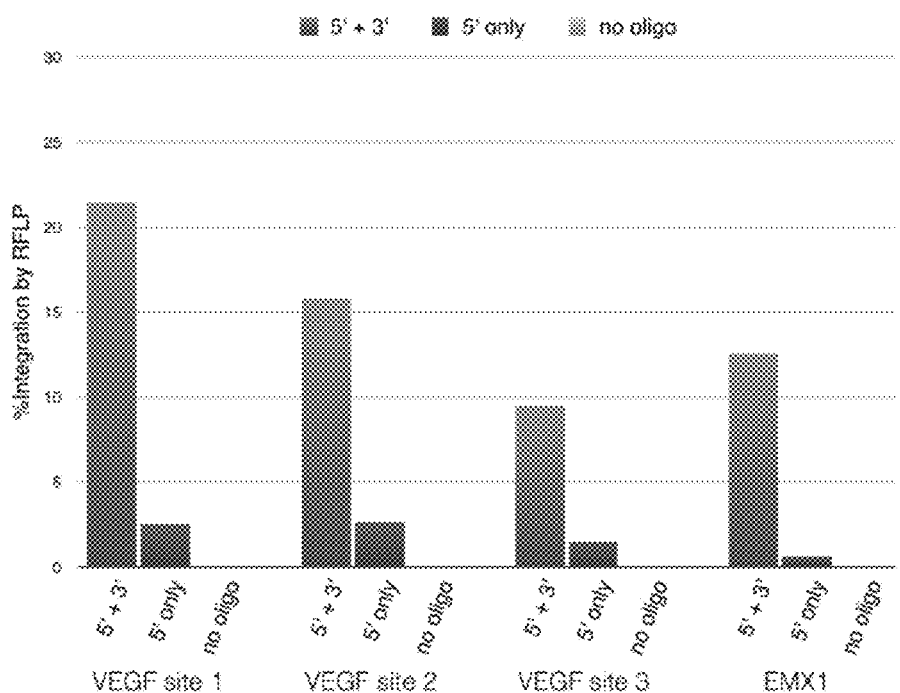
Figure 2A:
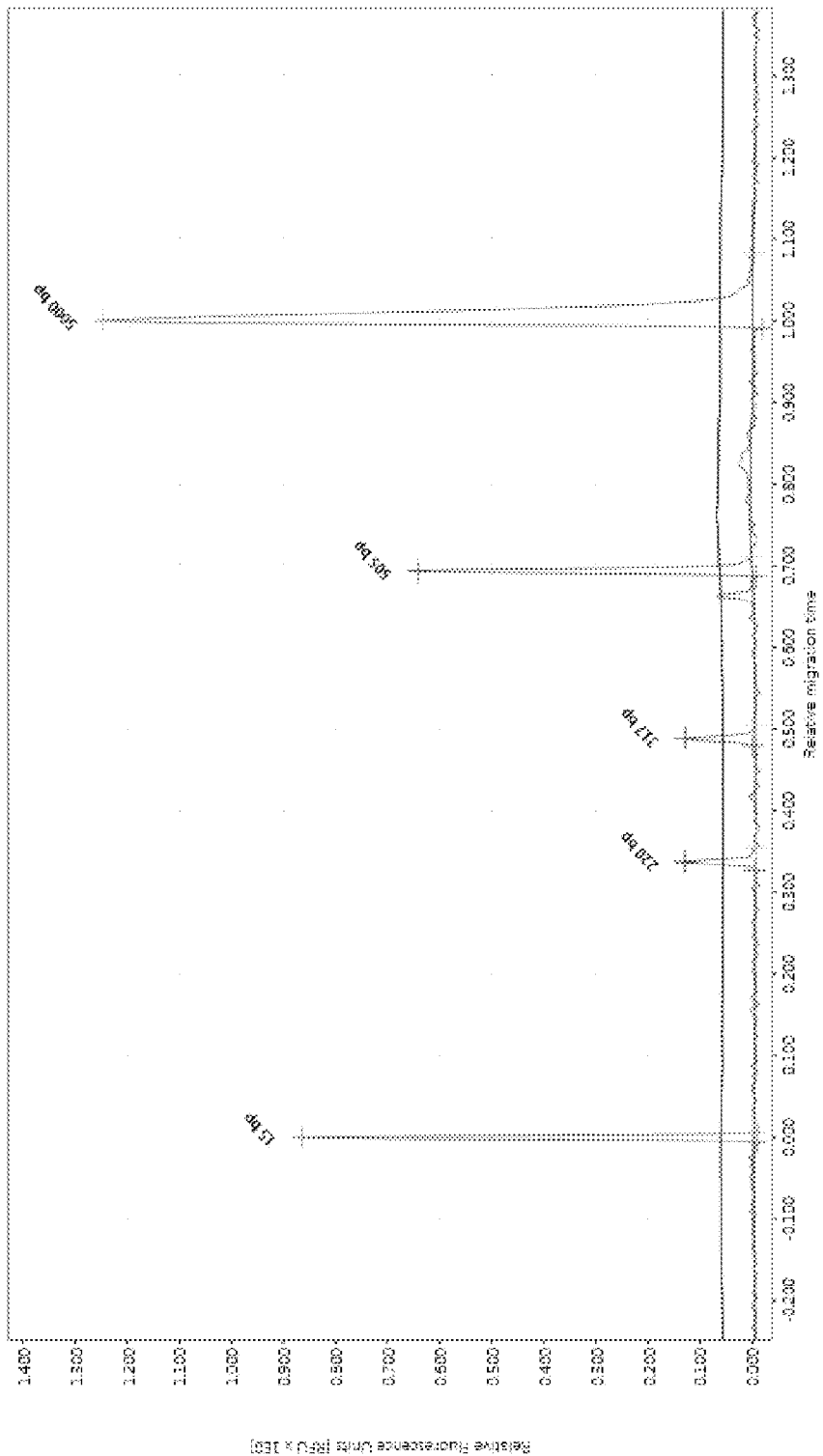
Figure 2B:
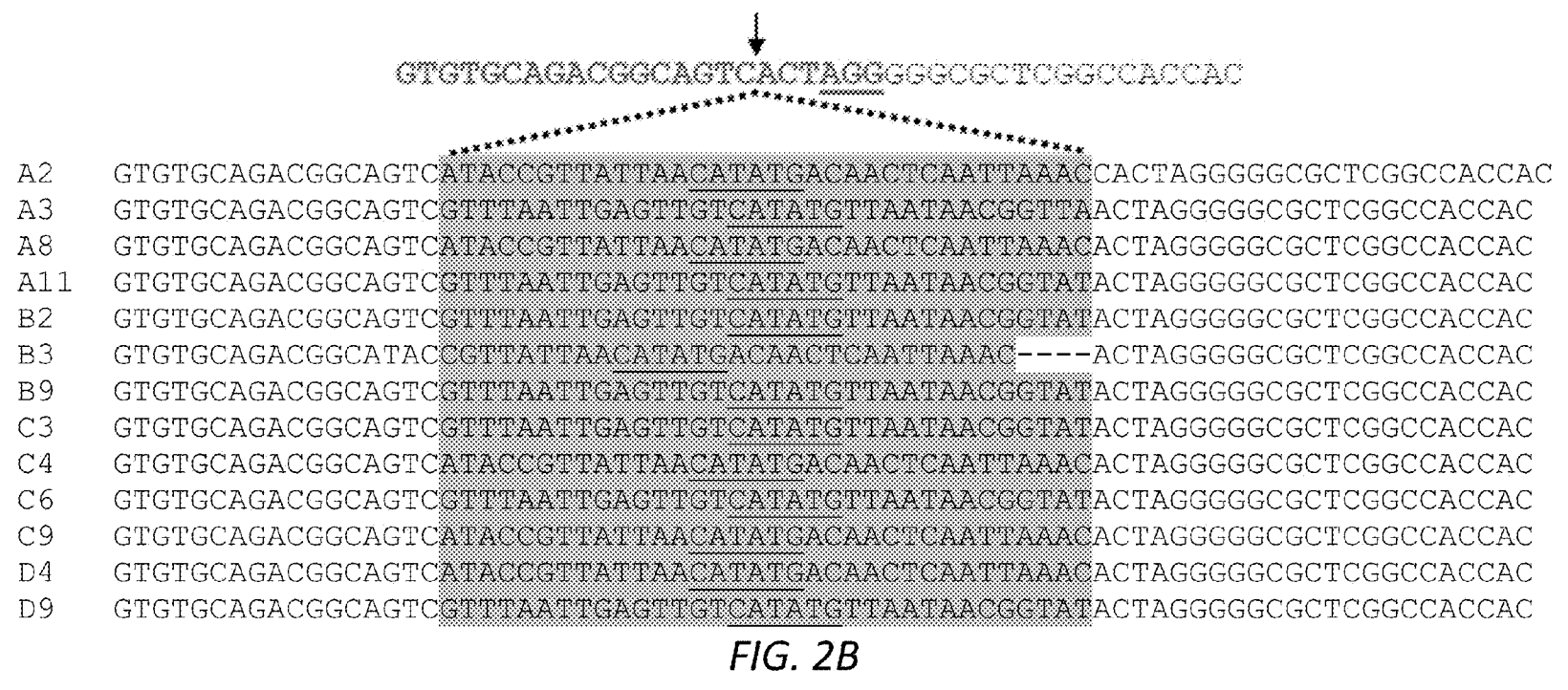

In initial experiments, the process of integrating a dsODN cassette into nuclease-induced double-stranded breaks (DSBs) was optimized. Previously published experiments had demonstrated that dsODNs bearing two phosphorothiorate linkage modifications at their 5' ends could be captured into a zinc finger nuclease (ZFN)-induced DSB in mammalian cells (Orlando et al., Nucleic Acids Res. 2010 August; 38(15):e152). However, to use the capture of such ssODNs to identify even very low frequency DSBs, the characteristics of the dsODN were optimized to improve its rate of capture into such breaks. Initial efforts were focused on capture of the dsODN into DSBs induced by the Clustered Regularly Interspaced Short Palindromic Repeat (CRISPR) RNA-guided nuclease Cas9 from *Streptococcus pyogenes*. Cas9 has been reported to induce DSBs with blunt ends and therefore dsODN variants were designed that were blunt-ended. Optimization experiments showed that the phosphorylation of both 5' ends and the introduction of two phosphorothioate linkages on both 3' ends (in addition to the ones on the 5' ends) led to substantially increased rate of capture of a dsODN into a Cas9-induced DSB (FIGS. 1A-B). Sanger sequencing verified the successful capture of the dsODN into this particular DSB (FIGS. 2A-B).

Having established that dsODNs can be efficiently integrated into Cas9-induced DSBs, the next experiments sought to determine whether next-generation deep sequencing methods could be used to capture, amplify and identify the sites of dsODN integrations in the genomes of mammalian cells. To do this, a 34 bp dsODN was utilized that contains two PCR primer binding sites (one on each strand); these sequences were chosen because they are each orthogonal to the human genome.

The sequence of the dsODN used is provided in Table 1:

TABLE 1

| Strand | Sequence (5' to 3') | SEQ ID NO: |
|---|---|---|
| FWD | /5Phos/G*T*TTAATTGAGTTGTCATATGTTAATAACGGT*A*T | 1 |
| REV | /5Phos/A*T*ACCGTTATTAACATATGACAACTCAATTAA*A*C | 2 |

/5Phos/ denotes 5' phosphorylation.
*denotes phosphorothioate linkage between adjacent nucleotides.

This dsODN was transfected into human U2OS cells together with plasmids encoding Cas9 and one of four different target-specific gRNAs, each targeted to a different endogenous human gene sequence (EMC1 and VEGFA sites 1, 2, and 3). These four particular gRNAs were chosen because bona fide off-target sites had been previously identified for each of them (Fu et al., Nat Biotechnol. 2013; Table 1). The transfections were performed as follows: dsODN is annealed in STE (100 mM TrisHcl, 500 mM NaCl, 10 mM EDTA) at a concentration of 100 uM each. For U2OS cells, 500 ng of Cas9 expression plasmid, 250 ng gRNA expression plasmid, and 100 pmol of dsODN were used to nucleofect 2E5 cells with solution SE and program DN-100.

Genomic DNA was harvested three days post-transfection (Agencourt AMPURE XP automated PCR purification system) and a PCR-based restriction fragment length polymorphisms (RFLP) assay was used to verify that the dsODN had been efficiently integrated into the on-target site in these cells based on the presence of a restriction site encoded in the dsODN.

Figure 3:
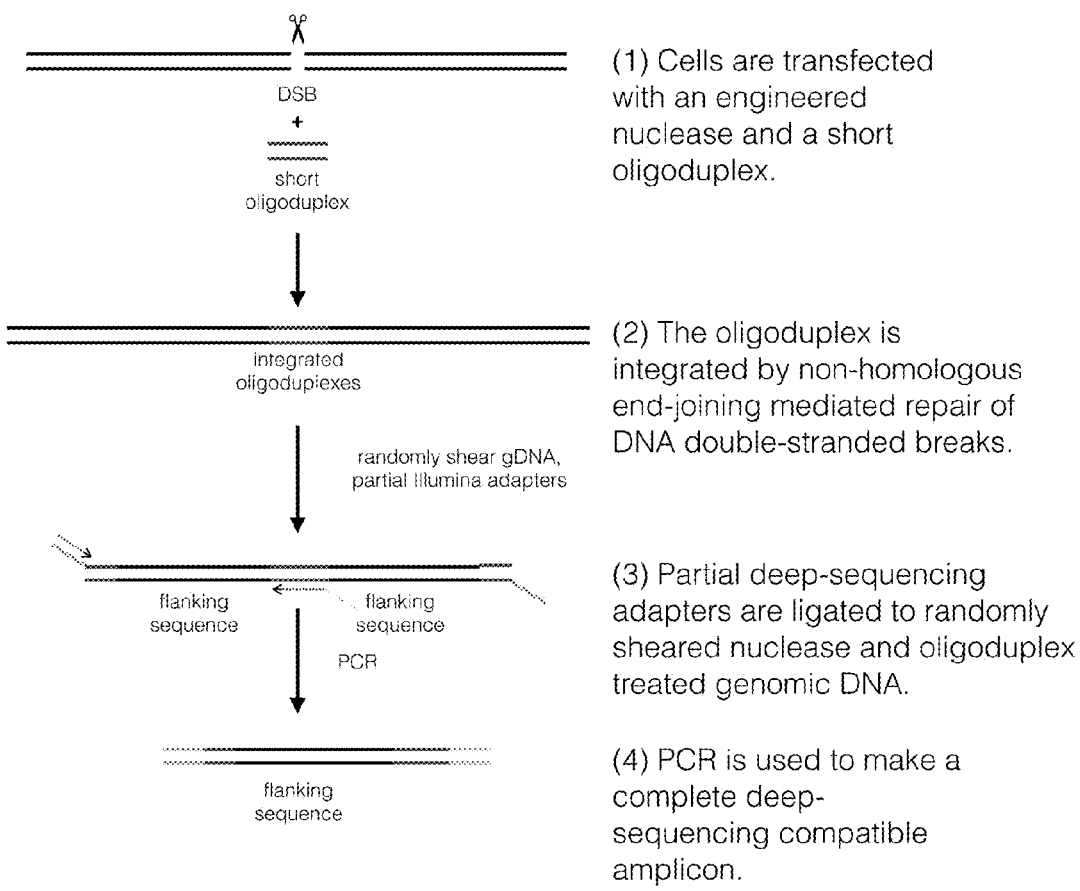
FIG. 3. Overview of exemplary GUIDE-seq method.
Figure 4A:
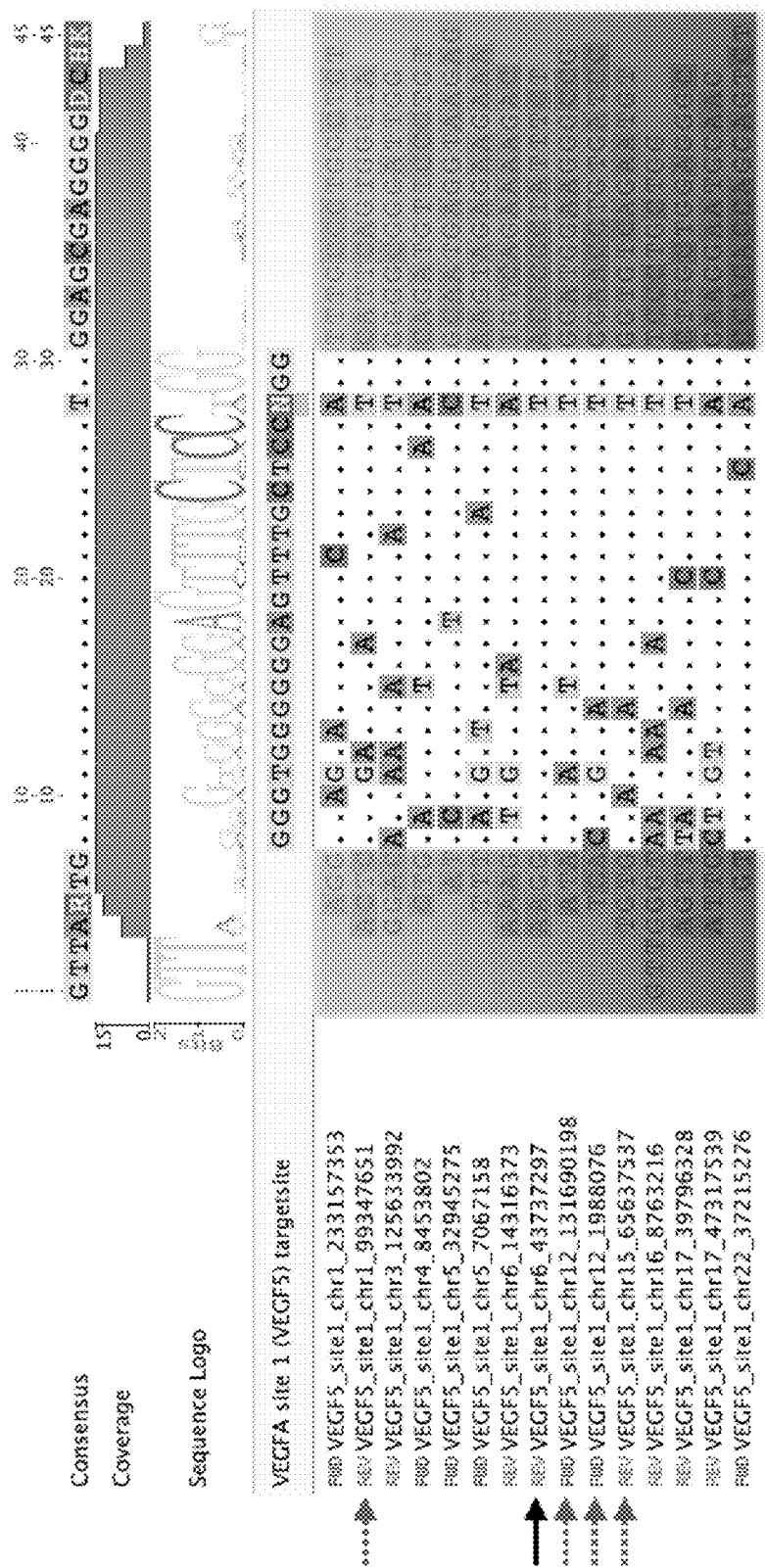
FIGS. 4A-E. CRISPR-Cas off-target cleavage sites discovered by GUIDE-Seq method. Data is shown for four sites, VEGF sites 1-3 (VEGF Site 1: SEQ ID NOS 37 and 104-118, respectively, in order of appearance; VEGF Site 2: SEQ ID NOS 38 and 119-220, respectively, in order of appearance; VEGF Site 3: SEQ ID NOS 39 and 221-260, respectively, in order of appearance), and EMX1 (EMX1: SEQ ID NOS 36 and 261-272, respectively, in order of appearance). Mismatches to the target site sequence are highlighted. A small solid black arrow is used to indicate the intended on-target site, while a small dashed arrow is used to mark known off-target sites that had been detected in an earlier study (Fu et al., 2013).
Figure 4B:
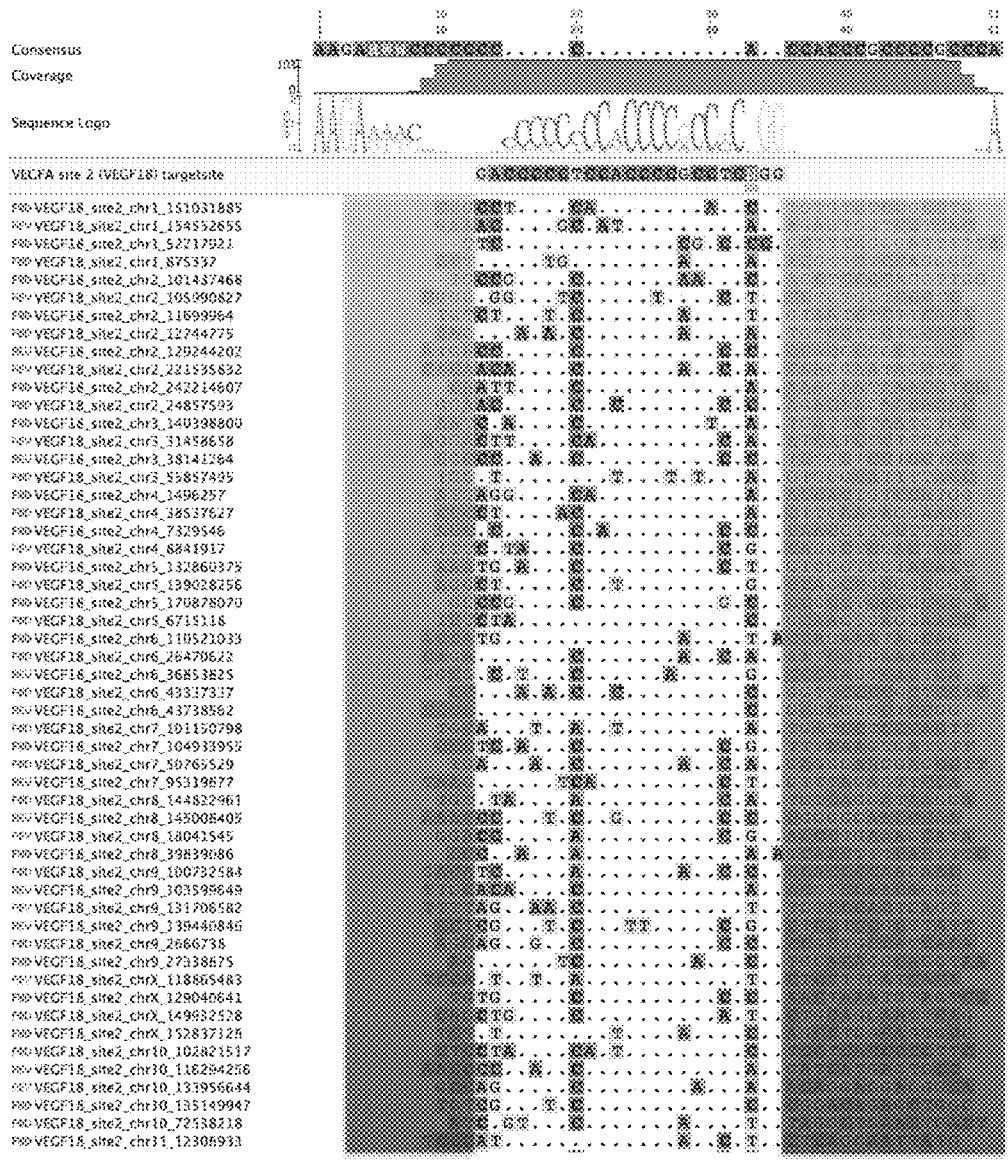
Figure 4C:
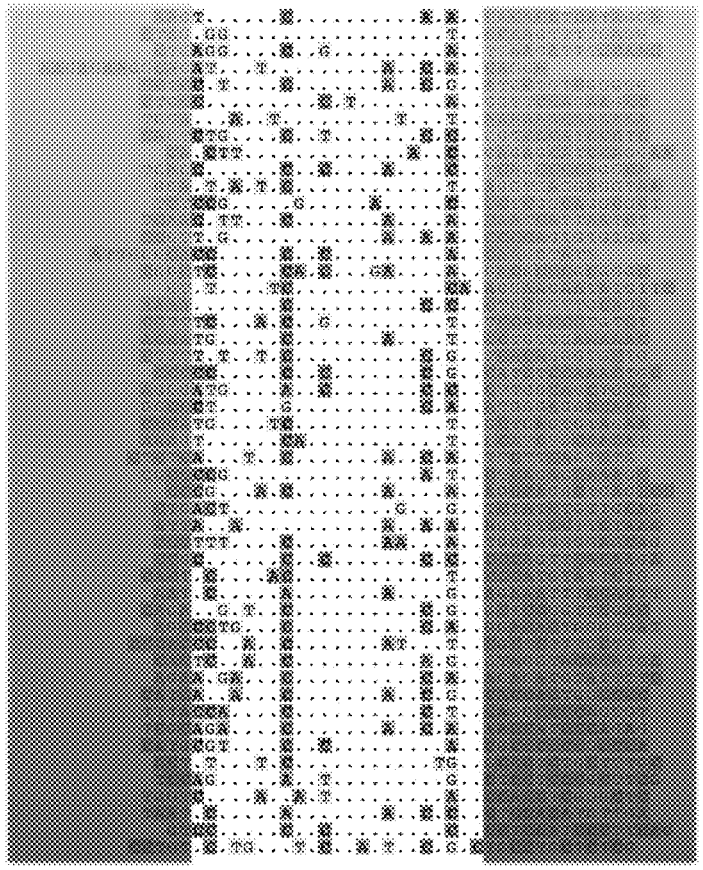
Figure 4D:
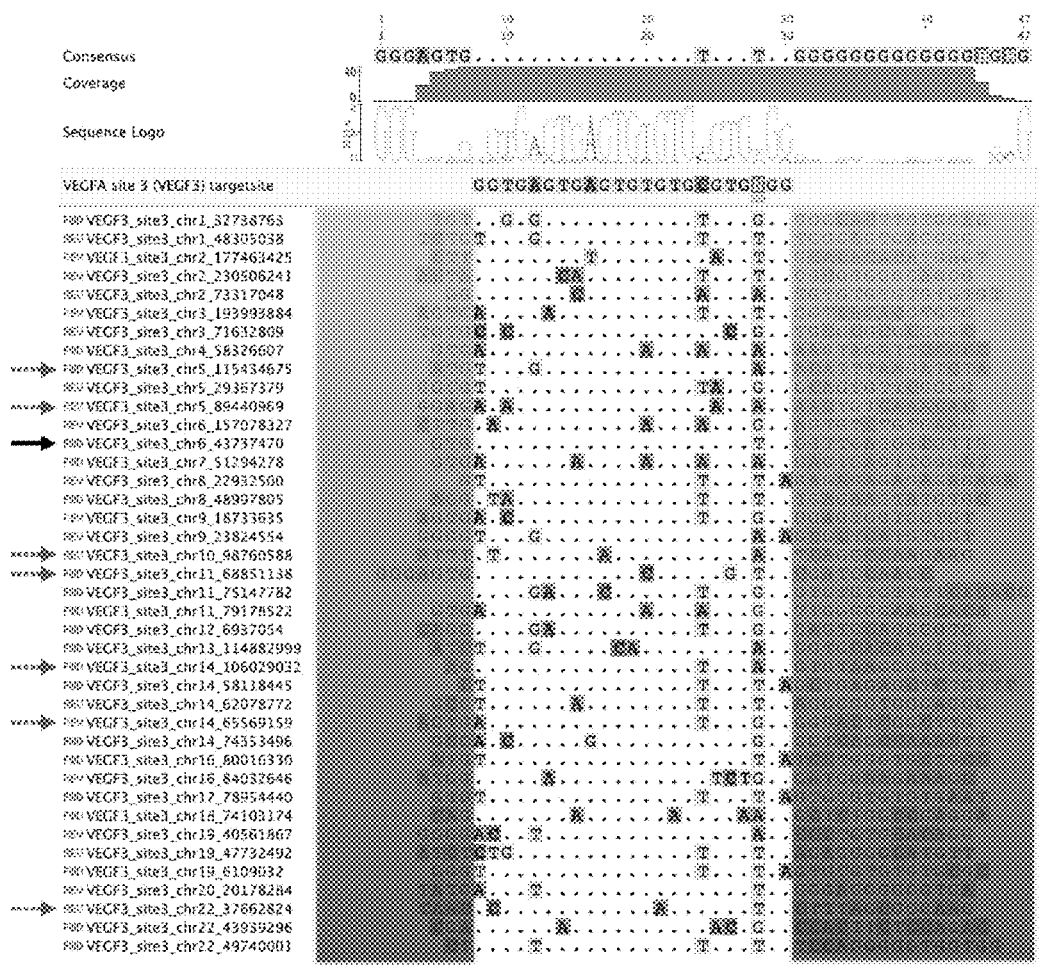
Figure 4E:
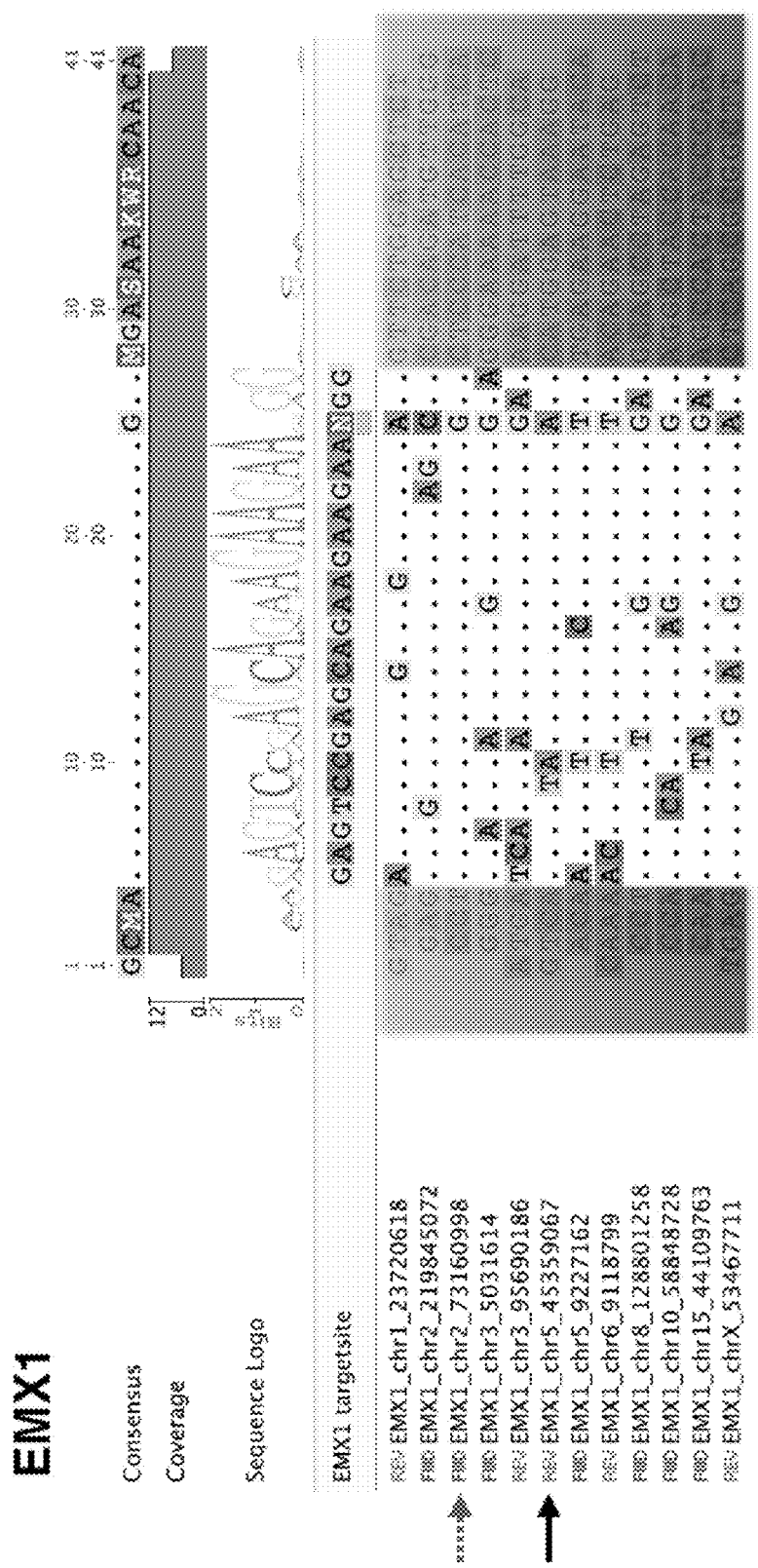

To comprehensively identify the locations of dsODN integration in the genomes of the transfected cells, a PCR-based method was used that selectively amplifies these insertion sites and also enables them to be sequenced using next-generation sequencing technology. A general overview of the strategy is shown in FIG. 3. Genomic DNA was sheared with a Covaris Adaptive Focused Acoustic (AFA) focused ultrasonicator to a mean length of 500 bp. Sheared gDNA was end-repaired (Enzymatics), A-tailed (Enzymatics), and a half-functional sequencing adapter (US 20130303461) was ligated (Enzymatics) to the ends of the sheared DNA. Solid Phase Reversible Immobilization (SPRI) magnetic bead cleanup was used to clean up each of these enzymatic steps (Agencourt XP).

DNA fragments bearing the dsODN sequence were then amplified using a primer specific to the dsODN together with a primer that anneals to the sequencing adapter. Because there are two potential priming sites within the dsODN (one on each strand as noted above), two independent PCR reactions were performed to selectively amplify the desired sequences as follows.

Two rounds of nested PCR were performed to generate a targeted sequencing library. The first round of PCR was performed using a primer complementary to the integration dsODN (primer A) and a primer complementary to the universal adapter (primer B). The second round of PCR was performed using a 3' nested primer complementary to primer A (primer C), a 3' nested primer complementary to primer B (primer D), and a primer that was complementary to primer D (primer E) that added a flow-cell binding sequence and random molecular index to make a 'complete' molecule that was ready for sequencing. SPRI magnetic beads were used to clean up each round of PCR. (Agencourt AMPURE XP automated PCR purification system).

The amplification of dsODN-containing genomic sequences by this approach neither depends on nor is biased by flanking sequence adjacent to the insertion point because the sequencing adapter is ligated to breaks induced by random sharing of genomic DNA. An additional round of PCR was performed to add next-generation sequencing adapter sequences and an indexing barcode on the end closest to the dsODN, resulting in a library of fragments that is ready for next-generation sequencing. This general method is referred to herein as GUIDE-Seq, for Genome-wide Unbiased Identification of DSBs Evaluated by Sequencing.

Deep sequencing of the libraries constructed using GUIDE-Seq revealed a wide range of genomic loci into which the dsODN had become inserted in the presence of each of the four co-expressed gRNA/Cas9 nucleases. In analyzing the raw deep sequencing data, it was reasoned that bona fide sites of insertion could be identified as genomic loci that were covered by at least one read in both orientations. Reads in both directions were possible both because the dsODN could insert in either orientation and because amplifications were performed using primers specific for either one or the other strand in the dsODN sequence. A total of 465 genomic loci were identified that met this criterion for the four gRNAs examined. For 36% of these 465 loci a sequence within 25 bps of the insertion point was also identified that was similar to the on-target site of the gRNA used and bearing as many as six mismatches relative to the on-target site (FIGS. 4A-E). This method also successfully discovered all previously known bona fide off-target sites for all four gRNAs examined here (all of the previously known off-target sites shown in FIG. 4 are also present in Table 1 from Fu et al., Nat Biotechnol. 2013) as well as many additional previously unknown off-target sites.

Example 2

Customizable CRISPR-Cas RNA-guided nucleases (RGNs) are robust, customizable genome-editing reagents with a broad range of research and potential clinical applications[1, 2]; however, therapeutic use of RGNs in humans will require full knowledge of their off-target effects to minimize the risk of deleterious outcomes. DNA cleavage by S. pyogenes Cas9 nuclease is directed by a programmable ~100 nt guide RNA (gRNA).[3] Targeting is mediated by 17-20 nts at the gRNA 5'-end, which are complementary to a "protospacer" DNA site that lies next to a protospacer adjacent motif (PAM) of the form 5'-NGG. Repair of Cas9-induced DNA double-stranded breaks (DSBs) within the protospacer by non-homologous end-joining (NHEJ) can induce variable-length insertion/deletion mutations (indels). Our group and others have previously shown that unintended RGN-induced indels can occur at off-target cleavage sites that differ by as many as five positions within the protospacer or that harbor alternative PAM sequences[4-7]. Chromosomal translocations can result from joining of on- and off-target RGN-induced cleavage events[8-11]. For clinical applications, identification of even low frequency alterations will be critically important because ex vivo and in vivo therapeutic strategies using RGNs are expected to require the modification of very large cell populations. The induction of oncogenic transformation in even a rare subset of cell clones (e.g., inactivating mutations of a tumor suppressor gene or formation of a tumorigenic chromosomal translocation) is of particular concern because such an alteration could lead to unfavorable clinical outcomes.

The comprehensive identification of indels or higher-order genomic rearrangements that can occur anywhere in the genome is a challenge that is not easily addressed, and unfortunately sensitive methods for unbiased, genome-wide identification of RGN-induced off-target mutations in living cells have not yet been described[12, 13]. Whole genome re-sequencing has been used to attempt to identify RGN off-target alterations in edited single cell clones[14, 15] but the high cost of sequencing very large numbers of genomes makes this method impractical for finding low frequency events in cell populations[12]. We and others have used focused deep sequencing to identify indel mutations at potential off-target sites identified either by sequence similarity to the on-target site[4, 5] or by in vitro selection from partially degenerate binding site libraries[6]. However, these approaches make assumptions about the nature of off-target sequences and therefore may miss other mutation sites elsewhere in the genome. ChIP-Seq has also been used to identify off-target binding sites for gRNAs complexed with catalytically dead Cas9 (dCas9), but the majority of published work suggests that very few, if any, of these sites represent off-target sites of cleavage by active Cas9 nuclease[16-19].

Here we describe the development of a novel method for Genome-wide Unbiased Identification of DSBs Evaluated by Sequencing (GUIDE-Seq), which enabled us to generate the first global specificity landscapes for ten different RGNs in living human cells. These profiles revealed that the total number of off-target DSBs varied widely for individual RGNs and suggested that broad conclusions about the specificity of RGNs from S. pyogenes or other species should be based on large surveys and not on just small numbers of gRNAs. Our findings also expanded the range and nature of sequences at which off-target effects can occur. Direct comparisons demonstrated that GUIDE-Seq substantially outperformed two widely used computational approaches and a ChIP-Seq method for identifying RGN off-target sites. Unexpectedly, GUIDE-Seq also identified RGN-independent DNA breakpoint hotspots that can participate together with RGN-induced DSBs in higher-order genomic alterations such as translocations. Lastly, we show in direct comparisons that truncating the complementarity region of gRNAs greatly improved their genome-wide off-target DSB profiles, demonstrating the utility of GUIDE-Seq for evaluating advances designed to improve RGN specificities. The experiments outlined here provide the most rigorous strategy described to date for evaluating the specificities of RGNs, as well as of any improvements to the platform, that may be considered for therapeutic use.

Methods

The following materials and methods were used in this Example.

Human Cell Culture and Transfection

U2OS and HEK293 cells were cultured in Advanced DMEM (Life Technologies) supplemented with 10% FBS, 2 mM GLUTAMAX media supplement (Life Technologies), and penicillin/streptomycin at 37° C. with 5% $CO_2$. U2OS cells (program DN-100) and HEK293 cells (program CM-137) were transfected in 20 µl Solution SE on a Lonza NUCLEOFECTOR 4-D transfection system according to the manufacturer's instructions. dsODN integration rates were assessed by restriction fragment length polymorphism (RFLP) assay using NdeI. Cleavage products were run and quantified by a QIAXCEL capillary electrophoresis instrument (Qiagen) as previously described (Tsai et al., Nat. Biotechnol 32, 569-576 (2014)).

Isolation and Preparation of Genomic DNA for GUIDE-Seq

Genomic DNA was isolated using solid-phase reversible immobilization magnetic beads (Agencourt DNAdvance), sheared with a Covaris S200 sonicator to an average length of 500 bp, end-repaired, A-tailed, and ligated to half-functional adapters, incorporating a 8-nt random molecular index. Two rounds of nested anchored PCR, with primers complementary to the oligo tag, were used for target enrichment. Full details of the exemplary GUIDE-Seq protocol can be found herein.

Processing and Consolidation of Sequencing Reads

Reads that share the same six first bases of sequence as well as identical 8-nt molecular indexes were binned together because they are assumed to originate from the same original pre-PCR template fragment. These reads were consolidated into a single consensus read by selecting the majority base at each position. A no-call (N) base was assigned in situations with greater than 10% discordant reads. The base quality score was taken to be the highest among the pre-consolidation reads. Consolidated reads were mapped to human genome reference (GrCh37) using BWA-MEM (Li and Durbin, Bioinformatics 26, 589-595 (2010)).

Identification of Off-Target Cleavage Sites

Start mapping positions for reads with mapping quality ≥50 were tabulated, and regions with nearby start mapping positions were grouped using a 10-bp sliding window. Genomic windows harboring integrated dsODNs were identified by one of the following criteria: 1) two or more unique molecular-indexed reads mapping to opposite strands in the reference sequence or 2) two or more unique molecular-indexed reads amplified by forward and reverse primers. 25 bp of reference sequence flanking both sides of the inferred breakpoints were aligned to the intended target site and RGN off-target sites with eight or fewer mismatches from the intended target sequence were called. SNPs and indels were called in these positions by a custom bin-consensus variant-calling algorithm based on molecular index and SAMtools, and off-target sequences that differed from the reference sequence were replaced with the corresponding cell-specific sequence.

AMP-Based Sequencing

For AMP validation of GUIDE-Seq detected DSBs, primers were designed to regions flanking inferred double-stranded breakpoints as described previously (Zheng, Z. et al. Anchored multiplex PCR for targeted next-generation sequencing. Nat Med 2014 Nov. 10. doi: 10.1038/nm.3729 (2014)), with the addition of an 8-nt molecular index. Where possible, we designed two primers to flank each DSB.

Analysis of AMP Validation Data

Reads with average quality scores >30 were analyzed for insertions, deletions, and integrations that overlapped with the GUIDE-Seq inferred DSB positions using Python. 1-bp indels were included only if they were within 1-bp of the predicted DSB site to minimize the introduction of noise from PCR or sequencing error. Integration and indel frequencies were calculated on the basis of consolidated molecular indexed reads.

Structural Variation

Translocations, large deletions, and inversions were identified using a custom algorithm based on split BWA-MEM alignments. Candidate fusion breakpoints within 50 bases on the same chromosome were grouped to accommodate potential resection around the Cas9 cleavage site. A fusion event was called with at least 3 uniquely mapped split reads, a parameter also used by the segemehl tool (Hoffmann, Genome biology, 2014)). Mapping strandedness was maintained for identification of reciprocal fusions between two involving DSBs, and for determining deletion or inversion. Fusions involved DSBs within 1 kb chromosomal positions were discarded for consideration of large indels caused by single Cas9 cleavage. Remaining fusion DSBs were classified in four categories: 'on-target', 'off-targe' or 'background' based on GUIDE-seq or, else, 'other'.

Comparison of Sites Detected by GUIDE-Seq and ChIP-Seq and in Silico Predictions We used the MIT CRISPR Design Tool to identify potential off-target sites for all ten RGNs. This tool assigns each potential off-target site a corresponding percentile. We then grouped these percentiles into quintiles for visualization purposes. Because the E-CRISP tool does not rank off-targets, we simply found the GUIDE-seq off-targets that were correctly predicted by E-CRISP. For both of these GUIDE-Seq vs. in silico predictions, we also split the GUIDE-Seq results that were not predicted by the in silico method into off-targets that have mismatch numbers within the range of the MIT tool (maximum of 4) and E-CRISPR (maximum of 3), and those with mismatch numbers greater than the threshold of these prediction tools. In comparing the GUIDE-Seq off-targets with ChIP-Seq predictions, the same technique was used to find the GUIDE-Seq off-targets correctly predicted by the ChIP-Seq. For each of these comparisons, every grouping that was made was subdivided by off-target mismatch number to better characterize the properties of correctly and incorrectly predicted RGN off-targets.

Analysis of Impact of Mismatches, DNA Accessibility and Local PAM Density on Off-Target Cleavage Rate We assessed the impact of mismatch position, mismatch type and DNA accessibility on specificity using linear regression models fit to estimated cleavage rates at potential off-target sites with four or less mismatches. Mismatch position covariates were defined as the number of mis-matched bases within each of five non-overlapping 4-bp windows upstream of the PAM. Mismatch type covariates were defined as i) the number mismatches resulting in wobble pairing (target T replaced by C, target G replaced by A), ii) the number of mismatches resulting in a non-wobble purine-pyrimidine base-pairing (target C replaced by T, target A replaced by G), and iii) the number as mismatches resulting in purine-purine or pyrimidine-pyrimidine pairings.

Each of the three factors was used in separate model as a predictor of relative cleavage rates, estimated by $\log_2(1+$ GUIDE-Seq read count). The effect size estimates were adjusted for inter-target site variability. The proportion of intra-site cleavage rate variability explained by each factor was assessed by the partial eta-squared statistic based on the regression sums of squares (SS): $\eta^2_p = SS_{factor}/(SS_{factor} + SS_{error})$. In addition to the single-factor models, we also fit a combined linear regression model including all three factors, expression level, and PAM density in a 1-kb window to assess their independent contribution to off-target cleavage probability.

Exemplary Reagents and Equipment for Guide-Seq Library Preparation

| Item | Vendor |
| --- | --- |
| Store at Room Temperature | |
| Covaris S220 microTube, | Covaris |
| Ethanol, 200-proof (100%) | Sigma Aldrich |
| MICROAMP Optical 96-well Plates | Applied Biosystems |
| Nuclease-free H$_2$O | Promega |
| QUBIT fluorometric quantitation Assay Tubes, 500 tubes/pack | Invitrogen |
| QUBIT fluorometric quantitation dsDNA BR Kit - 500 Assays | Invitrogen |
| TMAC Buffer, 5M Tetramethylammonium Chloride | Sigma Aldrich |

| | |
|---|---|
| 1X TE Buffer/10 mM Tris-HCl, pH 8.0 | Invitrogen |
| UltraPure 0.5M EDTA, pH 8.0 (Gibco) (4 × 100 mL) | Life Technologies |
| Store at 4° C. | |
| Agencourt AMPURE XP Beads- 60 mL | Beckman Coulter |
| Item | Catalog # |
| Store at −20° C. | |
| 25 mM dNTP Solution Mix | Enzymatics, Inc. |
| Slow ligation buffer | Enzymatics, Inc. |
| End-repair mix (low concentration) | Enzymatics, Inc. |
| T4 DNA Ligase | Enzymatics, Inc. |
| 10X T4 DNA Ligase Buffer (Slow Ligation Buffer) | |
| Platinum ® Taq DNA Polymerase | Life Technologies |
| 10X PCR Buffer (no MgCl$_2$) | |
| 50 mM MgCl$_2$ | |
| qPCR Illumina Library Quantification Kits | KAPA Biosystems, Inc. |
| Equipment | |
| 96-well Plate Magnetic Stand | Invitrogen |
| QUBIT Fluorometer 2.0 | Life Technologies |
| Covaris S-2 Focused Ultra-sonicator ™ Instrument | Covaris |
| Tabletop centrifuge | Thermo Scientific |
| Tabletop vortexer | Thermo Scientific |
| Thermocycler | Eppendorf |
| MISEQ genome sequencer | Illumina |

Exemplary Protocol for GUIDE-Seq Library Preparation

Y-Adapter Preparation

The Y-adapter is made by annealing the MISEQ genome sequencer common oligo with each of the sample barcode adapters (A01 to A16, see Table 4). The adapters also contain 8-mer NNWNNWNN (N=A, C, T, or G; W=A or T) molecular indexes.

| | |
|---|---|
| 1X TE Buffer | 80.0 µL |
| A## (100 µM) | 10.0 µL |
| MISEQ genome sequencer Common Adapter_MI (100 µM) | 10.0 µL |
| Total | 100.0 µL |

Annealing program: 95° C. for 1 s; 60° C. for 1 s; slow ramp down (approximately −2° C./min) to 4° C.; hold at 4° C. Store in −20° C.

Input Quantification and Shearing 1. dsDNA is quantified by QUBIT fluorometric quantitation and 400 ng is brought to a final volume of 120 ul using 1× TE Buffer.
2. Each sample is sheared to an average length of 500 bp according to the standard operating protocol for the Covaris S2.
3. A cleanup with 120 ul of AMPURE XP SPRI PCR purification beads (1× ratio) is performed according to manufacturer protocol, and eluted in 15 ul of 1×TE Buffer.

End Repair, A-Tailing and Ligation

End Repair

4. To a 200 µL PCR tube or well in a 96-well plate, add the following (per reaction):

| | |
|---|---|
| Nuclease-free H$_2$O | 0.5 µL |
| dNTP mix, 5 mM | 1.0 µL |
| SLOW Ligation Buffer, 10X | 2.5 µL |
| End-repair mix (low concentration) | 2.0 µL |
| Buffer for Taq Polymerase, 10X (Mg2 + free) | 2.0 µL |
| Taq Polymerase (non-hot start) | 0.5 µL |
| Total | 8.5 µL |
| +DNA sample (from previous step) | 14.0 µL |
| Total | 22.5 µL |

End Repair Thermocycler Program: 12° C. for 15 min, 37° C. for 15 min; 72° C. for 15 min; hold at 4° C.

Adapter Ligation

5. To the sample reaction tube or well, add the following reagents in order (mix by pipetting):

| | |
|---|---|
| Annealed Y adapter_MI (10 µM) | 1.0 µL |
| T4 DNA Ligase | 2.0 µL |
| +DNA sample (from previous step) | 22.5 µL |
| Total | 25.5 µL |

Adapter Ligation Thermocycler Program: 16° C. for 30 min, 22° C. for 30 min, hold at 4° C.

6. 0.9×SPRI clean (22.95 ul AMPURE XP PCR purification beads), elute in 12 uL of 1×TE buffer.

PCRs

PCR 1 (Oligo Tag Primer [Discovery] or Large Primer Pool [Deep-Sequencing Validation])

7. Prepare the following master mix:

| | |
|---|---|
| Nuclease-free H$_2$O | 11.9 µL |
| Buffer for Taq Polymerase, 10X (MgCl$_2$ free) | 3.0 µL |
| dNTP mix, 10 mM | 0.6 µL |
| MgCl$_2$, 50 mM | 1.2 µL |
| Platinum Taq polymerase, 5 U/µl | 0.3 µL |
| GSP1 Primer (10 uM)/Primer Pool (*) | 1.0 µL* |
| TMAC (0.5M) | 1.5 µL |
| P5_1, 10 µM | 0.5 µL |
| Total | 20.0 µL |
| +DNA sample (from Step 6) | 10.0 µL |
| Total | 30.0 µL |

*For Discovery, make separate master mixes for +/(sense) and −/(antisense) reactions, and proceed with separate PCR reactions.
*For deep-sequencing validation, one master mix can be made. Primer Pool should be normalized to a total amount of 30 pmol in the 30 ul reaction.

Discovery Thermocycler Program (touchdown):

95° C. for 5 min, 15 cycles of [95° C. for 30 s, 70° C. (−1° C./cycle) for 2 min, 72° C. for 30 s], 10 cycles of [95° C. for 30 s, 55° C. for 1 min, 72° C. for 30 s], 72° C. for 5 min, 4° C. hold Validation Thermocycler Program:

95° C. for 5 min, 14 cycles of [95° C. for 30 s, 20% ramping down to 65° C., 65° C. for 5 min], 72° C. for 5 min, 4° C. hold 8. 1.2×SPRI clean (36.0 uL), elute in 15 ul of 1×TE Buffer.

PCR 2 (Oligo Tag Primer [Discovery] or Large Primer Pool [Deep-Sequencing Validation])

9. Prepare the following master mix:

| | |
|---|---|
| Nuclease-free H$_2$O | 5.4 μL |
| Buffer for Taq Polymerase, 10X (Mg$^{2+}$ free) | 3.0 μL |
| dNTP mix, 10 mM | 0.6 μL |
| MgCl$_2$, 50 mM | 1.2 μL |
| Platinum Taq polymerase, 5 U/μl | 0.3 μL |
| GSP2 Primer (10 uM)/Primer Pool(*) | 1.0 μL |
| TMAC (0.5M) | 1.5 μL |
| P5_2, 10 μM | 0.5 μL |
| Total | 13.5 μL |
| +P7_# (10 uM)* | 1.5 μL |
| +DNA sample with beads (from Step 8) | 15.0 μL |
| Total | 30.0 μL |

Primer concentrations should follow the specifications described in PCR1
*For the P7_#, at least 4 should be used in one sequencing run for good image registration on Illumina sequencer (e.g. P701-P704 or P705-P708)

Discovery Thermocycler Program (touchdown):
same as for PCR1
Validation Thermocycler Program:
same as for PCR1
10. 0.7×SPRI clean (21.0 uL), elute in 30 ul of 1×TE Buffer.
Library Quantification by qPCR and Sequencing
qPCR Quantification
11. Quantitate library using Kapa Biosystems kit for Illumina Library Quantification kit, according to manufacturer instruction.

Normalization and Sequencing
12. Using the mean quantity estimate of number of molecules per uL given by the qPCR run for each sample, proceed to normalize the total set of libraries to 1.2×10^10 molecules, divided by the number of libraries to be pooled together for sequencing. This will give a by molecule input for each sample, and also a by volume input for each sample.
After pooling, dry down the library with a VACUFUGE vacuum concentrator to a final volume of 10 uL for sequencing.
Denature the library and load onto the MISEQ genome sequencer according to Illumina's standard protocol for sequencing with an Illumina MISEQ genome sequencer Reagent Kit V2-300 cycle (2×150 bp paired end), except:
1) Add 3 ul of 100 μM custom sequencing primer Index 1 to MISEQ genome sequencer Reagent cartridge position 13 (Index Primer Mix). Add 3 ul of 100 μM custom sequencing primer Read 2 to MISEQ genome sequencer Reagent cartridge position 14 (Read 2 Primer Mix).
2) Sequence with the following number of cycles "151|8|16|151" with the paired-end Nextera sequencing protocol.
Submit sequencing data in either bcl or fastq format to relevant pipelines for downstream bioinformatics analysis.

TABLE 3

Common Primers Needed for GUIDE-Seq

| P7 Adapters | Sequence (5'→3') | SEQ ID NO: |
|---|---|---|
| P701 | CAAGCAGAAGACGGCATACGAGATTCGCCTTAGTGACTGGAGTCCTCTCTATGGGCAGTCGGTGA | 3 |
| P702 | CAAGCAGAAGACGGCATACGAGATCTAGTACGGTGACTGGAGTCCTCTCTATGGGCAGTCGGTGA | 4 |
| P703 | CAAGCAGAAGACGGCATACGAGATTTCTGCCTGTGACTGGAGTCCTCTCTATGGGCAGTCGGTGA | 5 |
| P704 | CAAGCAGAAGACGGCATACGAGATGCTCAGGAGTGACTGGAGTCCTCTCTATGGGCAGTCGGTGA | 6 |
| P705 | CAAGCAGAAGACGGCATACGAGATAGGAGTCCGTGACTGGAGTCCTCTCTATGGGCAGTCGGTGA | 7 |
| P706 | CAAGCAGAAGACGGCATACGAGATCATGCCTAGTGACTGGAGTCCTCTCTATGGGCAGTCGGTGA | 8 |
| P707 | CAAGCAGAAGACGGCATACGAGATGTAGAGAGGTGACTGGAGTCCTCTCTATGGGCAGTCGGTGA | 9 |
| P708 | CAAGCAGAAGACGGCATACGAGATCCTCTCTGGTGACTGGAGTCCTCTCTATGGGCAGTCGGTGA | 10 |
| P5 Adapters | Sequence (5'→3') | |
| P5_1 | AATGATACGGCGACCACCGAGATCTA | 11 |
| P5_2 | AATGATACGGCGACCACCGAGATCTACAC | 12 |
| Custom Sequencing Primers | Sequence (5'→3') | |
| Index1 | ATCACCGACTGCCCATAGAGAGGACTCCAGTCAC | 13 |
| Read2 | GTGACTGGAGTCCTCTCTATGGGCAGTCGGTGAT | 14 |

TABLE 3-continued

Common Primers Needed for GUIDE-Seq

| Illumina Y-adapters 1-16 (with Molecular Index tag NNWNNWNN) | Sequence (5'→3') | |
|---|---|---|
| MISEQ Common Adapter | [Phos]GATCGGAAGAGC*C*A | 15 |
| A01 | AATGATACGGCGACCACCGAGATCTACACTAGATCGCNNWNNWNNACACTCTTTCCCTACACGACGCTCTTCCGATC | 16 |
| A02 | AATGATACGGCGACCACCGAGATCTACACCTCTCTATNNWNNWNNACACTCTTTCCCTACACGACGCTCTTCCGATC*T | 17 |
| A03 | AATGATACGGCGACCACCGAGATCTACACTATCCTCTNNWNNWNNACACTCTTTCCCTACACGACGCTCTTCCGATC*T | 18 |
| A04 | AATGATACGGCGACCACCGAGATCTACACAGAGTAGANNWNNWNNACACTCTTTCCCTACACGACGCTCTTCCGATC*T | 19 |
| A05 | AATGATACGGCGACCACCGAGATCTACACGTAAGGAGNNWNNWNNACACTCTTTCCCTACACGACGCTCTTCCGATC*T | 20 |
| A06 | AATGATACGGCGACCACCGAGATCTACACACTGCATANNWNNWNNACACTCTTTCCCTACACGACGCTCTTCCGATC*T | 21 |
| A07 | AATGATACGGCGACCACCGAGATCTACACAAGGAGTANNWNNWNNACACTCTTTCCCTACACGACGCTCTTCCGATC*T | 22 |
| A08 | AATGATACGGCGACCACCGAGATCTACACCTAAGCCTNNWNNWNNACACTCTTTCCCTACACGACGCTCTTCCGATC*T | 23 |
| A09 | AATGATACGGCGACCACCGAGATCTACACGACATTGTNNWNNWNNACACTCTTTCCCTACACGACGCTCTTCCGATC*T | 24 |
| A10 | AATGATACGGCGACCACCGAGATCTACACACTGATGGNNWNNWNNACACTCTTTCCCTACACGACGCTCTTCCGATC*T | 25 |
| A11 | AATGATACGGCGACCACCGAGATCTACACGTACCTAGNNWNNWNNACACTCTTTCCCTACACGACGCTCTTCCGATC*T | 26 |
| A12 | AATGATACGGCGACCACCGAGATCTACACCAGAGCTANNWNNWNNACACTCTTTCCCTACACGACGCTCTTCCGATC*T | 27 |
| A13 | AATGATACGGCGACCACCGAGATCTACACCATAGTGANNWNNWNNACACTCTTTCCCTACACGACGCTCTTCCGATC*T | 28 |
| A14 | AATGATACGGCGACCACCGAGATCTACACTACCTAGTNNWNNWNNACACTCTTTCCCTACACGACGCTCTTCCGATC*T | 29 |
| A15 | AATGATACGGCGACCACCGAGATCTACACCGCGATATNNWNNWNNACACTCTTTCCCTACACGACGCTCTTCCGATC*T | 30 |
| A16 | AATGATACGGCGACCACCGAGATCTACACTGGATTGTNNWNNWNNACACTCTTTCCCTACACGACGCTCTTCCGATC*T | 31 |

| Primer Name | Sequence (5'→3') | Strand/Direction | |
|---|---|---|---|
| Nuclease_off_+_GSP1 | GGATCTCGACGCTCTCCCTATACCGTTATTAACATATGACA | + | 32 |
| Nuclease_off_-_GSP1 | GGATCTCGACGCTCTCCCTGTTTAATTGAGTTGTCATATGTTAATAAC | - | 33 |
| Nuclease_off_+_GSP2 | CCTCTCTATGGGCAGTCGGTGATACATATGACAACTCAATTAAAC | + | 34 |
| Nuclease_off_-_GSP2 | CCTCTCTATGGGCAGTCGGTGATTTGAGTTGTCATATGTTAATAACGGTA | - | 35 |

*Indicates a Phosphorothioate Bond Modification

RESULTS

Overview of Exemplary GUIDE-Seq Method

In some embodiments, GUIDE-Seq consists of two stages (FIG. 5B): In Stage I, DSBs in the genomes of living human cells are tagged by integration of a blunt double-stranded oligodeoxynucleotide (dsODN) at these breaks. In Stage II, dsODN integration sites in genomic DNA are precisely mapped at the nucleotide level using unbiased amplification and next-generation sequencing.

For Stage I, we optimized conditions to integrate a blunt, 5' phosphorylated dsODN into RGN-induced DSBs in human cells. In initial experiments, we failed to observe integration of such dsODNs into RGN-induced DSBs. Using dsODNs bearing two phosphothiorate linkages at the 5' ends of both DNA strands designed to stabilize the oligos in cells[20], we observed only modest detectable integration frequencies (FIG. 5B). However, addition of phosphothiorate linkages at the 3' ends of both strands led to robust integration efficiencies (FIG. 5B). These rates of integration were only two- to three-fold lower than the frequencies of indels induced by RGNs alone at these sites (i.e., in the absence of the dsODN).

Figure 5A:
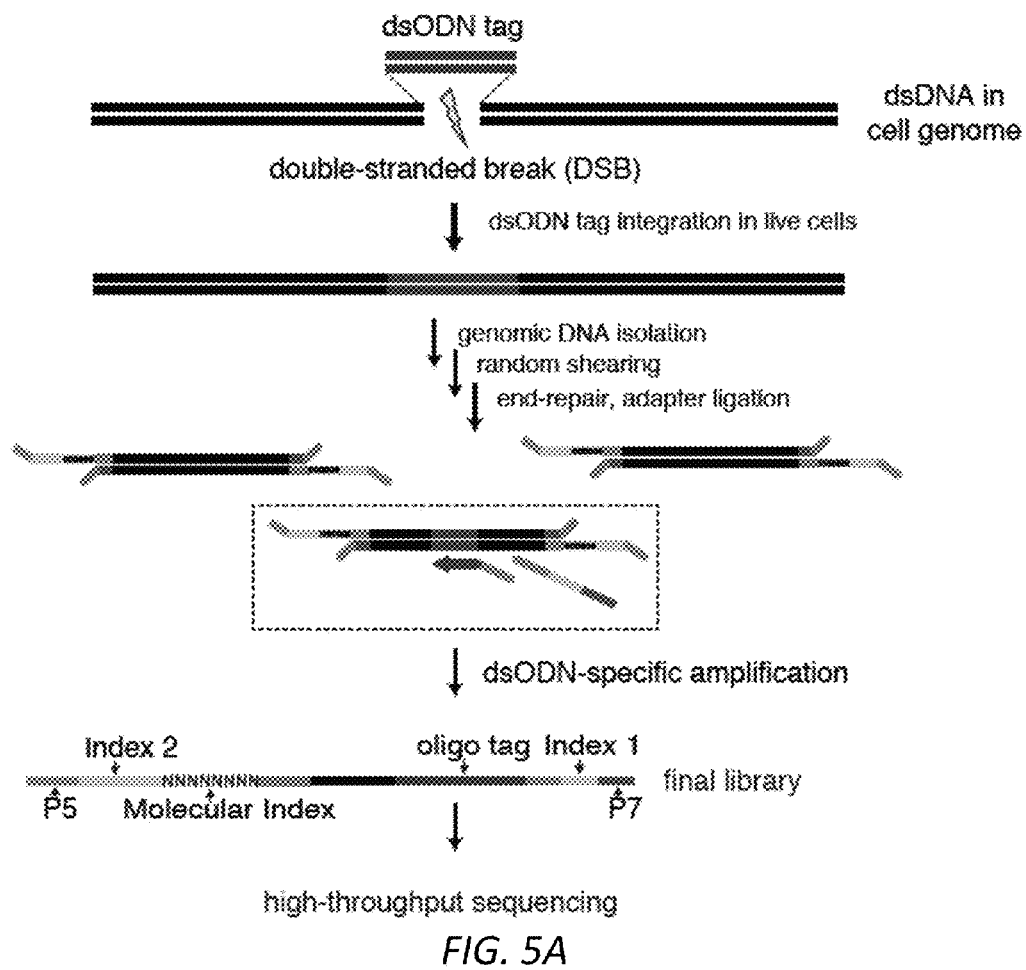
FIGS. 5A-I. Design, optimization and application of an exemplary GUIDE-Seq method.
Figure 5B:
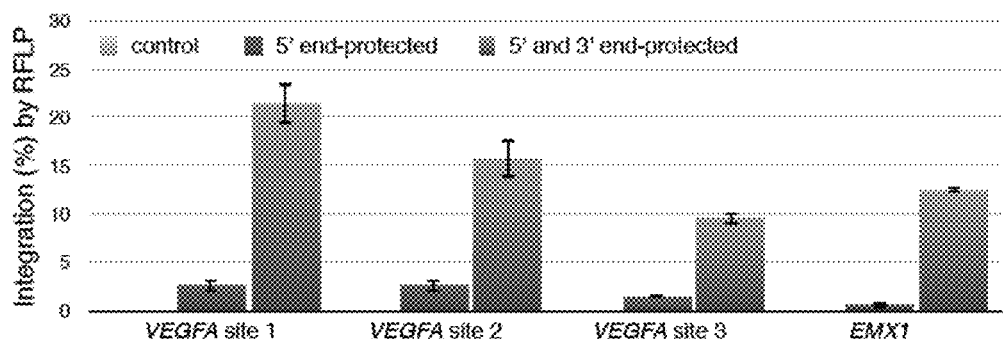
Figure 5C:
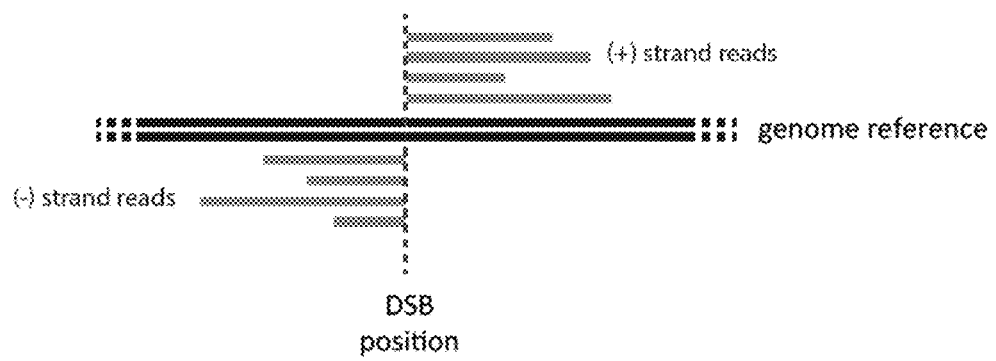

For Stage II, we developed a novel strategy that allowed us to selectively amplify and sequence, in an unbiased fashion, only those fragments bearing an integrated dsODN (FIG. 5A). We accomplished this by first ligating "single-tail" next-generation sequencing adapters to randomly sheared genomic DNA from cells into which dsODN and plasmids encoding RGN components had been transfected. We then performed a series of PCR reactions initiated by one primer that specifically anneals to the dsODN and another that anneals to the sequencing adapter (FIG. 5A and FIG. 12). Because the sequencing adapter is only single-tailed, this enables specific unidirectional amplification of the sequence adjacent to the dsODN, without the bias inherent to other methods such as linear amplification-mediated (LAM)-PCR[21, 22]. We refer to our strategy as the single-tail adapter/tag (STAT)-PCR method. By performing STAT-PCR reactions using primers that anneal to each of the dsODN strands, we could obtain reads of adjacent genomic sequence on both sides of each integrated tag (FIG. 5C). Incorporation of a random 8 bp molecular barcode during the amplification process (FIG. 12) allows for correction of PCR bias, thereby enabling accurate quantitation of unique sequencing reads obtained from high-throughput sequencing.

Genome-Wide Off-Target Cleavage Profiles of CRISPR RGNs in Human Cells

Figure 5D:
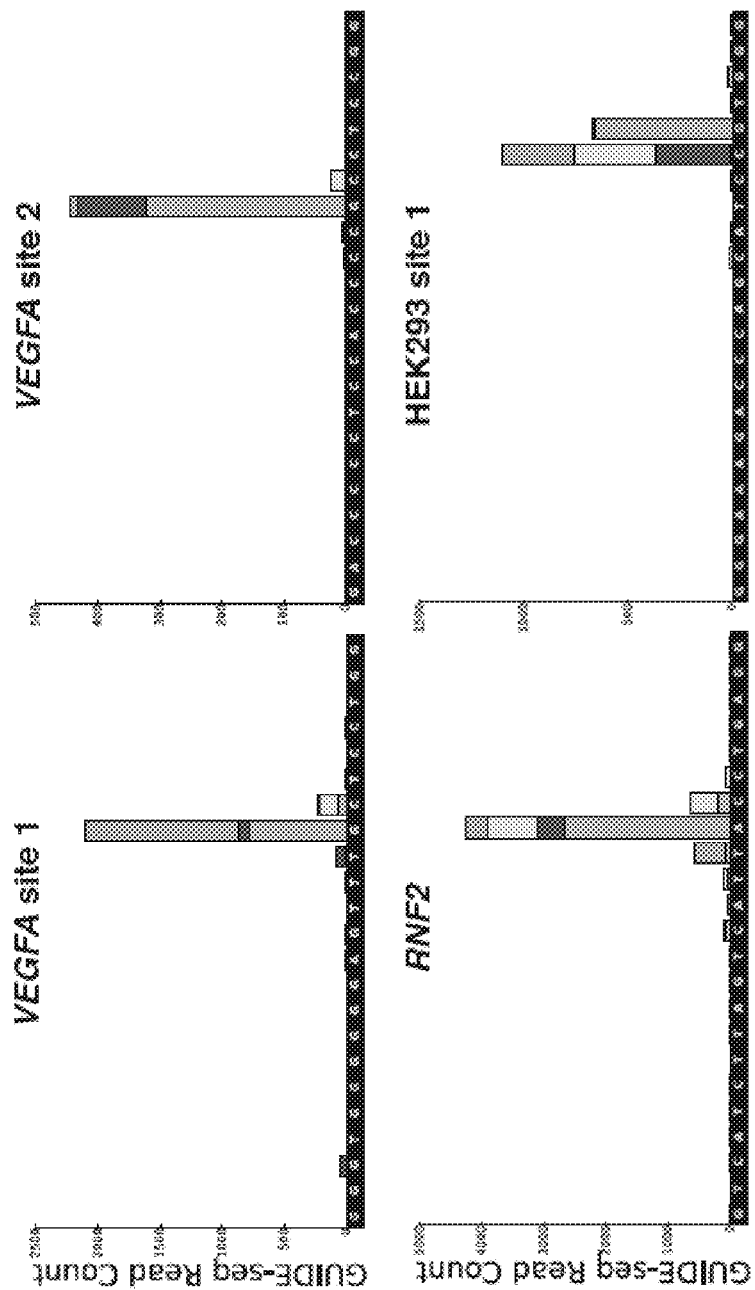
Figure 5D:
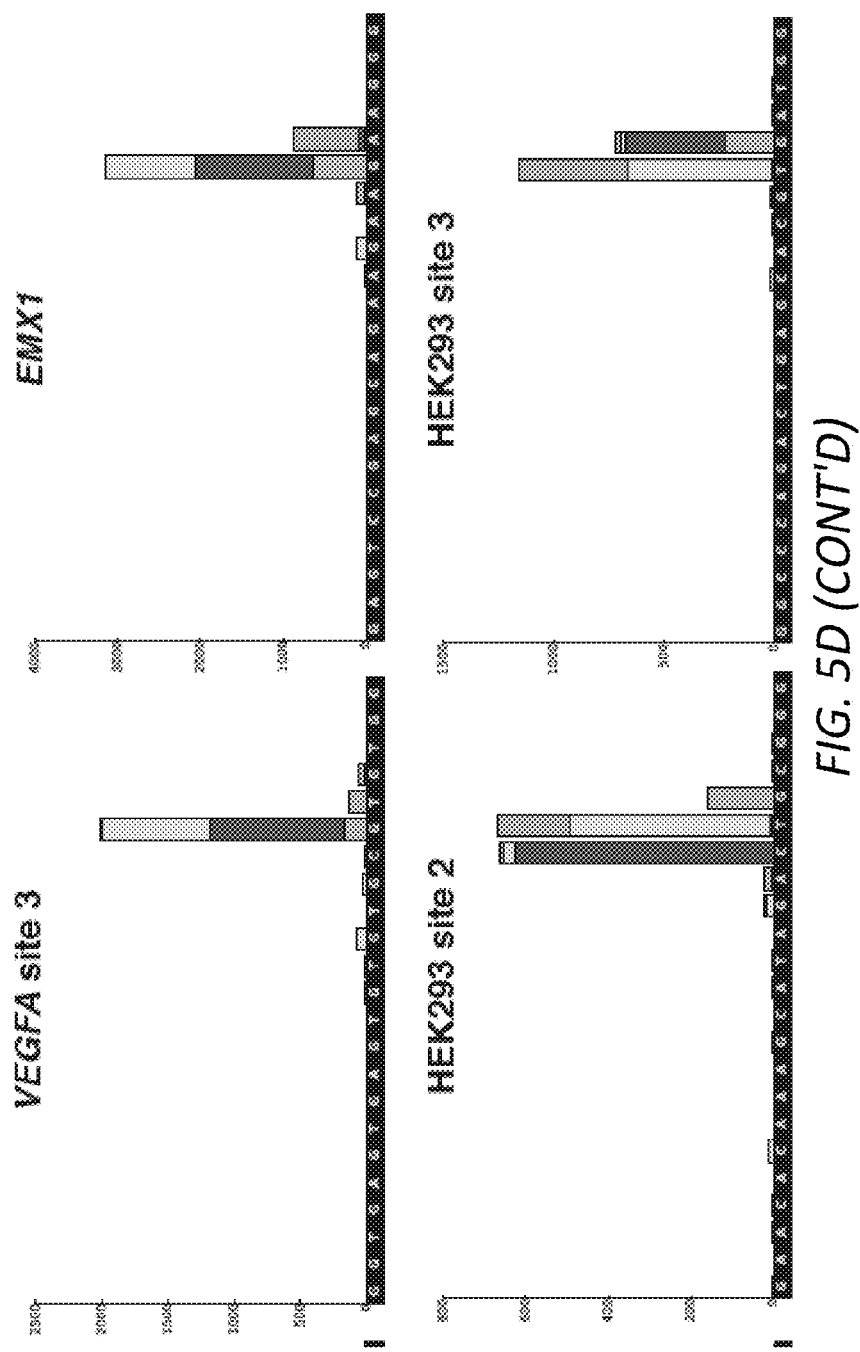
Figure 5D:
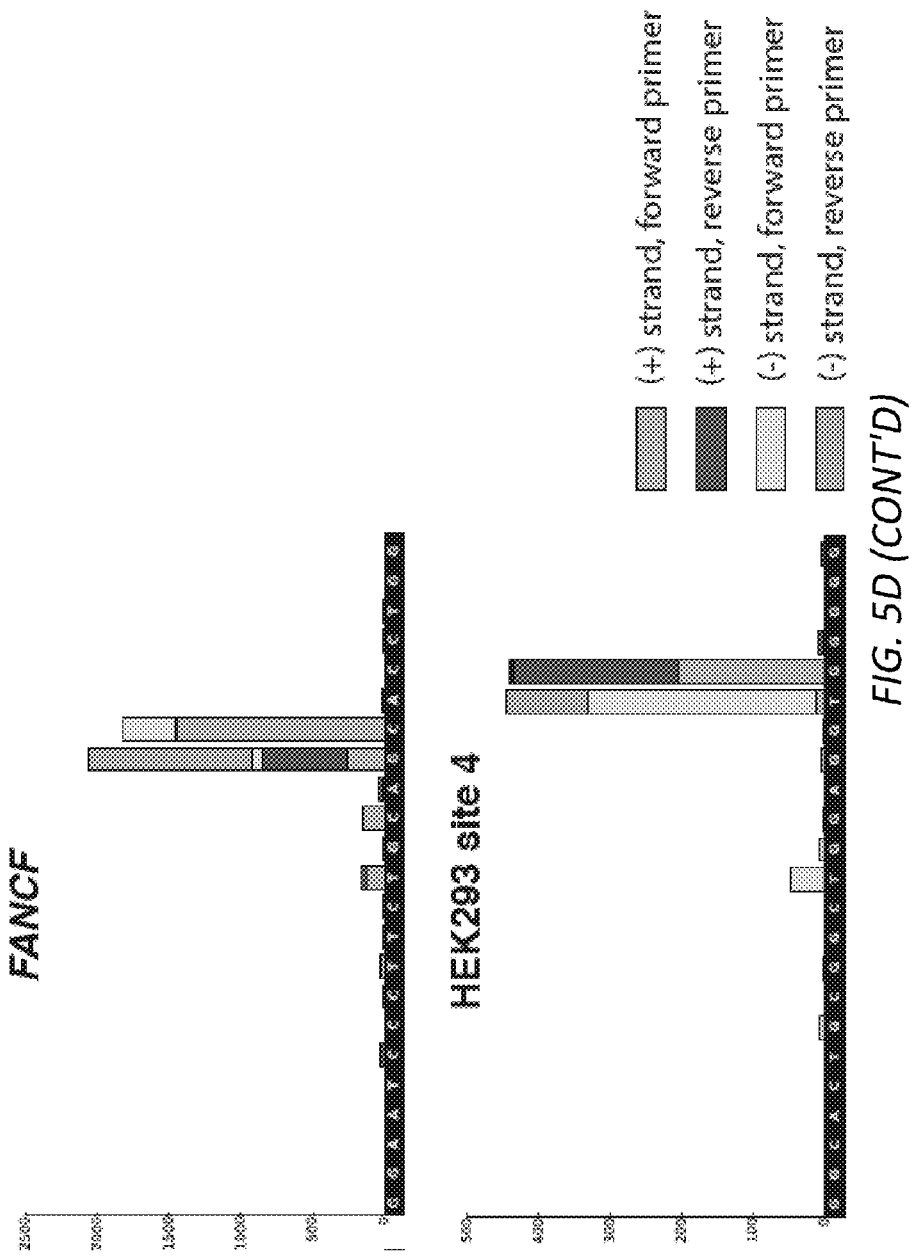
Figure 5E:
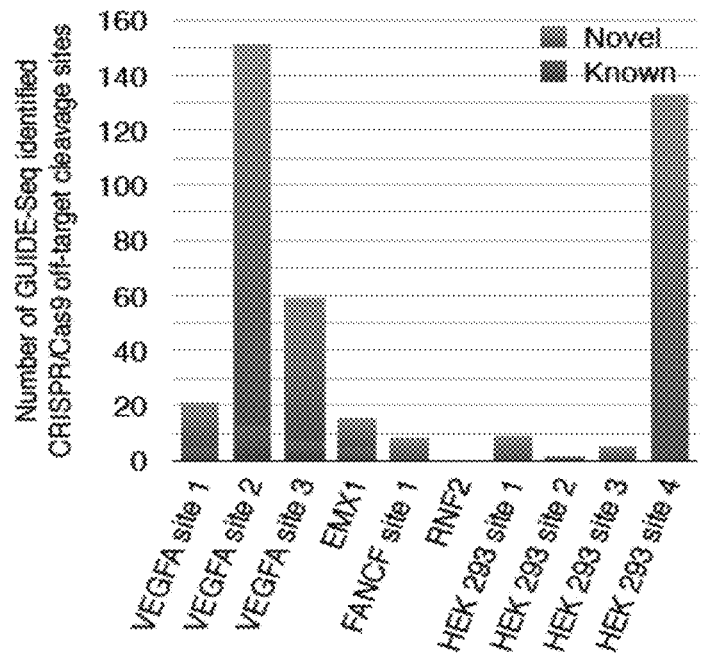
Figure 5F:
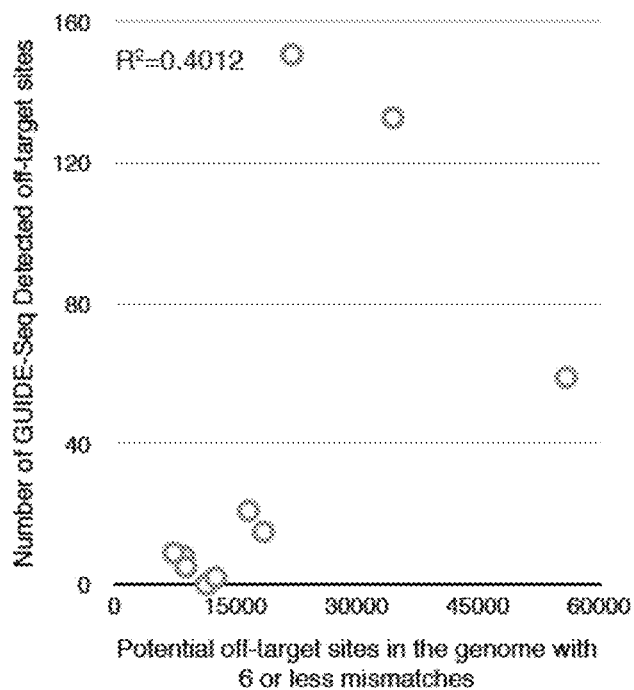
Figure 5G:
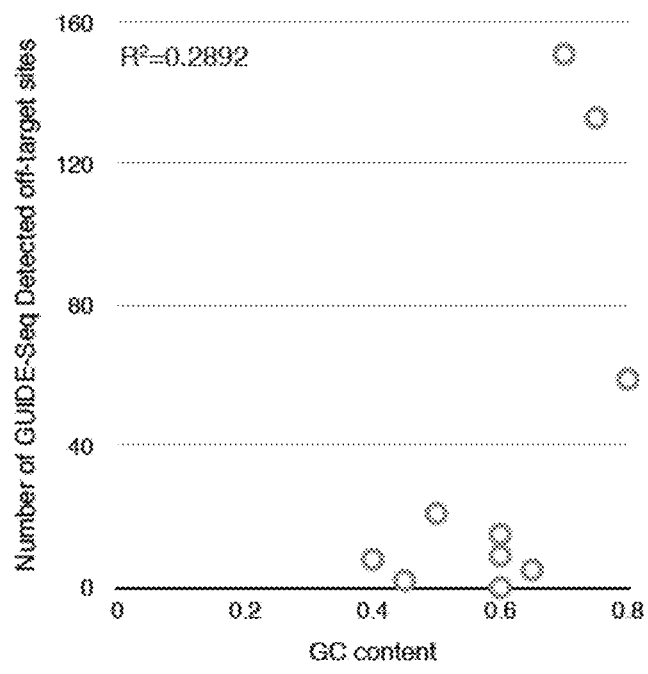
Figures 5H, 5I:
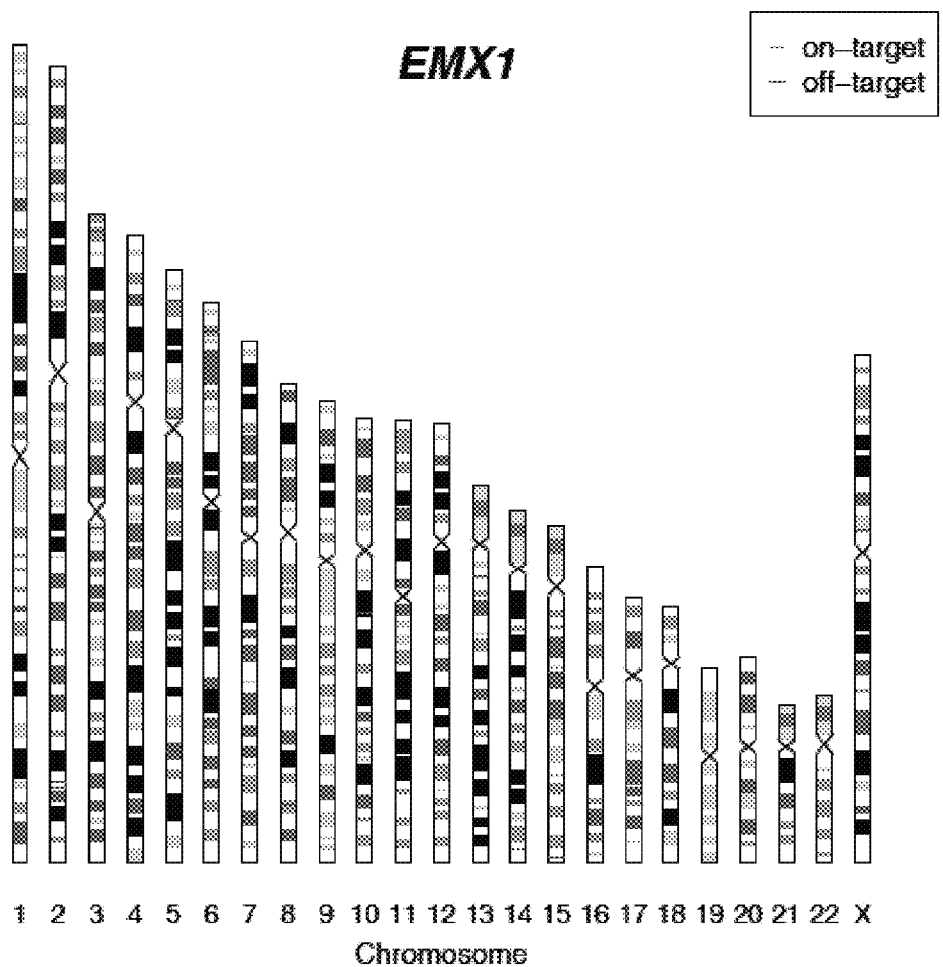
Figure 6A:
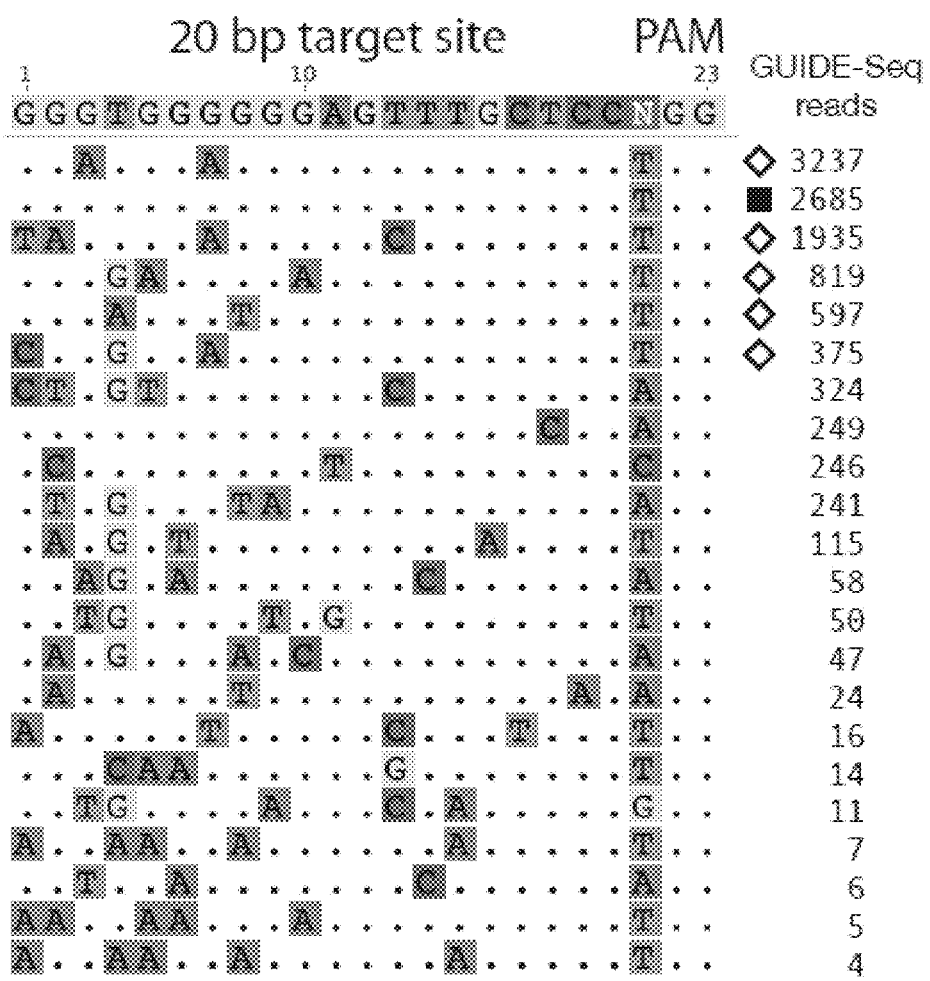
Figure 6B:
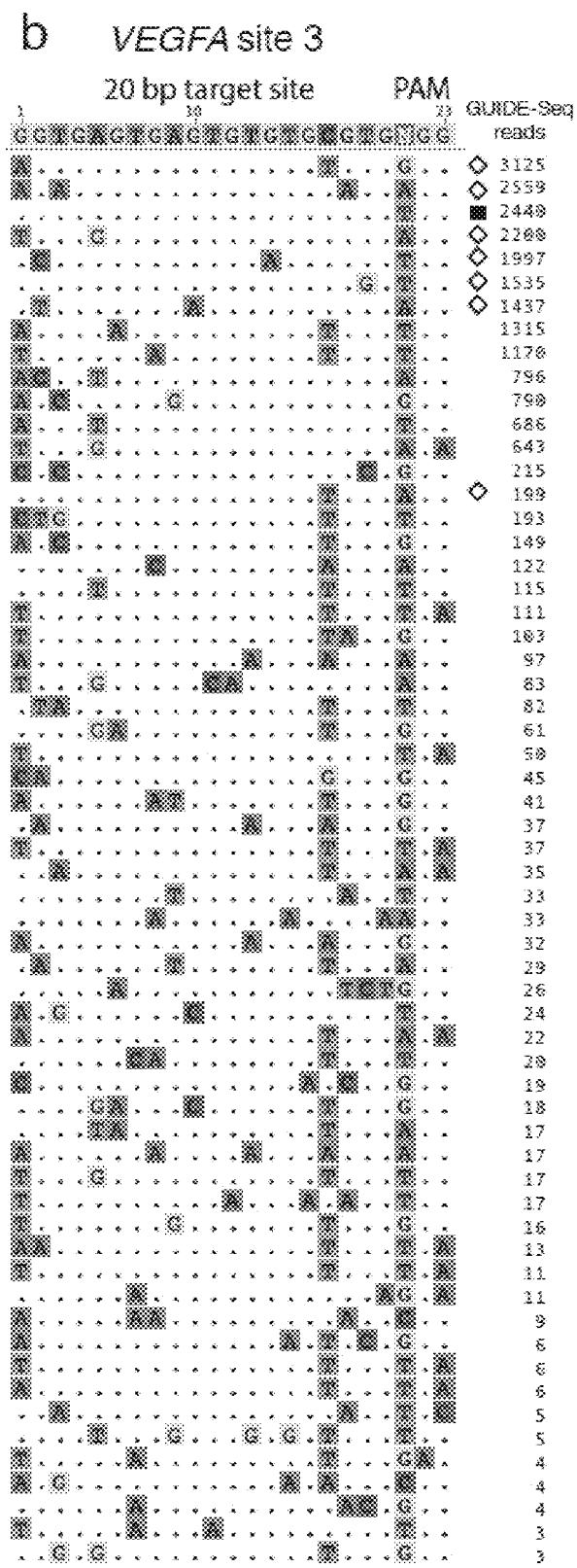

We performed GUIDE-Seq with Cas9 and ten different gRNAs targeted to various endogenous human genes in either U2OS or HEK293 human cell lines (Table 5). By analyzing the dsODN integration sites (Methods), we were able to identify the precise genomic locations of DSBs induced by each of the ten RGNs, mapped to the nucleotide level (FIG. 5D). For >80% of these genomic windows, we were able to identify an overlapping target sequence that either is or is related to the on-target site (Methods). Interestingly, the total number of off-target sites we identified for each RGN varied widely, ranging from zero to >150 (FIG. 5E), demonstrating that the genome-wide extent of unwanted cleavage for any particular RGN can be considerable or minimal on the extremes. We did not observe any obvious correlation between the orthogonality of the gRNA protospacer sequence relative to the human genome (as measured by the total number of genomic sites harboring one to six mismatches) and the total number of off-target sites we observed by GUIDE-Seq (FIG. 5F). Off-target sequences are found dispersed throughout the genome (FIG. 5Gg and FIGS. 13A-J) and fall in exons, introns, and non-coding intergenic regions (FIG. 5H). Included among the off-target sequences we identified were all of the bona fide off-target sites previously known for four of the RGNs[4, 5] (FIGS. 6A-J). More importantly, GUIDE-Seq identified a large number of new, previously unknown off-target sites that map throughout the human genome (FIGS. 5E, 5G. 6A-J and 13A-J).

TABLE 5

| Target site name | Cells | Sequence | SEQ ID NO: |
| --- | --- | --- | --- |
| EMX1 | U2OS | GAGTCCGAGCAGAAGAAGAANGG | 36 |
| VEGFA site1 | U2OS | GGGTGGGGGGAGTTTGCTCCNGG | 37 |
| VEGFA site2 | U2OS | GACCCCCTCCACCCCGCCTCNGG | 38 |
| VEGFA site3 | U2OS | GGTGAGTGAGTGTGTGCGTGNGG | 39 |
| RNF2 | U2OS | GTCATCTTAGTCATTACCTGNGG | 40 |
| FANCF | U2OS | GGAATCCCTTCTGCAGCACCNGG | 41 |
| HEK293 site 1 | 293 | GGGAAAGACCCAGCATCCGTNGG | 42 |
| HEK293 site 2 | 293 | GAACACAAAGCATAGACTGCNGG | 43 |
| HEK293 site 3 | 293 | GGCCCAGACTGAGCACGTGANGG | 44 |
| HEK293 site 4 | 293 | GGCACTGCGGCTGGAGGTGGNGG | 45 |
| truncated VEGFA site 1 | U2OS | GTGGGGGGAGTTTGCTCCNGG | 87 |
| truncated VEGFA site 3 | U2OS | GAGTGAGTGTGTGCGTGNGG | 88 |
| Truncated EMX1 | U2OS | GTCCGAGCAGAAGAAGAANGG | 89 |

We next tested whether the number of sequencing reads for each off-target site identified by GUIDE-Seq (shown in FIGS. 6A-J) represents a proxy for the relative frequency of indels that would be induced by an RGN alone (i.e., in the absence of a dsODN). Examination of these sites by anchored multiplex PCR (AMP)-based next-generation sequencing for five RGNs in human U2OS cells in which nuclease components had been expressed (Methods) showed that >80% (106 out 132) harbored variable-length indels characteristic of RGN cleavage, further supporting our conclusion that GUIDE-Seq identifies bona fide RGN off-target sites (FIG. 7A). The range of indel frequencies detected ranged from 0.03% to 60.1%. Importantly, we observed positive linear correlations between GUIDE-Seq read counts and indel mutation frequencies for all five RGN off-target sites (FIGS. 7A-F). Thus, we conclude that GUIDE-Seq read counts for a given site represent a quantitative measure of the cleavage efficiency of that sequence by an RGN.

Analysis of RGN-Induced Off-Target Sequence Characteristics

Visual inspection of the off-target sites we identified by GUIDE-Seq for all ten RGNs underscores the diversity of variant sequences at which RGNs can cleave. These sites can harbor as many as six mismatches within the protospacer sequence (consistent with a previous report showing in vitro cleavage of sites bearing up to seven mismatches[6]), non-canonical PAMs (previously described NAG and NGA sequences[5, 23] but also novel NAA, NGT, NGC, and NCG sequences), and 1 bp "bulge"-type mismatches[24] at the gRNA/protospacer interface (FIG. 6A-J). Protospacer mismatches tend to occur in the 5' end of the target site but can also be found at certain 3' end positions, supporting the notion that there are no simple rules for predicting mismatch effects based on position[4]. Interestingly, some off-target sites actually have higher sequencing read counts than their matched on-target sites (FIGS. 6A-D, 6J), consistent with our previous observations that off-target mutation frequencies can in certain cases be higher than those at the intended on-target site[4]. Notably, many of the previously known off-target sites for four of the RGNs have high read counts (FIGS. 6A-D), suggesting that previous analyses primarily identified sites that are most efficiently cleaved.

Figure 14:
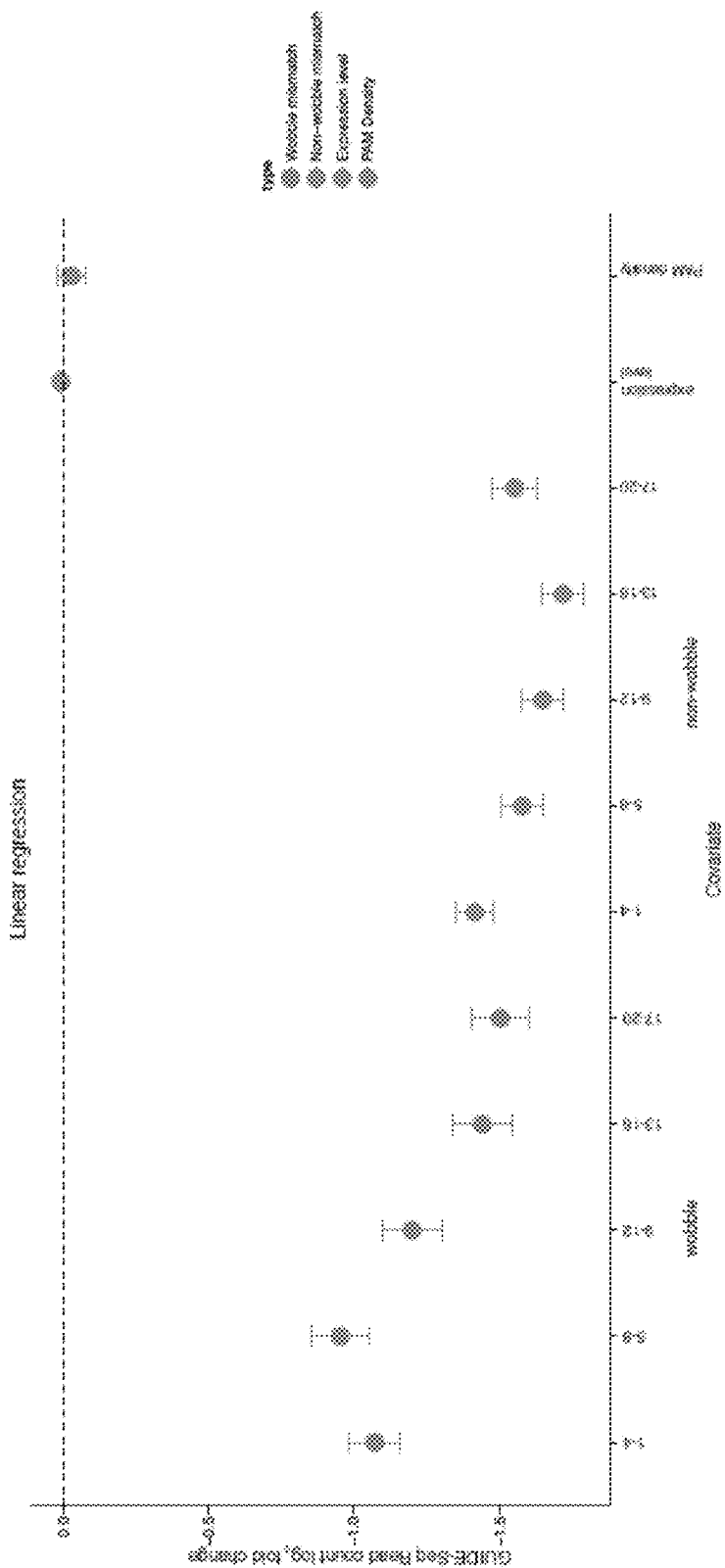
Figure 15A:
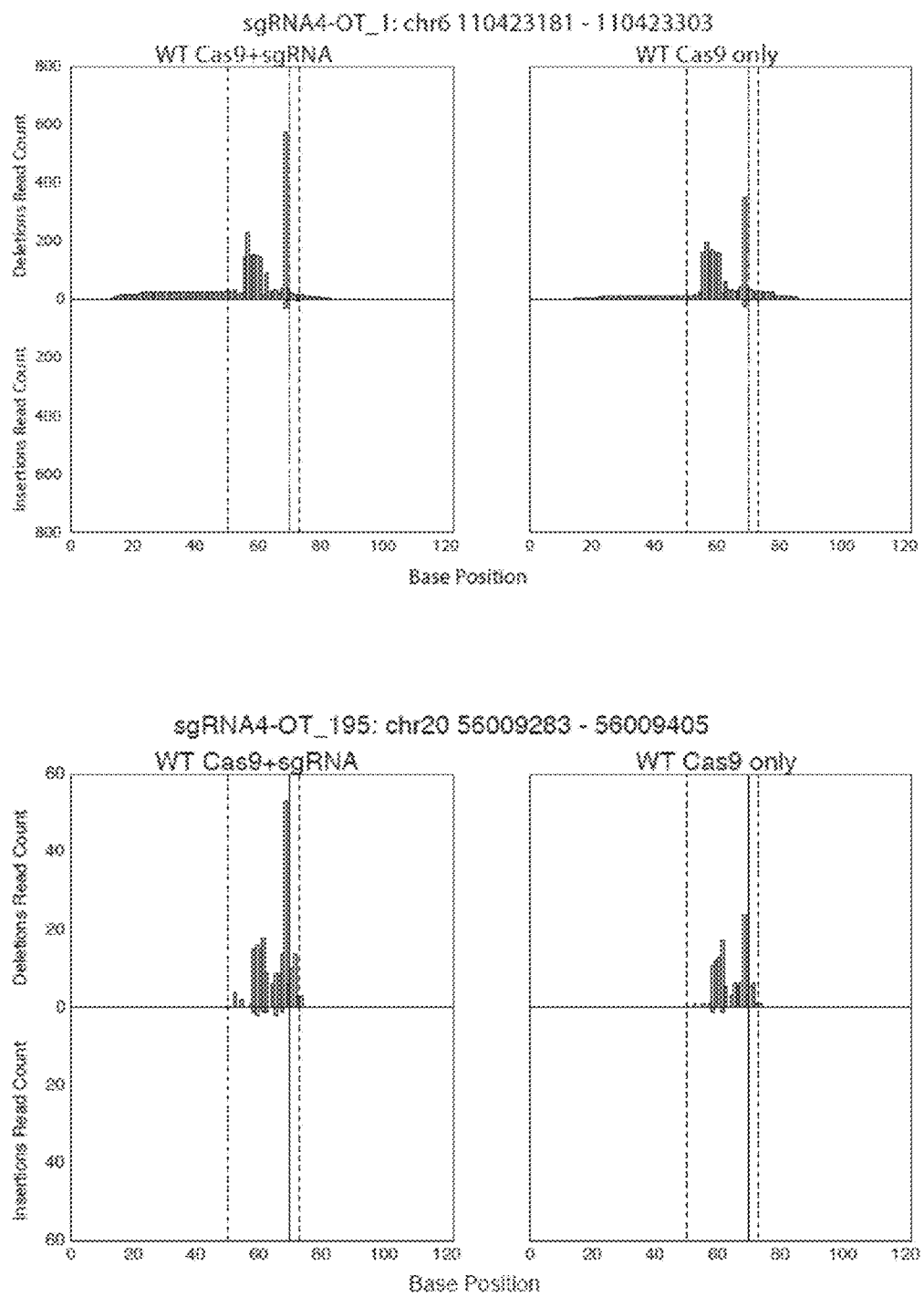
Figure 15C:
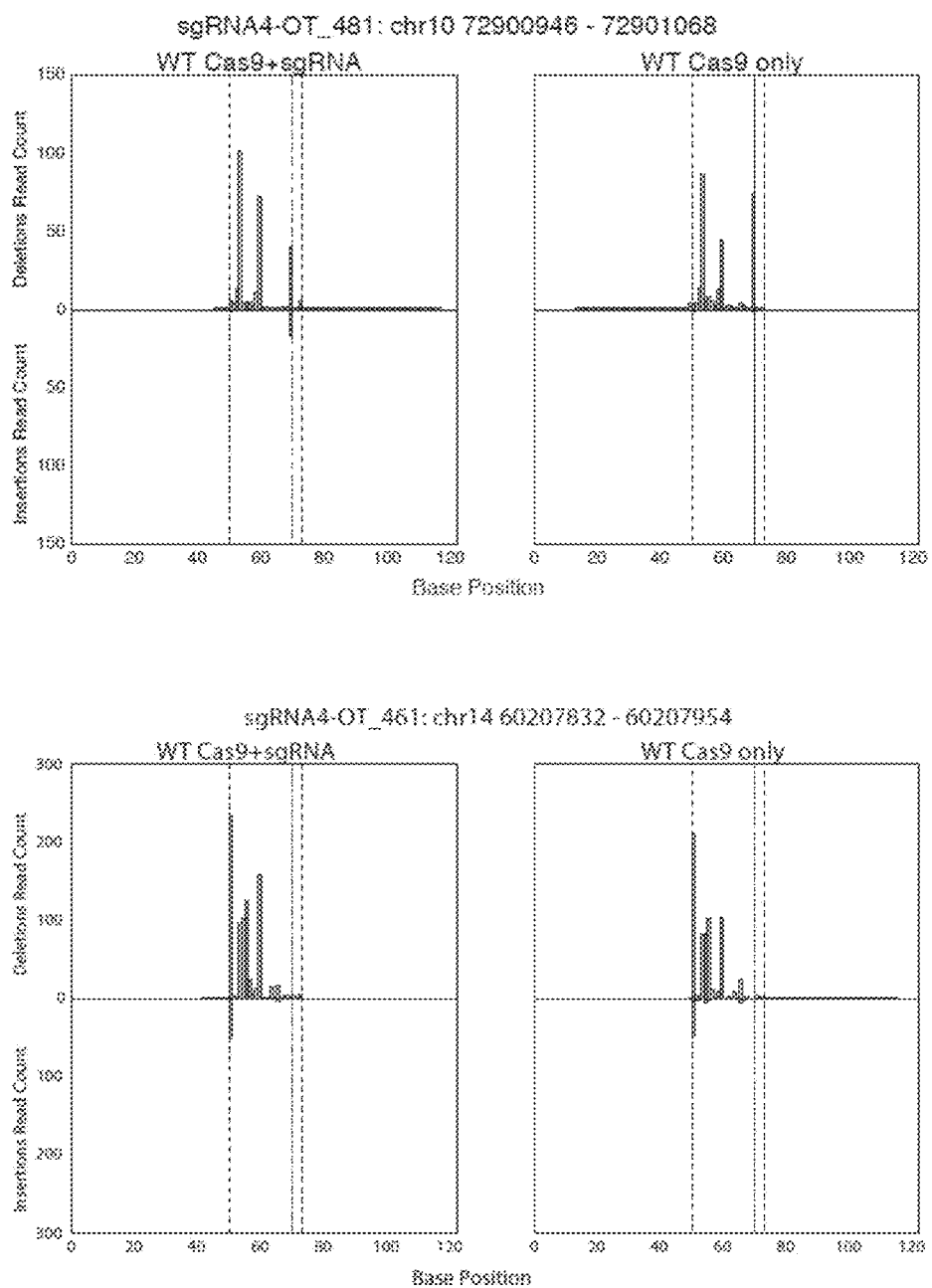
Figure 15D:
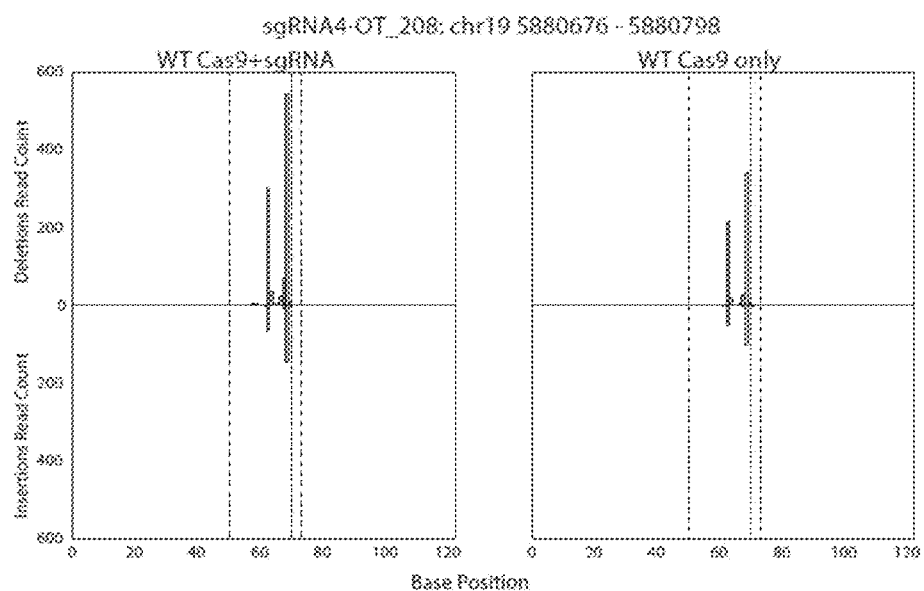

Quantitative analysis of our GUIDE-Seq data on all ten RGNs enabled us to quantify the contributions and impacts of different variables such as mismatch number, location, and type on off-target site cleavage. We found that the fraction of total genomic sites bearing a certain number of protospacer mismatches that are cleaved by an RGN decreases with increasing numbers of mismatches (FIG. 8A). In addition, sequence read counts show a general downward trend with increasing numbers of mismatches (FIG. 8B). In general, protospacer mismatches positioned closer to the 5' end of the target site tend to be associated with smaller decreases in GUIDE-Seq read counts than those closer to the 3' end although mismatches positioned 1 to 4 bp away from the PAM are surprisingly somewhat better tolerated than those 5 to 8 bps away (FIG. 8C). Interestingly, the nature of the mismatch is also associated with an effect on GUIDE-Seq read counts. Wobble mismatches occur frequently in the off-target sites and our analysis suggests they are associated with smaller impacts on GUIDE-Seq read counts than other non-Wobble mismatches (FIG. 8D). Consistent with these results, we find that the single factors that explain the greatest degree of variation in off-target cleavage in univariate regression analyses are mismatch number, position, and type. In contrast, other factors such as the density of proximal PAM sequences, gene expression level, or genomic position (intergenic/intronic/exonic) explain a much smaller proportion of the variance in GUIDE-Seq cleavage read counts (FIG. 8E). A combined linear regression model that considered multiple factors including mismatch position, mismatch type, gene expression level, and density of proximal PAM sequences yielded results consistent with the univariate analyses (FIG. 14). This analysis also allowed us to independently estimate that, on average and depending on their position, each additional wobble mismatch decreases off-target cleavage rates by ~2- to 3-fold, while additional non-wobble mismatches decrease cleavage rates by ~3-fold (FIG. 14).

Comparisons of GUIDE-Seq with Existing Off-Target Prediction Methods

Figure 9A:
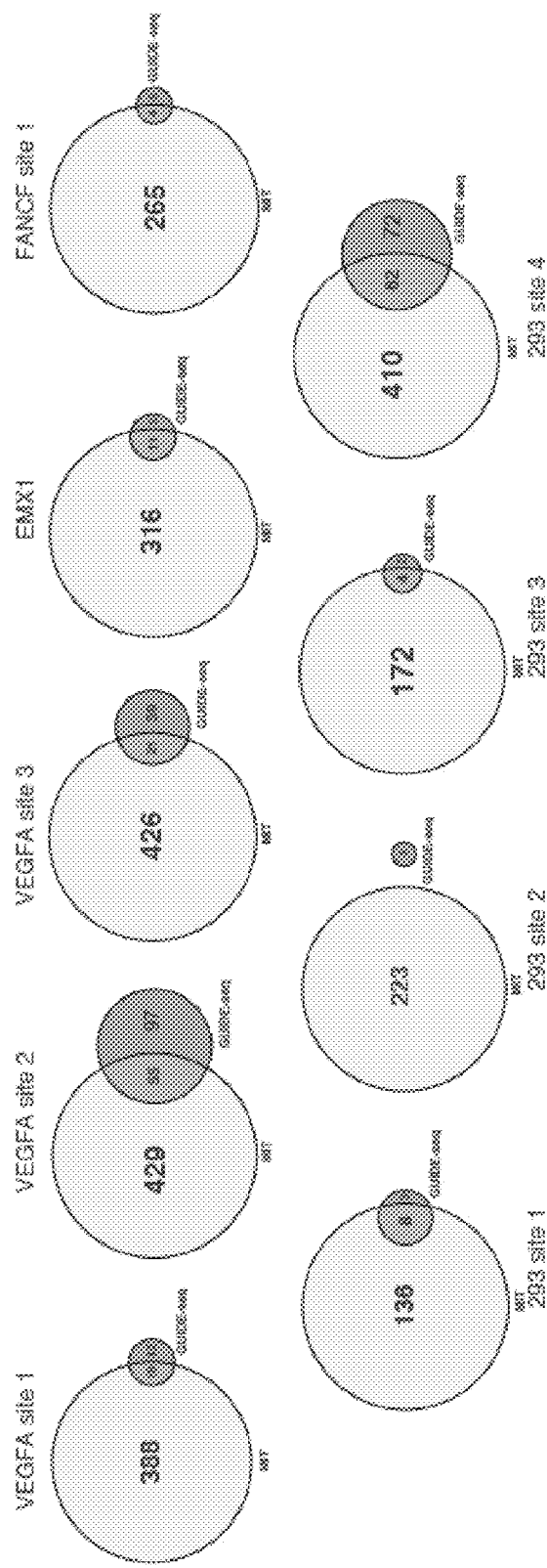
Figure 9B:
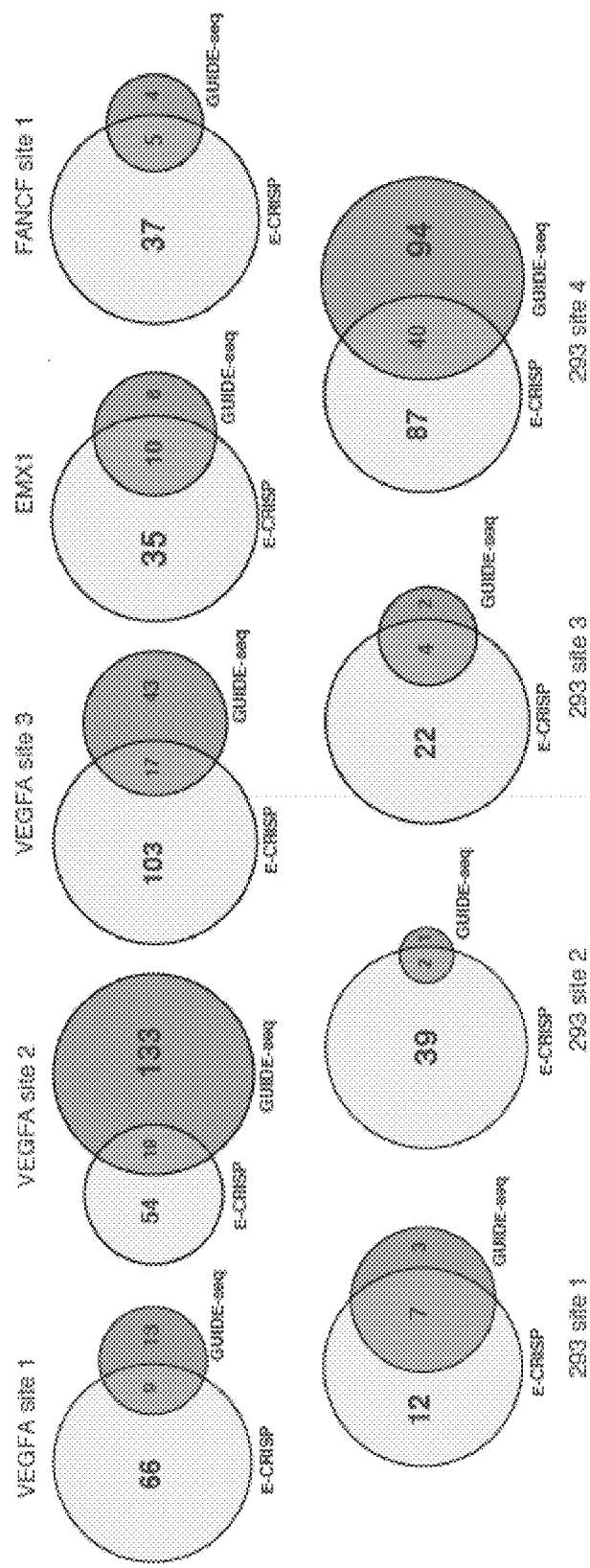
Figure 9D:
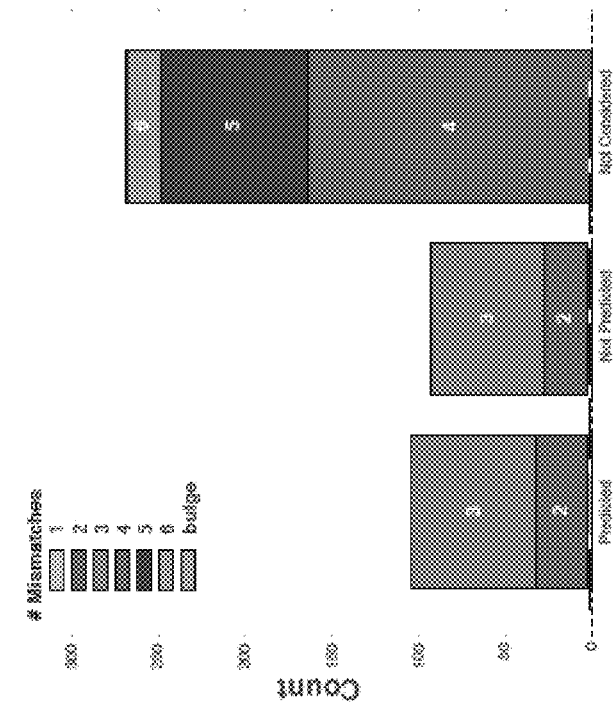
Figure 9C:
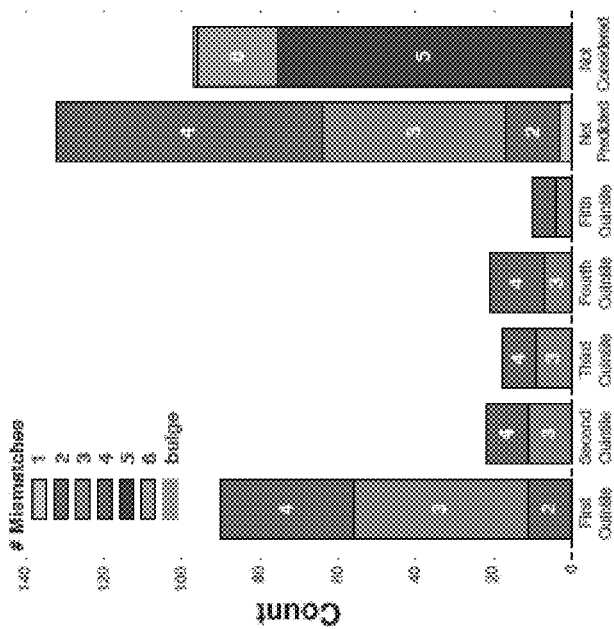
Figure 9F:
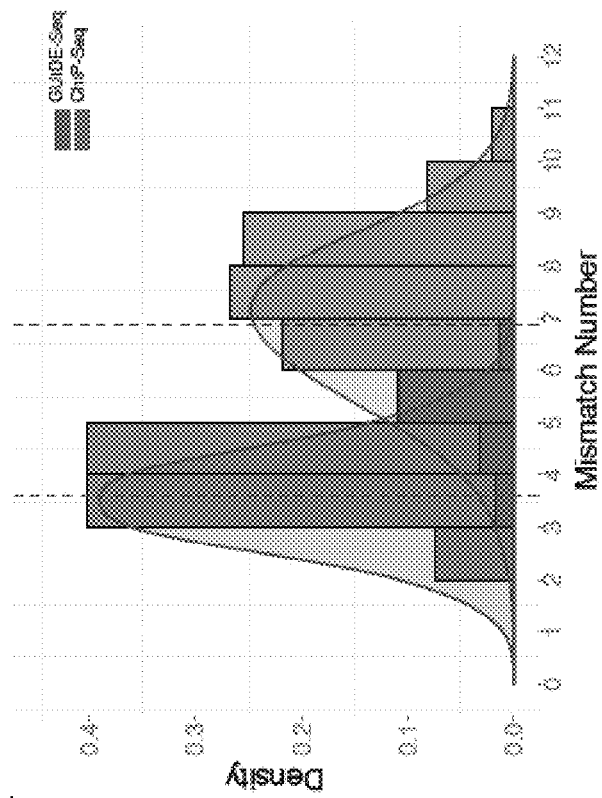

Having established the efficacy of GUIDE-Seq, we next performed direct comparisons of our new method with two popular existing computational methods for predicting off-target mutation sites: the MIT CRISPR Design Tool[25] (crispr.mit.edu) and the E-CRISP program[26] (www.e-crisp.org/E-CRISP/). Both of these programs attempt to identify potential off-target sites based on certain "rules" about mismatch number and position and have been used in previous publications to identify off-target sites. In our comparisons using the ten RGNs we characterized by GUIDE-Seq, we found that both programs failed to identify the vast majority of experimentally verified off-target sites (FIGS. 9A-B). Many of these sites were missed because the E-CRISP and MIT programs simply do not consider off-targets bearing more than 3 and 4 mismatches, respectively (FIGS. 9C-D). Even among the sequences that are considered, these programs still fail to identify the majority of the bona fide off-target sites (FIG. 9C-D), highlighting their currently limited capability to account for the factors that determine whether or not cleavage will or will not occur. In particular, it is worth noting that sites missed include those with as few as one mismatch (FIGS. 9C-D), though the ranking scores assigned by the MIT program do have some predictive power among the sites it does correctly identify. Finally, it is important to note that both programs return many "false positive" sites that are not identified by GUIDE-Seq (FIGS. 9A-B). We conclude that both the MIT and the E-CRISP programs perform substantially less effectively than our GUIDE-Seq method at identifying bona fide RGN off-target sites.

Figure 9E:
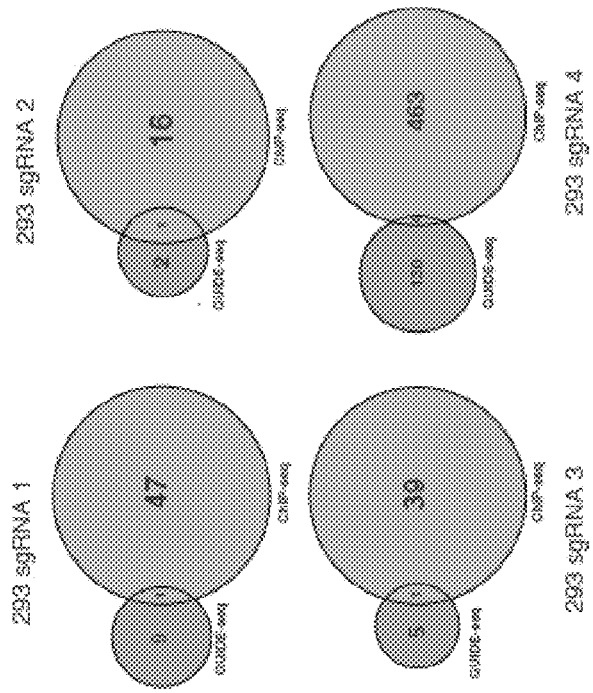

Comparison of GUIDE-Seq with the ChIP-Seq Method for Determining dCas9 Binding Sites We also sought to directly compare GUIDE-Seq with previously described ChIP-Seq methods for identifying RGN off-target sites. Four of the RGNs we evaluated by GUIDE-Seq used gRNAs that had been previously characterized in ChIP-Seq experiments with catalytically inactive Cas9 (dCas9), resulting in the identification of a large set of off-target binding site[18]. Direct comparisons show very little overlap between Cas9 off-target cleavage sites identified by GUIDE-Seq and dCas9 off-target binding sites identified by ChIP-Seq; among the 149 RGN-induced off-target cleavage sites we identified for the four gRNAs, only three were previously identified by the previously published dCas9 ChIP-Seq experiments using the same gRNAs (FIG. 9E). This lack of overlap is likely because dCas9 off-target binding sites are fundamentally different from Cas9 off-target cleavage sites, a hypothesis supported by our data showing that Cas9 off-target cleavage sites for these four gRNAs identified by GUIDE-Seq harbor on average far fewer mismatches than their binding sites identified by ChIP-Seq (FIG. 9F) and by the results of previous studies showing that very few dCas9 binding sites show evidence of indels in the presence of active Cas9[16-19]. Although GUIDE-Seq failed to identify the four off-target sites previously identified by ChIP-Seq and subsequently shown to be targets of mutagenesis by Cas9, we believe this is because those sites were incorrectly identified as bona fide off-target cleavage sites in that earlier study. Careful analysis of the sequencing data from that study suggests that the vast majority of indel mutations found at those sites are likely caused instead by PCR or sequencing errors and not by RGN cleavage activity (FIGS. 15A-D). Taken together, these findings demonstrate that GUIDE-Seq substantially outperforms ChIP-Seq for identification of bona fide off-target cleavage sites and provide experimental support for the idea that very few (if any) dCas9 off-target binding sites discovered by ChIP-Seq represent actual Cas9 off-target cleavage sites.

Identification of RGN-Independent DSB Hotspots in Human Cells by GUIDE-Seq

Our GUIDE-Seq experiments also unexpectedly revealed the existence of a total of 30 unique RGN-independent DSB hotspots in the U2OS and HEK293 cells used for our studies (Table 2). We uncovered these sites when analyzing genomic DNA from control experiments with U2OS and HEK293 cells in which we transfected only the dsODN without RGN-encoding plasmids (Methods). In contrast to RGN-induced DSBs that map precisely to specific base pair positions, RGN-independent DSBs have dsODN integration patterns that are more broadly dispersed at each locus in which they occur (Methods). These 30 breakpoint hotspots were distributed over many chromosomes and appeared to be present at or near centromeric or telomeric regions (FIG. 10F). Interestingly, only a small number of these DSBs (two) were common to both cell lines with the majority appearing to be cell line-specific (25 in U2OS and 7 in HEK293 cells; FIG. 10F and Table 2). To our knowledge, GUIDE-Seq is the first method to enable direct and unbiased identification of breakpoint hotspots in living human cells without the need for potentially toxic drugs (e.g., DNA replication inhibitors such as aphidicolin) to unveil their presence.

Figure 10A:
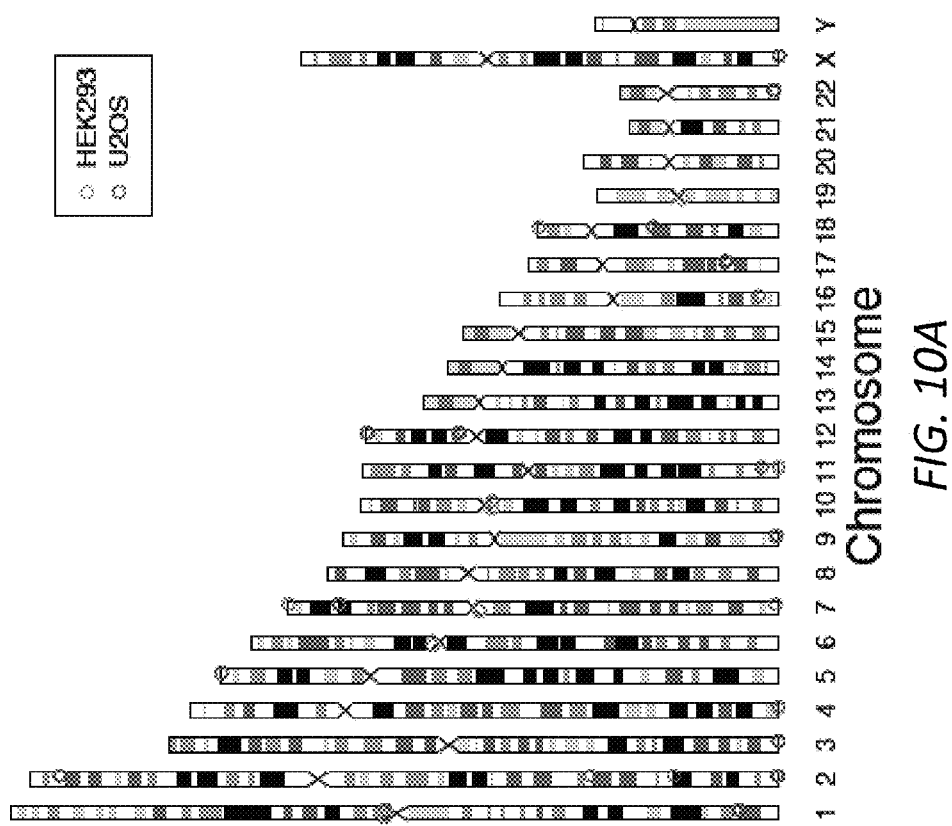

Participation of Both RGN-Induced and RGN-Independent DSBs in Large-Scale Genomic Rearrangements In the course of analyzing the results of our next-generation sequencing experiments designed to identify indels at RGN-induced and RGN-independent DSBs, we also discovered that some of these breaks can participate in translocations, inversions and large deletions. The AMP method used enabled us to observe these large-scale genomic alterations because, for each DSB site examined, this method uses only nested locus-specific primers anchored at only one fixed end rather than a pair of flanking locus-specific primers (FIG. 10A). Thus, AMP-based sequencing not only identifies whether indel mutations have occurred at a DSB but it can also detect whether the DSB has been joined to another sequence.

Figure 10B:
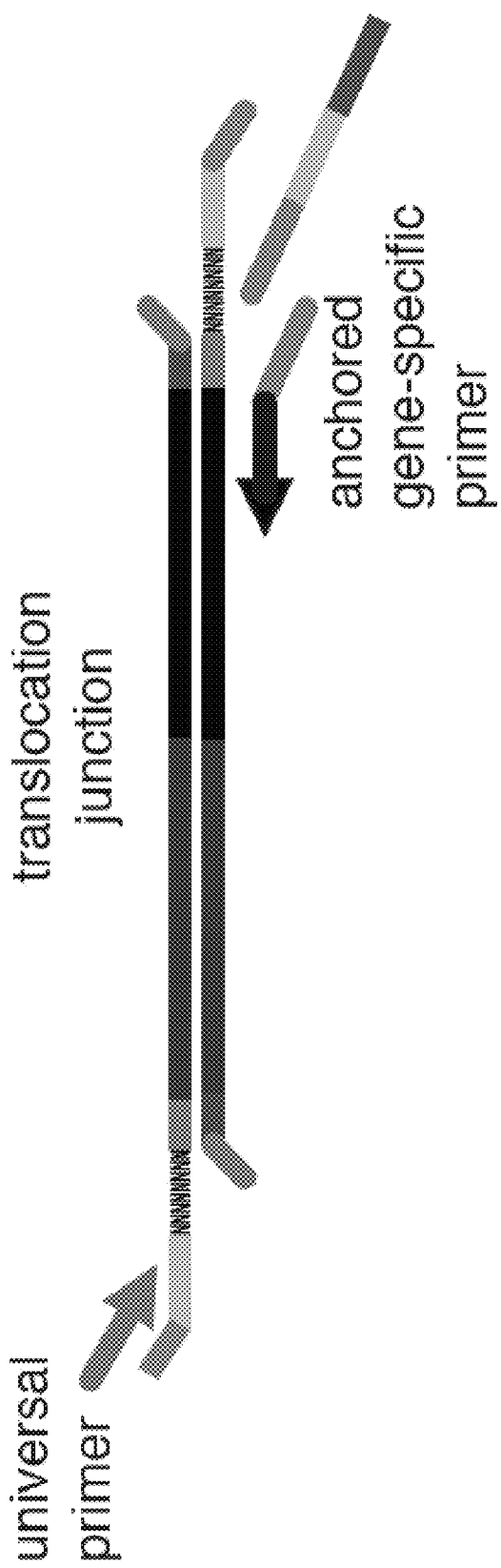
Figure 10C:
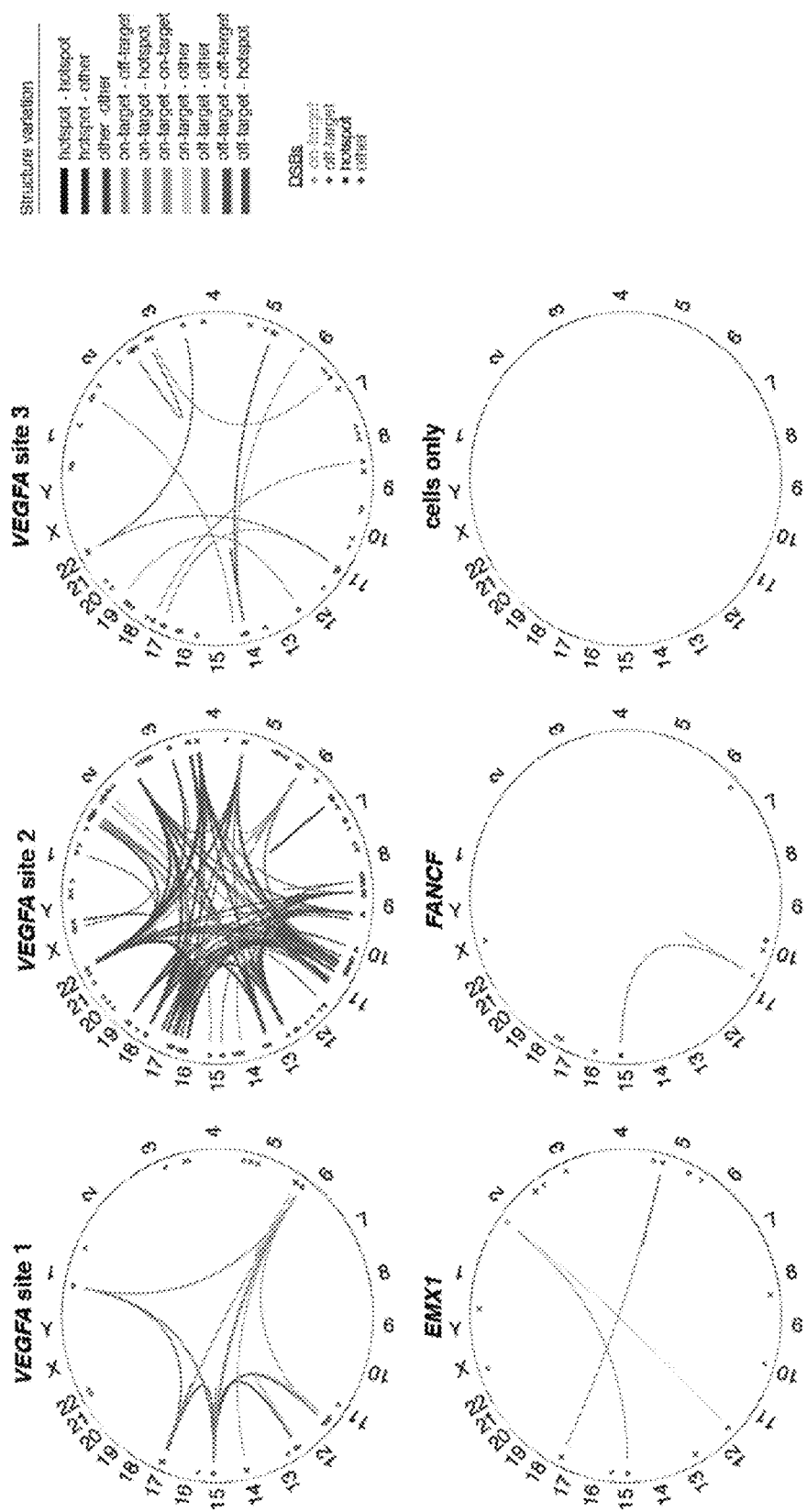
Figure 11C:
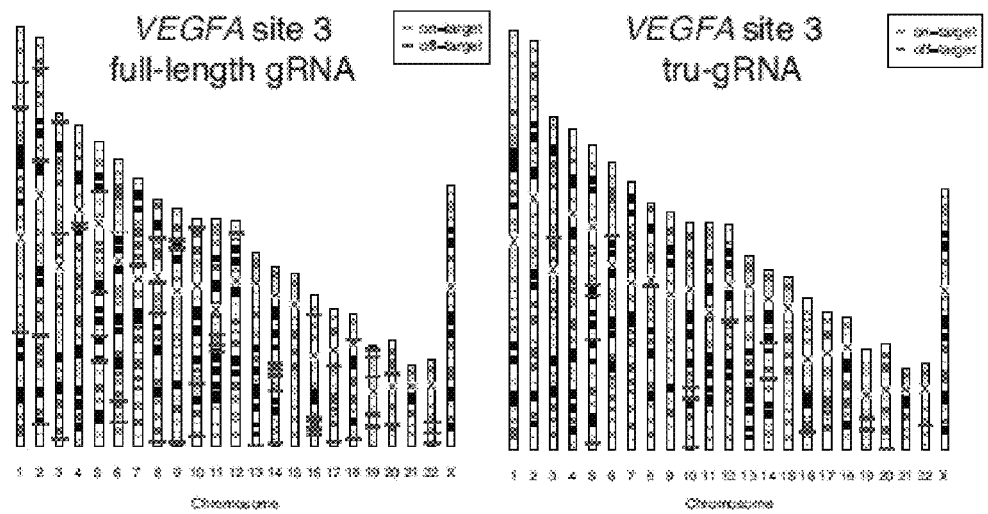
Figure 11D:
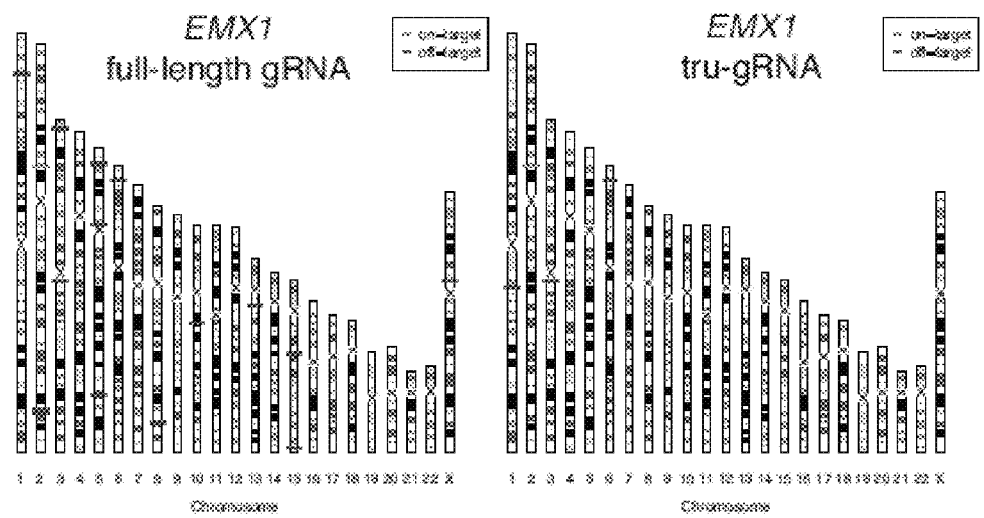
Figure 11E:
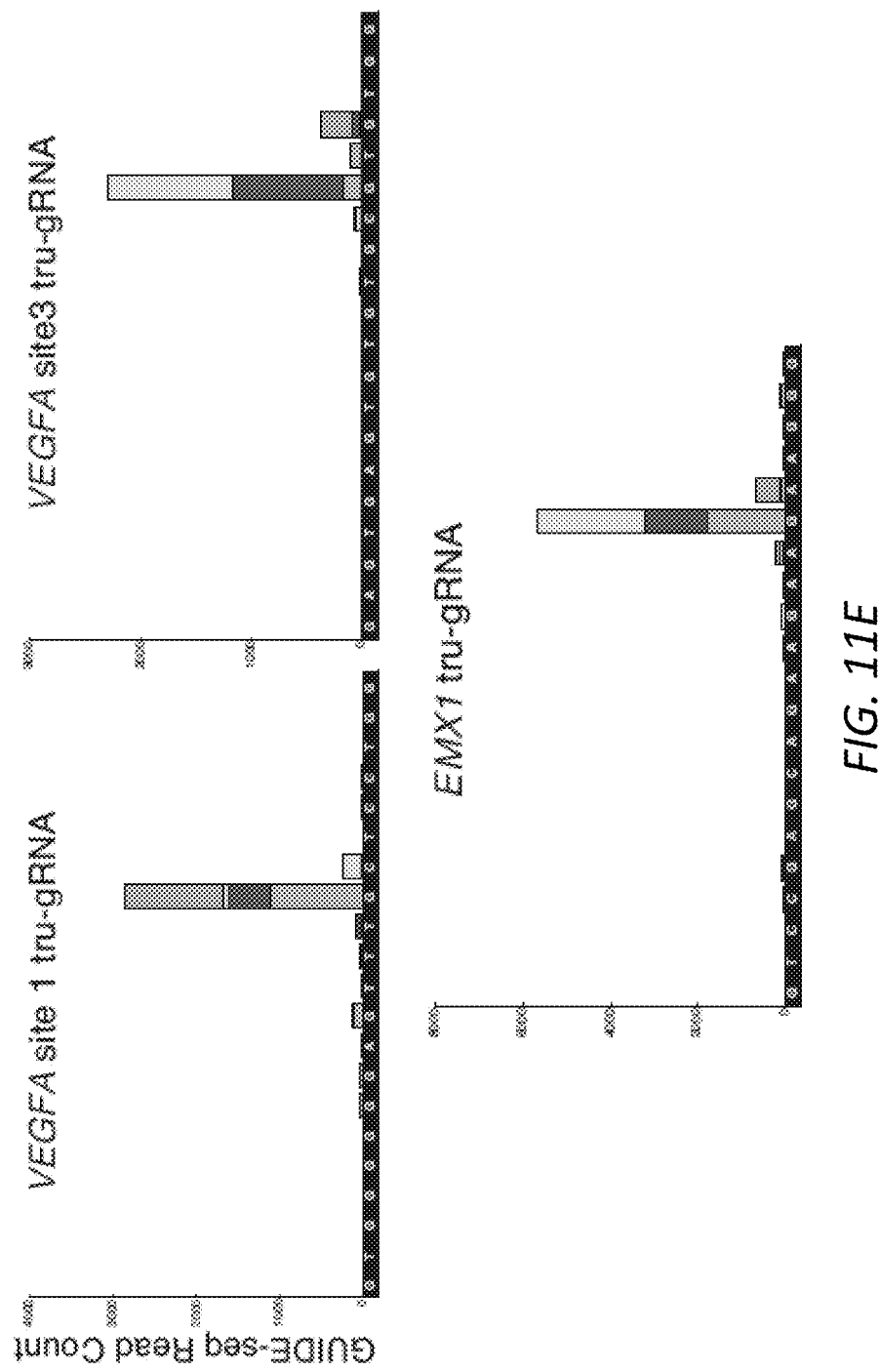

For the five RGNs we examined, AMP sequencing revealed that RGN-induced on-target and off-target DSBs could participate in a variety of translocations (FIG. 10B). In at least one case, we could observe all four possible translocation events resulting from a pair of DSBs (FIG. 10C). When two DSBs were present on the same chromosome, we also observed large deletions and inversions (FIG. 10B). For at least one case, we observed both a large deletion between two RGN-induced breaks as well as an inversion of that same intervening sequence (FIG. 10D). Importantly, our results also revealed translocations (and deletions or inversions) between RGN-induced and RGN-independent DSBs (FIG. 10B), suggesting that the interplay between these two types of breaks needs to be considered when evaluating the off-target effects of RGNs on cellular genomes. Although our data suggest that the frequencies of these large-scale genomic rearrangements are likely to be very low, precise quantification was not possible with the sequencing depth of our existing dataset. Increasing the number of sequencing reads should increase the sensitivity of detection and enable better quantitation of these important genomic alterations.

GUIDE-Seq Profiles of RGNs Directed by Truncated gRNAs

Previous studies from our group have shown that use of gRNAs bearing truncated complementarity regions of 17 or 18 nts can reduce mutation frequencies at known off-target sites of RGNs directed by full-length gRNAs27. However, because this analysis was limited to a small number of known off-target sites, the genome-wide specificities of these truncated gRNAs (tru-gRNAs) remained undefined in our earlier experiments. We used GUIDE-Seq to obtain genome-wide DSB profiles of RGNs directed by three tru-gRNAs, each of which are shorter versions of one of the ten full-length gRNAs we had assayed above.

Our results show that in all three cases, the total number of off-target sites identified by GUIDESeq decreased substantially with use of a tru-gRNA (FIG. 11A-D). Mapping of GUIDE-Seq reads enabled us to precisely identify the cleavage locations of on-target (FIG. 11E) and off-target sites (not shown). As expected and as we observed with full-length gRNAs, included in the list of off-target sites were 10 of the 12 previously known off-target sites for RGNs directed by the three tru-gRNAs (FIGS. 11F-H). The sequences of the off-target sites we identified primarily had one or two mismatches in the protospacer but some sites had as many as four (FIGS. 11F-H). In addition, some sites had alternative PAM sequences of the forms NAG, NGA, and NTG (FIGS. 11F-H). These data provide confirmation on a genome-wide scale that truncation of gRNAs can substantially reduce off-target effects of RGNs and show how GUIDESeq can be used to assess specificity improvements for the RGN platform.

TABLE 2

Summary of RGN-independent breakpoint hotspots in human U2OS and HEK293 cells

| Cells | Chromosome | Start | End | Interval (bp) |
|---|---|---|---|---|
| U2OS | chr1 | 121484547 | 121485429 | 882 |
| U2OS | chr1 | 236260170 | 236260754 | 584 |
| U2OS | chr3 | 197900267 | 197900348 | 81 |
| U2OS | chr4 | 191044096 | 191044100 | 4 |
| U2OS | chr5 | 10020 | 10477 | 457 |
| U2OS | chr7 | 16437577 | 16439376 | 1799 |
| U2OS | chr7 | 158129486 | 158129491 | 5 |
| U2OS | chr9 | 140249964 | 140249977 | 13 |
| U2OS | chr9 | 140610510 | 140610516 | 6 |
| U2OS | chr10 | 42599569 | 42599575 | 6 |
| U2OS | chr11 | 129573467 | 129573469 | 2 |
| U2OS | chr11 | 134946499 | 134946506 | 7 |
| U2OS | chr12 | 95427 | 95683 | 256 |
| U2OS | chr12 | 29944278 | 29946544 | 2266 |
| U2OS | chr16 | 83984266 | 83984271 | 5 |
| U2OS | chr17 | 63965908 | 63967122 | 1214 |
| U2OS | chr18 | 63765 | 63769 | 4 |
| U2OS | chr18 | 37381409 | 37381971 | 562 |
| U2OS | chr2 | 9877829 | 9877857 | 28 |
| U2OS | chr2 | 182140586 | 182140587 | 1 |
| U2OS | chr2 | 209041635 | 209041637 | 2 |
| U2OS | chr2 | 242838677 | 242838859 | 182 |
| U2OS | chr22 | 49779897 | 49782342 | 2445 |
| U2OS | chr22 | 49780337 | 49780338 | 1 |
| U2OS | chrX | 155260204 | 155260352 | 148 |
| HEK293 | chr1 | 121484526 | 121485404 | 878 |
| HEK293 | chr6 | 58778207 | 58779300 | 1093 |
| HEK293 | chr7 | 61968971 | 61969378 | 407 |
| HEK293 | chr10 | 42385171 | 42385189 | 18 |
| HEK293 | chr10 | 42400389 | 42400394 | 5 |
| HEK293 | chr10 | 42597212 | 42599582 | 2370 |
| HEK293 | chr19 | 27731978 | 27731991 | 13 |

Discussion

GUIDE-Seq provides an unbiased, sensitive, and genome-wide method for detecting RGN-induced DSBs. The method is unbiased because it detects DSBs without making assumptions about the nature of the off-target site (e.g., presuming that the off-target site is closely related in sequence to the on-target site). GUIDE-Seq identifies off-target sites genome-wide, including within exons, introns, and intergenic regions, and harbored up to six protospacer mismatches and/or new mismatched PAM sites beyond the alternate NAG and NGA sequences described in earlier studies[5, 23]. For the RGNs we examined in this example, GUIDE-Seq not only successfully identified all previously known off-target sites but also unveiled hundreds of new sites as well.

Although the current lack of a practical gold standard method for comprehensively identifying all RGN off-target sites in a human cell prevents us from knowing the sensitivity of GUIDE-Seq with certainty, we believe that it very likely has a low false-negative rate for the following reasons: First, all RGN-induced blunt-ended DSBs should take up the blunt-ended dsODN by NHEJ, a hypothesis supported by the strong correlations we observe between GUIDE-Seq read counts (which measure dsODN uptake) and indel frequencies in the presence of the RGN (which measure rates DSB formation and of their mutagenic repair) (FIGS. 7B-F). We note that these correlations include over 130 sites which show a wide range of indel mutagenesis frequencies. Second, using previously identified off-target sites as a benchmark (which is the only way to gauge success at present), GUIDE-Seq was able to detect 38 out of 40 of these sites that show a range of mutagenesis frequencies extending to as low as 0.12%. The method detected all 28 previously known off-target sites for four full-length gRNAs and 10 out of 12 previously known off-target sites for three tru-gRNAs. One of the two off-target sites that was not detected showed evidence of capture in our raw data but was filtered out by our read calling algorithm because the sequencing reads were only unidirectional and originated from just one primer (Methods). (The lack of bidirectional mapping reads for this site might be due to a repetitive region on one side of the off-target site that makes it challenging to map the reads accurately.) The other undetected offtarget site has been previously.

Of note, one of the RGNs we assessed did not yield any detectable off-target effects (at the current detection limit of the GUIDE-Seq method), raising the intriguing possibility that some gRNAs may induce very few, or perhaps no, undesired mutations.

Although our validation experiments show that GUIDE-Seq can sensitively detect off-target sites that are mutagenized by RGNs with frequencies as low as 0.1%, its detection capabilities might be further improved with some simple changes. Strategies that use next-generation sequencing to detect indels are limited by the error rate of the platform (typically ~0.1%). By contrast, GUIDE-Seq uses sequencing to identify dsODN insertion sites rather than indels and is therefore not limited by error rate but by sequencing depth. For example, we believe that the small number of sites detected in our GUIDE-Seq experiments for which we did not find indels in our sequencing validation experiments actually represent sites that likely have indel mutation frequencies below 0.1%. Consistent with this, we note that all but three of these 26 sites had GUIDE-Seq read counts below 100. Taken together, these observations suggest that we may be able to increase the sensitivity of GUIDE-Seq simply by increasing the number of sequencing reads (and by increasing the number of genomes used as template for amplification). For example, use of a sequencing platform that yields 1000-fold more reads would enable detection Direct comparisons enabled by our GUIDE-Seq experiments show the limitations of two existing computational programs for predicting RGN off-target sites. These programs not only failed to identify bona fide off-target sites found by GUIDE-Seq but also overcalled many sites that do not show cleavage. This is not entirely surprising given that parameters used by these programs were based on more restrictive assumptions about the nature of off-target sites that do not account for greater numbers of protospacer mismatches and alternative PAM sequences identified by our GUIDE-Seq experiments. It is possible that better predictive programs might be developed in the future but doing so will require experimentally determined genome-wide off-target sites for a larger number of RGNs. Until such programs can be developed, identification of off-target sites will be most effectively addressed by experimental methods such as GUIDE-Seq.

Our experimental results elaborate a clear distinction between off-target binding site of dCas9 and off-target cleavage sites of Cas9. Comparisons of dCas9 ChIP-Seq and Cas9 GUIDE-Seq data for four different gRNAs show that there is negligible direct overlap between the two sets of sites and that the mean number of mismatches in the two classes of sites are actually substantially different. Furthermore, we show that even the small number of dCas9 binding sites previously reported to be mutagenized by Cas9 are very likely not bona fide RGN-induced cleavage sites. Taken together, our results show that the binding of dCas9 to DNA sites being captured with ChIP-Seq represents a different biological process than cleavage of DNA sites by Cas9 nuclease, consistent with the results of a recent study showing that engagement of the 5'-end of the gRNA with the protospacer is needed for efficient cleavage[19]. Although ChIP-Seq assays will undoubtedly have a role in characterizing the genome-wide binding of dCas9 fusion proteins, the method is clearly not effective for determining genome-wide off-target cleavage sites of catalytically active RGNs.

GUIDE-Seq has several important advantages over other previously described genome-wide methods for identifying DSB sites in cells. The recently described BLESS (breaks labeling, enrichment on streptavidin and next-generation sequencing) oligonucleotide tagging method is performed in situ on fixed, permeabilized cells[27]. In addition to being prone to artifacts associated with cell fixation, BLESS will only capture breaks that exist at a single moment in time. By contrast, GUIDE-Seq is performed on living cells and captures DSBs that occur over a more extended period of time (days), thereby making it a more sensitive and comprehensive assay. Capture of integration-deficient lentivirus (IDLV) DNA into regions near DSBs and identification of these loci by LAM-PCR has been used to identify a small number of off-target sites for engineered zinc finger nucleases (ZFNs)[22] and transcription activator-like effector nucleases (TALENs)[28] in human cells. However, IDLV integration events are generally low in number and widely dispersed over distances as far as 500 bps away from the actual off-target DSB[22, 28], making it challenging both to precisely map the location of the cleavage event and to infer the sequence of the actual off-target site. In addition, LAM-PCR suffers from sequence bias and/or low efficiency of sequencing reads. Collectively, these limitations may also explain the apparent inability to detect lower frequency ZFN off-target cleavage sites by IDLV capture[29]. By contrast, dsODNs are integrated very efficiently and precisely into DSBs with GUIDE-Seq, enabling mapping of breaks with single nucleotide resolution and simple, straightforward identification of the nuclease off-target cleavage sites. Furthermore, in contrast to LAM-PCR, our STAT-PCR method allows for efficient, unbiased amplification and sequencing of genomic DNA fragments in which the dsODN has integrated. We note that the STAT-PCR may have more general utility beyond its use in GUIDE-Seq; for example, it may be useful for studies that seek to map the integration sites of viruses on a genome-wide scale.

Although GUIDE-Seq is highly sensitive, its detection capabilities might be further improved with some simple changes. Strategies that use next-generation sequencing to detect indels are limited by the error rate of the platform (typically ~0.1%). By contrast, GUIDE-Seq uses sequencing to identify dsODN insertion sites rather than indels and is therefore not limited by error rate but by sequencing depth. For example, we believe that the small number of sites detected in our GUIDE-Seq experiments for which we did not find indels in our sequencing validation experiments actually represent sites that likely have mutation frequencies below 0.1%. Consistent with this, we note that all but 3 of these 26 sites had GUIDE-Seq read counts below 100. Taken together, these observations suggest that we may be able to increase the sensitivity of GUIDE-Seq simply by increasing the number of sequencing reads (and by increasing the number of genomes used as template for amplification). For example, use of a sequencing platform that yields 1000-fold more reads would enable detection of sites with mutagenesis frequencies three orders of magnitude lower (i.e., 0.0001%), and we expect further increases to occur with continued improvements in technology.

An unexpected result of our experiments was the realization that GUIDE-Seq could also identify breakpoint hotspots that occur in cells even in the absence of RGNs. We believe that these DSBs are not just an artifact of GUIDE-Seq because our AMP-based sequencing experiments verified not only capture of dsODNs but also the formation of indels at these sites. Of note, many hotspots are unique to each of the two cell lines examined in our study, but some also appear to be common to both. It will be interesting in future studies to define the parameters that govern why some sites are breakpoint hotspots in one cell type but not another. Also, because our results show that these breakpoint hotspots can participate in translocations, the existence of cell-type-specific breakpoint hotspots might help to explain why certain genomic rearrangements only occur in specific cell types but not others. To our knowledge, GUIDE-Seq is the first method to be described that can identify breakpoint hotspots in living human cells without the need to add drugs that inhibit DNA replication[27]. Therefore, we expect that it will provide a useful tool for identifying and studying these breaks.

Our work establishes the most comprehensive qualitative approach described to date for identifying translocations induced by RGNs. AMP-based targeted sequencing of RGN-induced and RGN-independent DSB sites discovered by GUIDE-Seq can find large-scale genomic rearrangement that includes translocations, deletions, and inversions involving both classes of sites, highlighting the importance of considering both classes of breaks when identifying large-scale genomic rearrangements. In addition, presumably not all RGN-induced or RGN-independent DSBs will participate in large-scale alterations and understanding why some sites do and other sites do not contribute to these rearrangements will be an important area for further research.

GUIDE-Seq will also provide an important means to evaluate specificity improvements to the RGN platform on a genome-wide scale. In this report, we used GUIDE-Seq to show how the implementation of truncated gRNAs can reduce off-target effects on a genome-scale, extending earlier results from our group that this approach can reduce mutations at known off-target sites of a matched full-length gRNA[30]. It might also be adapted to assess the genome-wide specificities of alternative Cas9 nucleases from other bacteria or archaea, or of nucleases such as dimeric ZFNs, TALENs, and CRISPR RNA-guided FokI nucleases[31, 32] that generate 5' overhangs or paired Cas9 nickases[33, 34] that generate 5' or 3' overhangs; however, extending GUIDE-Seq to detect these other types of DSBs will undoubtedly require additional modification and optimization of the dsODN to ensure its efficient capture into such breaks. The method might also be used to assess the specificities of alternative Cas9 nucleases from other bacteria or archaea[35]. One important caveat is the need to examine a large number of gRNAs before broadly drawing conclusions about the specificity of any new Cas9 platform because we found very wide variability in the number of off-target sites for the ten gRNAs we assessed.

Our exemplary approach using GUIDE-Seq and AMP-based sequencing establishes a new gold standard for the evaluation of off-target mutations and genomic rearrangements induced by RGNs. We expect that GUIDE-Seq can be extended for use in any cell in which NHEJ is active and into which the required components can be efficiently introduced; for example, we have already achieved efficient dsODN integration in human K562 and mouse embryonic stem cells (data not shown). Most importantly, the strategies outlined here can be used as part of a rigorous pre-clinical pathway for objectively assessing the potential off-target effects of any RGNs proposed for therapeutic use, thereby substantially improving the prospects for use of these reagents in the clinic.

Example 3

Additional experiments were performed to explore the requirements for the dsODNs that can be used in some embodiments of the present methods.

The following dsODNs were used in the experiments in Example 3:

| dsODN type | Sequence | SEQ ID NO: |
| --- | --- | --- |
| phosphorylated, 5' overhang, 5' end-protected F | /5Phos/N*N*NNGTTTAATTGAGTT GTCATATGTTAATAACGGT*A*T | 47 |
| phosphorylated, 5' overhang, 5' end-protected R | /5Phos/N*N*NNATACCGTTATTAA CATATGACAACTCAATTAA*A*C | 48 |

-continued

| dsODN type | Sequence | SEQ ID NO: |
|---|---|---|
| phosphorylated, 3' overhang, 3' end-protected F | /5Phos/G*T*TTAATTGAGTTGTCAT ATGTTAATAACGGTATNN*N*N | 49 |
| phosphorylated, 3' overhang, 3' end-protected R | /5Phos/A*T*ACCGTTATTAACATA TGACAACTCAATTAAACNN*N*N | 50 |
| phosphorylated, blunt, 5' and 3' end-protected F | /5Phos/G*T*TTAATTGAGTTGTCAT ATGTTAATAACGGT*A*T | 1 |
| phosphorylated, blunt, 5' and 3' end-protected R | /5Phos/A*T*ACCGTTATTAACATA TGACAACTCAATTAA*A*C | 2 |
| phosphorylated, blunt, 3' end-protected F | /5Phos/GTTTAATTGAGTTGTCATA TGTTAATAACGGT*A*T | 51 |
| phosphorylated, blunt, 3' end-protected R | /5Phos/ATACCGTTATTAACATATG ACAACTCAATTAA*A*C | 52 |

/5Phos/ indicates 5' phosphorylation
*indicates phosphorothioate linkage
All oligos were annealed in STE.

First, the integration frequencies of 3 types of dsODNs using TALENs, ZFNs, and RFNs targeted against EGFP were evaluated. 2E5 U2OS-EGFP cells were nucleofected with 500 ng each TALEN monomer (1 ug total), 500 ng each ZFN monomer (1 ug total), or 325 ng multiplex gRNA plasmid and 975 ng FokI-dCas9 expression plasmid and 100 pmol of dsODN. The three dsODNs used had either a 4-bp 5' overhang with 5' phosphorothioate linkages, a 4-bp 3' overhang with 3' phosphorothioate linkages, or were blunt with 5' and 3' phosphorothioate linkages. All dsODNs were 5' phosphorylated. Integration frequency was estimated with NdeI restriction fragment length polymorphism (RFLP) assay and quantified using capillary electrophoresis; briefly, target sites were amplified by PCRs from isolated genomic DNA. PCRs were digested with NdeI restriction enzyme (20 U) at 37° C. for 3 hours and purified with 1.8× AMPURE XP automated PCR purification. Purified cleavage products run and quantified by a QIAXCEL capillary electrophoresis instrument (Qiagen). FIG. 16A shows that blunt-ended dsODNs that were 5' phosphorylated and 3' phosphorothioated had the highest integration rates.

The same oligos (SEQ ID NOs:1 and 2) used above were transfected into U2OS cells (program DN-100) in 20 µl Solution SE (Lonza) on a Lonza Nucleofector 4-D according to the manufacturer's instructions. 500 ng of each TALEN monomer (TAL1252/TAL1301 for CCR5 and TAL2294/2295 for APC) and 100 pmol of dsODN were transfected. FIGS. 16B-C show evidence of efficient integration of a blunt, 5'-phosphorylated, 34-bp double-stranded oligodeoxynucleotide (dsODN) (oSQT685/686) into doublestranded breaks (DSBs) induced by TALENs at 2 endogenous target sites, CCR5 and APC in U2OS cells, as determined by NdeI restriction fragment length polymorphism (RFLP) analysis (described above) or T7E1 assay (briefly, target sites were amplified by PCRs from isolated genomic DNA. PCRs were purified with 1.8× AMPURE XP automated PCR purification. Purified PCR product (200 ng) was hybridized according to the following protocol: 95° C. for 5 minutes, 95-85° C. at −2° C./s, 85-25° C. at −1° C./10 s; hold at 10° C. T7 Endonuclease I (10 U) was added to the reactions, which were incubated at 37° C. for 15 minutes. The reactions were stopped by adding EDTA (25 mM) and purified with 1.8× AMPURE XP automated PCR purification. Purified cleavage products run and quantified by a QIAXCEL capillary electrophoresis instrument (Qiagen)).

Additional experiments were conducted with 2E5 U2OS-EGFP cells were nucleofected with 325 ng multiplex gRNA plasmid and 975 ng FokI-dCas9 expression plasmid and 100 pmol of dsODN. Additionally, 3E5 Mouse ES cells were nucleofected with 200 ng single gRNA plasmid and 600 ng Cas9 expression plasmid, and 100 pmol dsODN. Two dsODNs were compared: 1) blunt, phosphorylated, 5' and 3' phosphorothioate-modified and 2) blunt, phosphorylated, only 3' phosphorothioate-modified. Integration frequency was estimated with NdeI restriction fragment length polymorphism (RFLP) assay and quantified using capillary electrophesis.

The experiments, conducted with dimeric RNA-guided FokI nucleases in human U2OS cells (FIG. 17A), or with standard Cas9 in mouse ES cells (FIG. 17B), showed that the dsODNs with only 3' phosphorothioate modifications had the highest rates of integration.

Additional experiments were performed to test different concentrations of 3' phosphorothioate modified oligo in mouse ES cells. 3E5 Mouse ES cells were nucleofected with 200 ng single gRNA plasmid and 600 ng Cas9 expression plasmid, and varying amounts of dsODN as described below. Blunt, phosphorylated, only 3' phosphorothioatemodified dsODNs were used in this experiment. Annealed oligos were purified using a SEPHADEX G-25 gel filtration resin column in a comparison between purified and unpurified dsODN. dsODNs were tested at concentrations of 1, 2, 5, 10, 25, 50, and 100 pmol. Integration frequency was estimated with NdeI restriction fragment length polymorphism (RFLP) assay and quantified using capillary electrophesis. The results, shown in FIGS. 18A and 18B, indicated that 50 pmol or 100 pmol provided the best activity. Purification of the oligo through a SEPHADEX G-25 gel filtration resin column did not improve rates significantly (see FIGS. 18A and 18B). Mutagenesis frequency was estimated by T7E1 assay, which showed that the general rate of disruption was high, even in the presence of 3'-modified dsODN.

The length of the dsODNs was also evaluated. FIGS. 20A-B show that longer (e.g., 60 bp) dsODN tags integrated efficiently at sites of CRISPR-Cas9 induced DSBs. These longer dsODNs can be used to improve the accuracy of GUIDE-seq by enabling bioinformatic filtering of PCR amplification artifacts. These sequences could be recognized as any that did not contain sequences present in the longer tag.

| ssODN | Sequence | SEQ ID NO: |
|---|---|---|
| oSQT1255 | /5Phos/C*C*GCTTGCAGAGGGTATATTTGGTTAT CATATG GGACGAGTAGACTGAGATGAAGGTT*T*A | 53 |
| oSQT1256 | /5Phos/T*A*AACCTTCATCTCAGTCTACTCGTCC CATATG ATAACCAAATATACCCTCTGCAAGC*G*G | 54 |
| oSQT1257 | /5Phos/A*G*GACTGCATTCTTGTATACTTAGACT CATATG TTCCTCTGGTACCGCGTAGATGTTT*A*C | 55 |
| oSQT1258 | /5Phos/G*T*AAACATCTACGCGGTACCAGAGGAA CATATG AGTCTAAGTATACAAGAATGCAGTC*C*T | 56 |
| oSQT1259 | /5Phos/A*C*CAATCAGTCACGAGCCTAGGAGATT CATATG GGTAAGAGAGTCACATAATGCTTCC*G*G | 57 |
| oSQT1260 | /5Phos/C*C*GGAAGCATTATGTGACTCTCTTACC CATATG AATCTCCTAGGCTCGTGACTGATTG*G*T | 58 |

*indicates phosphorothioate linkage

These experiments show that the efficiency of dsODN tag uptake can be increased by using oligos that are modified only on the 3' ends rather than on both the 5' and 3' ends, that are longer, and that efficient capture of the dsODN tag occurs in a variety of cell lines, including cells that are not from a transformed cancer cell line (e.g., mouse ES cells).

Example 4

In this Example, a biotinylated version of the GUIDE-seq dsODN tag was used as a substrate for integration into the sites of genomic DSBs. As shown in Example 4, it was possible to integrate such an oligo efficiently. The experiments were performed as described above, using a biotinylated dsODN, obtained from IDT DNA.

| dsODN | Sequence | SEQ ID NO: |
|---|---|---|
| oSQT1261 | /5Phos/G*T*TTAATTGAG/iBiodT/TGTCATATG TTAATAACGGT*A*T | 59 |
| oSQT1262 | /5Phos/A*T*ACCGTTA/iBiodT/TAA CATATG ACAACTCAATTAA*A*C | 60 | iBiodT-biotin dT tag
* indicates phosphorothioate linkage

FIGS. 19A-B provide evidence for efficient integration of biotinylated dsODN tag into double-stranded breaks (DSBs) induced by Cas9 at 3 endogenous target sites, VEGFA3, EMX1, and FANCF1 in U2OS cells. This advancement could enable direct physical capture of tagged fragments by exploiting the tight binding affinity of biotin and streptavidin. (A) RFLP analysis shows % integration rates of biotinylated dsODN (oSQT1261/1262), compared to the standard dsODN (oSQT685/686) into DSBs induced by Cas9 at 3 endogenous sites, VEGFA3, EMX1, and FANCF1 in U2OS cells. (B) T7EI shows % estimated mutagenesis frequencies with biotinylated dsODN (oSQT1261/1262), compared to the standard dsODN (oSQT685/686) at 3 endogenous sites, VEGFA3, EMX1, and FANCF1 in U2OS cells.

Assuming that the biotinylation is preserved in cells, it can be used to physically pulldown DNA fragments including the biotinyulated ssODNs, and to sequence and map the captured fragments.

Example 5

In this Example, an exemplary GUIDE-Seq method is used with variant Cas9 proteins.

Variant *Streptococcus pyogenes* Cas9 (SpCas9) and *Staphylococcus aureus* Cas9 (SaCas9) proteins were generated as described in U.S. Ser. No. 61/127,634 and 62/165,517, incorporated herein by reference, and in Kleinstiver et al., "Engineered CRISPR-Cas9 nucleases with altered PAM specificities." Nature (2015) doi:10.1038/nature14592. Off-target effects were evaluated as described above.

FIG. 21 shows the number of off-target cleavage sites identified by GUIDE-seq for engineered SpCas9 variants comprising mutations at D1135V/R1335Q/T1337R (VQR variant) or D1135V/G1218R/R1335E/T1337R (VRER variant) using sgRNAs targeting EMX1, FANCF, RUNX1, VEGFA, or ZNF629 (see table 4 for sequences). This demonstrates that GUIDE-seq can also be used to profile the genome-wide specificity of engineered versions of Cas9. GUIDE-seq was also used to determine specificity profiles of the VQR and VRER SpCas9 variants in human cells by targeting endogenous sites containing NGA or NGCG PAMs.

TABLE 4

| Name | Spacer length (nt) | Spacer Sequence | SEQ ID NO: | Sequence with extended PAM | SEQ ID NO: |
|---|---|---|---|---|---|
| EMX1 NGA 4-20 | 20 | GCCACGAAGCAGGCCAATGG | 61 | GCCACGAAGCAGGCCAATGGGAG | 62 |
| FANCF NGA 1-20 | 20 | GAATCCCTTCTGCAGCACCT | 63 | GAATCCCTTCTGCAGCACCTGGAT | 64 |
| FANCF NGA 3-20 | 20 | GCGGCGGCTGCACAACCAGT | 65 | GCGGCGGCTGCACAACCAGTGGAG | 66 |
| FANCF NGA 4-20 | 20 | GGTTGTGCAGCCGCCGCTCC | 67 | GGTTGTGCAGCCGCCGCTCCAGAG | 68 |
| RUNX1 NGA 1-20 | 20 | GGTGCATTTTCAGGAGGAAG | 69 | GGTGCATTTTCAGGAGGAAGCGAT | 70 |
| RUNX1 NGA 3-20 | 20 | GAGATGTAGGGCTAGAGGGG | 71 | GAGATGTAGGGCTAGAGGGGTGAG | 72 |
| VEGFA NGA 1-20 | 20 | GCGAGCAGCGTCTTCGAGAG | 73 | GCGAGCAGCGTCTTCGAGAGTGAG | 74 |
| ZNF629 NGA 1-20 | 20 | GTGCGGCAAGAGCTTCAGCC | 75 | GTGCGGCAAGAGCTTCAGCCAGAG | 76 |
| FANCF NGCG 3-20 | 20 | GCAGAAGGGATTCCATGAGG | 77 | GCAGAAGGGATTCCATGAGGTGCG | 78 |
| FANCF NGCG 4-19 | 19 | GAAGGGATTCCATGAGGTG | 79 | GAAGGGATTCCATGAGGTGCGCG | 80 |
| RUNX1 NGCG 1-19 | 19 | GGGTGCATTTTCAGGAGGA | 81 | GGGTGCATTTTCAGGAGGAAGCG | 82 |
| VEGFA NGCG 1-20 | 20 | GCAGACGGCAGTCACTAGGG | 83 | GCAGACGGCAGTCACTAGGGGCG | 84 |
| VEGFA NGCG 2-20 | 20 | GCTGGGTGAATGGAGCGAGC | 85 | GCTGGGTGAATGGAGCGAGCAGCG | 86 |

FIG. 22 shows changes in specificity between wild-type and D1135E SpCas9 variants at off-target sites detected using an exemplary GUIDE-seq method as described herein. GUIDE-seq was also used to determine read-count differences between wild-type SpCas9 and D1135E at 3 endogenous human cell sites.

GUIDE-seq dsODN tag integration was also performed at 3 genes with wild-type and engineered Cas9 D1135E variant. The results, shown in FIGS. 23A-B, provide additional evidence that GUIDE-seq can be used to profile engineered Cas9 variants.

REFERENCES

1. Sander, J. D. & Joung, J. K. CRISPR-Cas systems for editing, regulating and targeting genomes. *Nat Biotechnol* 32, 347-355 (2014).
2. Hsu, P. D., Lander, E. S. & Zhang, F. Development and applications of CRISPR-Cas9 for genome engineering. *Cell* 157, 1262-1278 (2014).
3. Jinek, M. et al. A programmable dual-RNA-guided DNA endonuclease in adaptive bacterial immunity. *Science* 337, 816-821 (2012).
4. Fu, Y. et al. High-frequency off-target mutagenesis induced by CRISPR-Cas nucleases in human cells. *Nat Biotechnol* 31, 822-826 (2013).
5. Hsu, P. D. et al. DNA targeting specificity of RNA-guided Cas9 nucleases. *Nat Biotechnol* 31, 827-832 (2013).
6. Pattanayak, V. et al. High-throughput profiling of off-target DNA cleavage reveals RNA-programmed Cas9 nuclease specificity. *Nat Biotechnol* 31, 839-843 (2013).
7. Cradick, T. J., Fine, E. J., Antico, C. J. & Bao, G. CRISPR/Cas9 systems targeting beta-globin and CCR5 genes have substantial off-target activity. *Nucleic Acids Res* 41, 9584-9592 (2013).
8. Cho, S. W. et al. Analysis of off-target effects of CRISPR/Cas-derived RNA-guided endonucleases and nickases. *Genome Res* 24, 132-141 (2014).
9. Ghezraoui, H. et al. Chromosomal translocations in human cells are generated by canonical nonhomologous end-joining. *Mol Cell* 55, 829-842 (2014).
10. Choi, P. S. & Meyerson, M. Targeted genomic rearrangements using CRISPR/Cas technology. *Nat Commun* 5, 3728 (2014).
11. Gostissa, M. et al. IgH class switching exploits a general property of two DNA breaks to be joined in cis over long chromosomal distances. *Proc Natl Acad Sci USA* 111, 2644-2649 (2014).
12. Tsai, S. Q. & Joung, J. K. What's changed with genome editing? *Cell Stem Cell* 15, 3-4 (2014).
13. Marx, V. Gene editing: how to stay on-target with CRISPR. *Nat Methods* 11, 1021-1026 (2014).
14. Veres, A. et al. Low incidence of off-target mutations in individual CRISPR-Cas9 and TALEN targeted human stem cell clones detected by whole-genome sequencing. *Cell Stem Cell* 15, 27-30 (2014).
15. Smith, C. et al. Whole-genome sequencing analysis reveals high specificity of CRISPR/Cas9 and TALEN-based genome editing in human iPSCs. *Cell Stem Cell* 15, 12-13 (2014).

16. Duan, J. et al. Genome-wide identification of CRISPR/Cas9 off-targets in human genome. *Cell Res* 24, 1009-1012 (2014).
17. Wu, X. et al. Genome-wide binding of the CRISPR endonuclease Cas9 in mammalian cells. *Nat Biotechnol* 32, 670-676 (2014).
18. Kuscu, C., Arslan, S., Singh, R., Thorpe, J. & Adli, M. Genome-wide analysis reveals characteristics of off-target sites bound by the Cas9 endonuclease. *Nat Biotechnol* 32, 677-683 (2014).
19. Cencic, R. et al. Protospacer Adjacent Motif (PAM)-Distal Sequences Engage CRISPR Cas9 DNA Target Cleavage. *PLoS One* 9, e109213 (2014).
20. Orlando, S. J. et al. Zinc-finger nuclease-driven targeted integration into mammalian genomes using donors with limited chromosomal homology. *Nucleic Acids Res* 38, e152 (2010).
21. Schmidt, M. et al. High-resolution insertion-site analysis by linear amplification-mediated PCR (LAM-PCR). *Nat Methods* 4, 1051-1057 (2007).
22. Gabriel, R. et al. An unbiased genome-wide analysis of zinc-finger nuclease specificity. *Nat Biotechnol* 29, 816-823 (2011).
23. Jiang, W., Bikard, D., Cox, D., Zhang, F. & Marraffini, L. A. RNA-guided editing of bacterial genomes using CRISPR-Cas systems. *Nat Biotechnol* 31, 233-239 (2013).
24. Lin, Y. et al. CRISPR/Cas9 systems have off-target activity with insertions or deletions between target DNA and guide RNA sequences. *Nucleic Acids Res* 42, 7473-7485 (2014).
25. Ran, F. A. et al. Genome engineering using the CRISPR-Cas9 system. *Nat Protoc* 8, 2281-2308 (2013).
26. Heigwer, F., Kerr, G. & Boutros, M. E-CRISP: fast CRISPR target site identification. *Nat Methods* 11, 122-123 (2014).
27. Crosetto, N. et al. Nucleotide-resolution DNA double-strand break mapping by next-generation sequencing. *Nat Methods* 10, 361-365 (2013).
28. Osborn, M. J. et al. TALEN-based gene correction for epidermolysis bullosa. *Mol Ther* 21, 1151-1159 (2013).
29. Sander, J. D. et al. In silico abstraction of zinc finger nuclease cleavage profiles reveals an expanded landscape of off-target sites. *Nucleic Acids Res* (2013).
30. Fu, Y., Sander, J. D., Reyon, D., Cascio, V. M. & Joung, J. K. Improving CRISPR-Cas nuclease specificity using truncated guide RNAs. *Nat Biotechnol* 32, 279-284 (2014).
31. Tsai, S. Q. et al. Dimeric CRISPR RNA-guided FokI nucleases for highly specific genome editing. *Nat Biotechnol* 32, 569-576 (2014).
32. Guilinger, J. P., Thompson, D. B. & Liu, D. R. Fusion of catalytically inactive Cas9 to FokI nuclease improves the specificity of genome modification. *Nat Biotechnol* 32, 577-582 (2014).
33. Mali, P. et al. CAS9 transcriptional activators for target specificity screening and paired nickases for cooperative genome engineering. *Nat Biotechnol* 31, 833-838 (2013).
34. Ran, F. A. et al. Double nicking by RNA-guided CRISPR Cas9 for enhanced genome editing specificity. *Cell* 154, 1380-1389 (2013).
35. Fonfara, I. et al. Phylogeny of Cas9 determines functional exchangeability of dual-RNA and Cas9 among orthologous type II CRISPR-Cas systems. *Nucleic Acids Res* 42, 2577-2590 (2014).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting double stranded breaks (DSBs) in genomic DNA (gDNA) of a cell, the method comprising:
    contacting the cell with a blunt-ended double-stranded oligodeoxynucleotide (dsODN), wherein both strands of the dsODN are orthogonal to the genome of the cell, and further wherein (a) the 5' ends of the dsODN are phosphorylated, and (b) phosphorothioate linkages are present on both 3' ends, or phosphorothioate linkages are present on both 3' ends and both 5' ends;
    expressing or activating an exogenous engineered nuclease in the cell, for a time sufficient for the nuclease to induce DSBs in the genomic DNA of the cell, and for the cell to repair the DSBs, integrating a dsODN at one or more DSBs;
    amplifying a portion of genomic DNA comprising an integrated dsODN; and
    sequencing the amplified portion of the genomic DNA, thereby detecting a DSB in the genomic DNA of the cell.

2. The method of claim 1, wherein amplifying a portion of the genomic DNA comprises:
    fragmenting the DNA;
    ligating ends of the fragmented genomic DNA from the cell with a universal adapter; and performing polymerase chain reaction (PCR) on the ligated DNA.

3. The method of claim 1, wherein the engineered nuclease is selected from the group consisting of meganucleases, zinc-finger nucleases, transcription activator effector-like nucleases (TALEN), and Clustered Regularly Interspaced Short Palindromic Repeats (CRISPR)/Cas RNA-guided nucleases (CRISPR/Cas RGNs).

4. The method of claim 1, wherein the DSBs are off-target DSBs.

5. The method of claim 1, wherein the cell is a mammalian cell.

6. The method of claim 1, wherein the engineered nuclease is a Cas9 nuclease, and the method also includes expressing in the cells a guide RNA that directs the Cas9 nuclease to a target sequence in the genome.

7. The method of claim 1, wherein the dsODN is 30-35 nts long.

8. The method of claim 1, wherein the dsODN is phosphorylated on the 5' ends, and phosphorothioated on the 3' ends.

9. The method of claim 1, wherein the dsODN contains a randomized DNA barcode.

10. The method claim 1, comprising:
    shearing the gDNA into fragments; and
    preparing the fragments for sequencing by end-repair, a-tailing, and ligation of a single-tailed sequencing adapter.

11. The method of claim 1, wherein the dsODN is between 15 and 50 nts long.

12. A method of determining which of a plurality of guide RNAs is most specific, the method comprising:
    contacting a first population of cells with a first guide RNA and a blunt-ended double-stranded oligodeoxynucleotide (dsODN), wherein both strands of the dsODN are orthogonal to the genome of the cell, and further wherein (a) the 5' ends of the dsODN are phosphorylated, and (b) phosphorothioate linkages are present on both 3' ends, or phosphorothioate linkages are present on both 3' ends and both 5' ends;
    expressing or activating an exogenous Cas9 engineered nuclease in the first population of cells, for a time sufficient for the nuclease to induce DSBs in the genomic DNA of the cells, and for the cells to repair the DSBs, integrating a dsODN at one or more DSBs;
    amplifying a portion of genomic DNA from the first population of cells comprising an integrated dsODN;
    sequencing the amplified portion of the genomic DNA from the first population of cells;
    determining a number of sites at which the dsODN integrated into the genomic DNA of the first population of cells;
    contacting a second population of cells with a second guide RNA and a blunt-ended double-stranded oligodeoxynucleotide (dsODN), wherein both strands of the dsODN are orthogonal to the genome of the cell, and further wherein (a) the 5' ends of the dsODN are phosphorylated, and (b) phosphorothioate linkages are present on both 3' ends, or phosphorothioate linkages are present on both 3' ends and both 5' ends;
    expressing or activating an exogenous Cas9 engineered nuclease in the second population of cells, for a time sufficient for the nuclease to induce DSBs in the genomic DNA of the second population of cells, and for the cells to repair the DSBs, integrating a dsODN at one or more DSBs;

amplifying a portion of genomic DNA comprising an integrated dsODN from the second population of cells;

sequencing the amplified portion of the genomic DNA from the second population of cells;

determining a number of sites at which the dsODN integrated into the genomic DNA of the second population of cells; and comparing the number of sites at which the dsODN integrated into the genomic DNA of the first population of cells to the number of sites at which the dsODN integrated into the genomic DNA of the second population of cells to determine if the first or second guide RNA is more specific.

* * * * *

UNITED STATES PATENT AND TRADEMARK OFFICE
CERTIFICATE OF CORRECTION

PATENT NO. : 9,822,407 B2
APPLICATION NO. : 15/192753
DATED : November 21, 2017
INVENTOR(S) : J. Keith Joung and Shengdar Tsai Page 1 of 1

It is certified that error appears in the above-identified patent and that said Letters Patent is hereby corrected as shown below:

In Column 312, Line 27 (approx.), Claim 10, delete "method claim" and insert -- method of claim --

Signed and Sealed this
Twenty-second Day of May, 2018

Andrei Iancu
*Director of the United States Patent and Trademark Office*

SEQUENCE LISTING

```
<160> NUMBER OF SEQ ID NOS: 769

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-g
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (32)..(34)
<223> OTHER INFORMATION: Phosphorothioate linkage

<400> SEQUENCE: 1
gtttaattga gttgtcatat gttaataacg gtat                                 34

<210> SEQ ID NO 2
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (32)..(34)
<223> OTHER INFORMATION: Phosphorothioate linkage

<400> SEQUENCE: 2
ataccgttat taacatatga caactcaatt aaac                                  34

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagcagaag acggcatacg agattcgcct tagtgactgg agtcctctct atgggcagtc      60
ggtga                                                                 65

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caagcagaag acggcatacg agatctagta cggtgactgg agtcctctct atgggcagtc      60
ggtga                                                                 65

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caagcagaag acggcatacg agatttctgc ctgtgactgg agtcctctct atgggcagtc      60
ggtga                                                                 65

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagcagaag acggcatacg agatgctcag gagtgactgg agtcctctct atgggcagtc      60
ggtga                                                                 65
```

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caagcagaag acggcatacg agataggagt ccgtgactgg agtcctctct atgggcagtc    60
ggtga                                                               65

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caagcagaag acggcatacg agatcatgcc tagtgactgg agtcctctct atgggcagtc    60
ggtga                                                               65

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caagcagaag acggcatacg agatgtagag aggtgactgg agtcctctct atgggcagtc    60
ggtga                                                               65

<210> SEQ ID NO 10
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caagcagaag acggcatacg agatcctctc tggtgactgg agtcctctct atgggcagtc    60
ggtga                                                               65

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatgatacgg cgaccaccga gatcta                                        26

<210> SEQ ID NO 12
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 12
aatgatacgg cgaccaccga gatctacac                                          29

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcaccgact gcccatagag aggactccag tcac                                    34

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgactggag tcctctctat gggcagtcgg tgat                                    34

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: Phos-g
<220> FEATURE:
<221> NAME/KEY: misc_feature
<222> LOCATION: (12)..(14)
<223> OTHER INFORMATION: Phosphorothioate linkage

<400> SEQUENCE: 15
gatcggaaga gcca                                                          14

<210> SEQ ID NO 16
<211> LENGTH: 77
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 16
aatgatacgg cgaccaccga gatctacact agatcgcnnw nnwnnacact ctttccctac        60
```

```
acgacgctct tccgatc                                                    77
```

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 17

```
aatgatacgg cgaccaccga gatctacacc tctctatnnw nnwnnacact ctttccctac    60
acgacgctct tccgatct                                                  78
```

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 18

```
aatgatacgg cgaccaccga gatctacact atcctctnnw nnwnnacact ctttccctac    60
acgacgctct tccgatct                                                  78
```

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base

```
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 19
aatgatacgg cgaccaccga gatctacaca gagtagannw nnwnnacact ctttccctac     60
acgacgctct tccgatct                                                   78

<210> SEQ ID NO 20
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 20
aatgatacgg cgaccaccga gatctacacg taaggagnnw nnwnnacact ctttccctac     60
acgacgctct tccgatct                                                   78

<210> SEQ ID NO 21
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 21
aatgatacgg cgaccaccga gatctacaca ctgcatannw nnwnnacact ctttccctac     60
acgacgctct tccgatct                                                   78
```

<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 22
aatgatacgg cgaccaccga gatctacaca aggagtannw nnwnnacact ctttccctac    60
acgacgctct tccgatct                                                  78

<210> SEQ ID NO 23
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 23
aatgatacgg cgaccaccga gatctacacc taagcctnnw nnwnnacact ctttccctac    60
acgacgctct tccgatct                                                  78

<210> SEQ ID NO 24
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:

```
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 24
aatgatacgg cgaccaccga gatctacacg acattgtnnw nnwnnacact ctttccctac     60
acgacgctct tccgatct                                                  78

<210> SEQ ID NO 25
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 25
aatgatacgg cgaccaccga gatctacaca ctgatggnnw nnwnnacact ctttccctac     60
acgacgctct tccgatct                                                  78

<210> SEQ ID NO 26
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 26
aatgatacgg cgaccaccga gatctacacg tacctagnnw nnwnnacact ctttccctac     60
acgacgctct tccgatct                                                  78

<210> SEQ ID NO 27
<211> LENGTH: 78
```

<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 27
aatgatacgg cgaccaccga gatctacacc agagctannw nnwnnacact ctttccctac    60
acgacgctct tccgatct                                                 78

<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 28
aatgatacgg cgaccaccga gatctacacc atagtgannw nnwnnacact ctttccctac    60
acgacgctct tccgatct                                                 78

<210> SEQ ID NO 29
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

```
<220> FEATURE:
<221> NAME/KEY: misc_feature
<222> LOCATION: (77)..(78)
<223> OTHER INFORMATION: Phosphorothioate linkage

<400> SEQUENCE: 29
aatgatacgg cgaccaccga gatctacact acctagtnnw nnwnnacact ctttccctac    60
acgacgctct tccgatct                                                  78

<210> SEQ ID NO 30
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 30
aatgatacgg cgaccaccga gatctacacc gcgatatnnw nnwnnacact ctttccctac    60
acgacgctct tccgatct                                                  78

<210> SEQ ID NO 31
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (77)..(78)
<223> OTHER INFORMATION: Phosphorothioate linkage

<400> SEQUENCE: 31
aatgatacgg cgaccaccga gatctacact ggattgtnnw nnwnnacact ctttccctac    60
acgacgctct tccgatct                                                  78

<210> SEQ ID NO 32
<211> LENGTH: 41
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 32
ggatctcgac gctctcccta taccgttatt aacatatgac a                          41

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggatctcgac gctctccctg tttaattgag ttgtcatatg ttaataac                   48

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cctctctatg ggcagtcggt gatacatatg acaactcaat taaac                      45

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cctctctatg ggcagtcggt gatttgagtt gtcatatgtt aataacggta                 50

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 36
gagtccgagc agaagaagaa ngg                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 37
gggtgggggg agtttgctcc ngg                                              23
```

-continued

```
<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 38
gaccccctcc accccgcctc ngg                                             23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 39
ggtgagtgag tgtgtgcgtg ngg                                             23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 40
gtcatcttag tcattacctg ngg                                             23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 41
ggaatccctt ctgcagcacc ngg                                             23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (21)..(21)
<223> OTHER INFORMATION: a, c, t, g, unknown or other

<400> SEQUENCE: 42
gggaaagacc cagcatccgt ngg                                             23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 43
gaacacaaag catagactgc ngg                                             23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 44
ggcccagact gagcacgtga ngg                                             23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 45
ggcactgcgg ctggaggtgg ngg                                             23

<210> SEQ ID NO 46

<400> SEQUENCE: 46

000

<210> SEQ ID NO 47
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos modified a, c, t, g, unknown or other
<220> FEATURE:
<221> NAME/KEY: misc_feature
```

```
<222> LOCATION: (1)..(3)
<223> OTHER INFORMATION: Phosphorothioate linkage
<220> FEATURE:
<221> NAME/KEY: modified_base
<222> LOCATION: (2)..(4)
<223> OTHER INFORMATION: a, c, t, g, unknown or other
<220> FEATURE:
<221> NAME/KEY: misc_feature
<222> LOCATION: (36)..(38)
<223> OTHER INFORMATION: Phosphorothioate linkage

<400> SEQUENCE: 47
nnnngtttaa ttgagttgtc atatgttaat aacggtat                              38

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos modified a, c, t, g, unknown or other
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(4)
<223> OTHER INFORMATION: a, c, t, g, unknown or other
<220> FEATURE:
<221> NAME/KEY: misc_feature
<222> LOCATION: (36)..(38)
<223> OTHER INFORMATION: Phosphorothioate linkage

<400> SEQUENCE: 48
nnnnataccg ttattaacat atgacaactc aattaaac                              38

<210> SEQ ID NO 49
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-g
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (35)..(38)
<223> OTHER INFORMATION: a, c, t, g, unknown or other
<220> FEATURE:
<221> NAME/KEY: misc_feature
<222> LOCATION: (36)..(38)
<223> OTHER INFORMATION: Phosphorothioate linkage

<400> SEQUENCE: 49
gtttaattga gttgtcatat gttaataacg gtatnnnn                              38

<210> SEQ ID NO 50
<211> LENGTH: 38
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (35)..(38)
<223> OTHER INFORMATION: a, c, t, g, unknown or other
<220> FEATURE:
<221> NAME/KEY: misc_feature
<222> LOCATION: (36)..(38)
<223> OTHER INFORMATION: Phosphorothioate linkage

<400> SEQUENCE: 50
ataccgttat taacatatga caactcaatt aaacnnnn                             38

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-g
<220> FEATURE:
<221> NAME/KEY: misc_feature
<222> LOCATION: (32)..(34)
<223> OTHER INFORMATION: Phosphorothioate linkage

<400> SEQUENCE: 51
gtttaattga gttgtcatat gttaataacg gtat                                 34

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (32)..(34)
<223> OTHER INFORMATION: Phosphorothioate linkage

<400> SEQUENCE: 52
ataccgttat taacatatga caactcaatt aaac                                 34

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-c
<220> FEATURE:
<221> NAME/KEY: misc_feature
```

<222> LOCATION: (1)..(3)
<223> OTHER INFORMATION: Phosphorothioate linkage
<220> FEATURE:
<221> NAME/KEY: misc_feature
<222> LOCATION: (58)..(60)
<223> OTHER INFORMATION: Phosphorothioate linkage

<400> SEQUENCE: 53
ccgcttgcag agggtatatt tggttatcat atgggacgag tagactgaga tgaaggttta    60

<210> SEQ ID NO 54
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-t
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (58)..(60)
<223> OTHER INFORMATION: Phosphorothioate linkage

<400> SEQUENCE: 54
taaaccttca tctcagtcta ctcgtcccat atgataacca aatatacccct ctgcaagcgg    60

<210> SEQ ID NO 55
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (58)..(60)
<223> OTHER INFORMATION: Phosphorothioate linkage

<400> SEQUENCE: 55
aggactgcat tcttgtatac ttagactcat atgttcctct ggtaccgcgt agatgtttac    60

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-g
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature

```
<222> LOCATION: (58)..(60)
<223> OTHER INFORMATION: Phosphorothioate linkage

<400> SEQUENCE: 56
gtaaacatct acgcggtacc agaggaacat atgagtctaa gtatacaaga atgcagtcct    60

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (58)..(60)
<223> OTHER INFORMATION: Phosphorothioate linkage

<400> SEQUENCE: 57
accaatcagt cacgagccta ggagattcat atgggtaaga gagtcacata atgcttccgg    60

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-c
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (58)..(60)
<223> OTHER INFORMATION: Phosphorothioate linkage

<400> SEQUENCE: 58
ccggaagcat tatgtgactc tcttacccat atgaatctcc taggctcgtg actgattggt    60

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-g
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (12)..(12)
<223> OTHER INFORMATION: iBiodT
<220> FEATURE:
<221> NAME/KEY: misc_feature
```

<222> LOCATION: (32)..(34)
<223> OTHER INFORMATION: Phosphorothioate linkage

<400> SEQUENCE: 59
gtttaattga gttgtcatat gttaataacg gtat                          34

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (10)..(10)
<223> OTHER INFORMATION: iBiodT
<220> FEATURE:
<221> NAME/KEY: misc_feature
<222> LOCATION: (32)..(34)
<223> OTHER INFORMATION: Phosphorothioate linkage

<400> SEQUENCE: 60
ataccgttat taacatatga caactcaatt aaac                          34

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gccacgaagc aggccaatgg                                          20

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gccacgaagc aggccaatgg ggag                                     24

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gaatcccttc tgcagcacct                                          20

<210> SEQ ID NO 64
<211> LENGTH: 24
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 64
gaatcccttc tgcagcacct ggat            24

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
gcggcggctg cacaaccagt            20

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
gcggcggctg cacaaccagt ggag            24

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
ggttgtgcag ccgccgctcc            20

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
ggttgtgcag ccgccgctcc agag            24

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ggtgcatttt caggaggaag            20

<210> SEQ ID NO 70
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 70
ggtgcatttt caggaggaag cgat                                              24

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gagatgtagg gctagagggg                                                   20

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gagatgtagg gctagagggg tgag                                              24

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcgagcagcg tcttcgagag                                                   20

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcgagcagcg tcttcgagag tgag                                              24

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gtgcggcaag agcttcagcc                                                   20

<210> SEQ ID NO 76
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 76
gtgcggcaag agcttcagcc agag                                              24

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcagaaggga ttccatgagg                                                   20

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcagaaggga ttccatgagg tgcg                                              24

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gaagggattc catgaggtg                                                    19

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gaagggattc catgaggtgc gcg                                               23

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gggtgcattt tcaggagga                                                    19

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 82
gggtgcattt tcaggaggaa gcg                                                23

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcagacggca gtcactaggg                                                    20

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gcagacggca gtcactaggg ggcg                                               24

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gctgggtgaa tggagcgagc                                                    20

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gctgggtgaa tggagcgagc agcg                                               24

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a, c, t, g, unknown or other

<400> SEQUENCE: 87 gtgggggag tttgctccng g                                                   21

<210> SEQ ID NO 88
<211> LENGTH: 20
<212> TYPE: DNA

-continued

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a, c, t, g, unknown or other

<400> SEQUENCE: 88
gagtgagtgt gtgcgtgngg                                                   20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a, c, t, g, unknown or other

<400> SEQUENCE: 89
gtccgagcag aagaagaang g                                                 21

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gtgtgcagac ggcagtcact aggggcgct cggccaccac                              40

<210> SEQ ID NO 91
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gtgtgcagac ggcagtcata ccgttattaa catatgacaa ctcaattaaa ccactagggg       60
gcgctcggcc accac                                                        75

<210> SEQ ID NO 92
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gtgtgcagac ggcagtcgtt taattgagtt gtcatatgtt aataacggtt aactaggggg       60
cgctcggcca ccac                                                         74

<210> SEQ ID NO 93
<211> LENGTH: 74
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 93
gtgtgcagac ggcagtcata ccgttattaa catatgacaa ctcaattaaa cactagggggg    60 cgctcggcca ccac                                                       74

<210> SEQ ID NO 94
<211> LENGTH: 74
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 94
gtgtgcagac ggcagtcgtt taattgagtt gtcatatgtt aataacggta tactaggggg     60
cgctcggcca ccac                                                       74

<210> SEQ ID NO 95
<211> LENGTH: 74
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 95
gtgtgcagac ggcagtcgtt taattgagtt gtcatatgtt aataacggta tactaggggg     60
cgctcggcca ccac                                                       74

<210> SEQ ID NO 96
<211> LENGTH: 70
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 96
gtgtgcagac ggcataccgt tattaacata tgacaactca attaaacact aggggggcgct    60 cggccaccac                                                            70

<210> SEQ ID NO 97
<211> LENGTH: 74
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 97
gtgtgcagac ggcagtcgtt taattgagtt gtcatatgtt aataacggta tactaggggg     60
cgctcggcca ccac                                                       74

<210> SEQ ID NO 98
<211> LENGTH: 74
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 98

```
gtgtgcagac ggcagtcgtt taattgagtt gtcatatgtt aataacggta tactaggggg    60
cgctcggcca ccac                                                      74

<210> SEQ ID NO 99
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtgtgcagac ggcagtcata ccgttattaa catatgacaa ctcaattaaa cactaggggg    60
cgctcggcca ccac                                                      74

<210> SEQ ID NO 100
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtgtgcagac ggcagtcgtt taattgagtt gtcatatgtt aataacggta tactaggggg    60
cgctcggcca ccac                                                      74

<210> SEQ ID NO 101
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gtgtgcagac ggcagtcata ccgttattaa catatgacaa ctcaattaaa cactaggggg    60
cgctcggcca ccac                                                      74

<210> SEQ ID NO 102
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gtgtgcagac ggcagtcata ccgttattaa catatgacaa ctcaattaaa cactaggggg    60
cgctcggcca ccac                                                      74

<210> SEQ ID NO 103
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtgtgcagac ggcagtcgtt taattgagtt gtcatatgtt aataacggta tactaggggg    60
cgctcggcca ccac                                                      74
```

<210> SEQ ID NO 104
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aggggaggag gggagtctgc tccaggtttg ccctggctct                          40

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
actcggggag gggaagtttg ctcctggcat tcagtgggta                          40

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggacaggaag gaggagttag ctcctggggg gcgggattgg                          40

<210> SEQ ID NO 107
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ctggagtggg tggagtttgc tacaggcaga tgttccctgt                          40

<210> SEQ ID NO 108
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atgcgtgggg ggtgtttgct cccgggcaat gaggtaagag                          40

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tttgagggtg gggagtttac tcctggaagt agagaagaaa                          40

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaaggtgggg gtagagtttg ctccaggtgt cagaaaagac                              40

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111 aaggggtgg ggggagtttg ctcctggacc ccctatttct                               40

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atagggaggg tggagtttgc tcctggggat ggaagggccg                              40

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcacggggga gggagtttgc tcctggggaa cctgtgatcc                              40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tgtgggatgg agggagtttg ctcctggggt gtcagaatgt                              40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gttgggtaag taagggaagt ttgctcctgg tccctgctgg                              40

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
agtttagtgg agggagcttg ctcctggctg gctggagggc                40

<210> SEQ ID NO 117
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
attgctggtg ggggagcttg ctccagggaa ggaatggaag                40

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gtgggtgggg ggagtttgcc ccaggccaca ccaggagtct                40

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
ccgcctcccc cacaccccgc atccggtgtg tctccgcctg                40

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120 gaaaccccg ccatccccgc ctcaggagag tggtcctcac                40

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121 ttccccctc caccccgcc cccggcttta gggatttta                40

<210> SEQ ID NO 122

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cctgaccctg tccaccccac ctcaggacgt tctccagggg                              40

<210> SEQ ID NO 123
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgccgccccc ccaccccaac tccggagctc cccaggttgg                              40

<210> SEQ ID NO 124
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124 cgggggggccc tcccacctcg ccctggcct gtggtccctc                              40

<210> SEQ ID NO 125
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgtctccctc cccaccccac ctctgggtaa tctcttcaca                              40

<210> SEQ ID NO 126
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
caggacacac cccaccccac ctcaggtgtc ctgctgcccc                              40

<210> SEQ ID NO 127
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atgacccccc ccccaccccg ccccggcca cgcggctgac                               40

<210> SEQ ID NO 128
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cacaacaccc ccccacccca ccccaggcaa ggaatagcta                              40

<210> SEQ ID NO 129
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
caattccccc ccaccccgcc tcaggaaaga ataaacctca                              40

<210> SEQ ID NO 130
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggaacccccc ccccccccgc ccccggagac aagaccacac                              40

<210> SEQ ID NO 131
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aatcaacccc cccaccccgc ttcaggtgat tctaatgtgc                              40

<210> SEQ ID NO 132
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aggacttccc ccacaccccg ccccaggatc atctcttggg                              40

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cgcccccacc cccaccccgc ccccggtctg ctcctcctcc                              40

<210> SEQ ID NO 134
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 134
tgggtccccc tcctccctgt ctcagggtgg gcattttacc                              40

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atgaggcccc cacacccccgc ctcaggacca ctgtccatgg                             40

<210> SEQ ID NO 136
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cccctcccca cccaccccgc ctcaggcttg aagaggaaag                              40

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
accgcccccc ccaaccccgc ccccggcaac gttgctttgg                              40

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtttcatacc ccccaccccg ccccgggcag gctcgactcc                              40

<210> SEQ ID NO 139
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
aaatgcaccc cccaccccgc ccctgggtgg gttgtacaat                              40

<210> SEQ ID NO 140
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 140
aggctccccc ccctccccgc ctcgggccag ccgcggcggc                          40

<210> SEQ ID NO 141
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ggccgccccc ccaccccgcc gccggccgcc tcccgcccgc                          40

<210> SEQ ID NO 142
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tctctacccc tccaccccgc ctccgggcaa gtgaggaacc                          40

<210> SEQ ID NO 143
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
accatgcccc ctccacccca cctctgacca gaaatagcag                          40

<210> SEQ ID NO 144
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cagagacccc ccccacccca ccccaggaat cctgaaacca                          40

<210> SEQ ID NO 145
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggcggcctcc ccccacccag cctcgggccc cagtcactca                          40

<210> SEQ ID NO 146
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 146
ccgacacacc cccccccgcc tccggggttc cccgctcctc                                40

<210> SEQ ID NO 147
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ccccgacccc ctccacccg cctccgggcg cgggctccgg                                 40

<210> SEQ ID NO 148
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tgcaacctcc acctccccgc ctcaggtgat cctcccactt                                40

<210> SEQ ID NO 149
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ccctccaccc cccaccccgc cccgggtttc aagtgatttt                                40

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgaaccaccc ccaccccacc ccagggaggg aaggagcctt                                40

<210> SEQ ID NO 151
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
taaggacccc tcacacccg cccctgggtt tagagttcca                                 40

<210> SEQ ID NO 152
<211> LENGTH: 40
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 152
tgtgtacccc accacccgc cccaggtgtc aggataagga                                   40

<210> SEQ ID NO 153
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153 aaaccccct ccccgcccg cccccggcgg gggaacccaa                                    40

<210> SEQ ID NO 154
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggaccccccc accacccgc cccgggaccc tgaaagcata                                   40

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cccacaccca ccacccgcc tcagatcacc tttcactttc                                   40

<210> SEQ ID NO 156
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gacatccccc caccaccca cccccggcca ccccaagaac                                   40

<210> SEQ ID NO 157
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ttgcacaccc cccacccccg cctcaggacg tccaacaggg                                  40

<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158 tttagccaa ccccaccccg cctctggtgt cccactgagt                             40

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cctcgccctc cccattccgc cccgggctcc tccgcttatt                             40

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
agcagccgcc cccaccccgc ccccggccgc tgccatcaca                             40

<210> SEQ ID NO 161
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aggacccctc ccaccccgac tccggtggac aggcaggtaa                             40

<210> SEQ ID NO 162
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tccagtcctc caccaccccg cctctggctc cttgatcaca                             40

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163 tgtgccccccc ccaccccgcc cccggaacta aatgtagtcc                            40

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cagctgcccc cccaccccgc cactggctgc aggaattcag                                40

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tctgtccccc tcctccccac ctccggagcc tggcagtgcg                                40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ctcctacccc cactccccgc ctccggtcct cacccccttc                                40

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
aaccccccac ccccaccccg cctcagggat catgagtgcc                                40

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gccagccccc cccaccccga ctcaggacag gaggagggca                                40

<210> SEQ ID NO 169
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgtcgccctc cccaccccgc ctccggcgga cagagctggg                                40

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
atcagtcccc ccaccccacc tctggtaggc tgaactgact                    40

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tcccatcccc ctccacccca ccctggctc aggaattatg                    40

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172 aagtacccccc cccaccccgc cacaggcaca cctcatagga                   40

<210> SEQ ID NO 173
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ctaggggccc ctccaccccg cctctggcca agttttgagg                    40

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ctgaggcccc cccgccccgc ctcaggttaa gatttccaac                    40

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aagagaaggc agatccctct ccaccccacc ccaggcagga                    40

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176

-continued cctccatccc ccccacccca ccccgggatg ctgtcggggg            40

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ctgccacccc ctcccctccg cctcaggggt tccagaagcc            40

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tggagacacc ttccaccccg tctctggaaa aaacaaaaaa            40

<210> SEQ ID NO 179
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cagtctgccc ccctccccg ccccggggt cccatccctc            40

<210> SEQ ID NO 180
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagcttccct ccaccccgca tccgggagag catccaggaa            40

<210> SEQ ID NO 181
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tgagcacccc ccccccccca cctccggtca gccccaggca            40

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ggagtcactc cccaccccgc ctctggaggt gaggaggtaa            40

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tctccgcccc tgcacccagc ctccggcctc ggcaggcgct                40

<210> SEQ ID NO 184
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcaacattcc ccccacccca cctcaggcaa tcattaatct                40

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ccgttagccc ctccacccca ccacaggccc cagtgtgtga                40

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
attgggcacc ccccccccc cccgcctcag gcaaggtatt                 40

<210> SEQ ID NO 187
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cggctccccc ccaccccga cctcagggac gcccgcgggc                 40

<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188 gtgtccctc ccaccccgcc tcagaggaa gaatatgttc                  40

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aaaagacccc ccccacccog ccoccggctg ctgttgcaga                          40

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
cctttcccca ccccgccccg cctctggtcc aaccctgtct                          40

<210> SEQ ID NO 191
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
acaatgcccc ccccacccca cctctggcct gtggaaaaac                          40

<210> SEQ ID NO 192
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cttttatcct ccccacccog ccccgggtca cagggtgctg                          40

<210> SEQ ID NO 193
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cccccccccc ccccccccgc cccgggcatc tccaaactgc                          40

<210> SEQ ID NO 194
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
agggatgccc cacccccccg ccoccggctt ggcagctgcc                          40

```
<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ggccctcccc cgccaccccg ccccaggatg ggaggccaag                              40

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cccatgcccc tcccaccccg cctctgggct gagtgtagaa                              40

<210> SEQ ID NO 197
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aaagtacccc ccacaccccg cctctgggca tctgccacat                              40

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ctctcaacct cccccacccc accccaggtt cttcagtctg                              40

<210> SEQ ID NO 199
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggccccgccc ctccaccccg ccactggctc agagcaaagc                              40

<210> SEQ ID NO 200
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cccgcccacc ccaccccacc tcaggagcca ggctgagccc                              40

<210> SEQ ID NO 201
```

<210> SEQ ID NO 201
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ctgactcccc tccaccccgg ctcgggtcta tctgttgcag                              40

<210> SEQ ID NO 202
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
attaacaccc tccaccccac cacaggagtt tccttctaaa                              40

<210> SEQ ID NO 203
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ccctttcccc cccaccccaa ctcaggtgga gggggagcag                              40

<210> SEQ ID NO 204
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204 ccgcacccccc ccccccccgc ccccggccca gttcacaaga                             40

<210> SEQ ID NO 205
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
cactgccccc acccaccccg cctctggccc atgtattctg                              40

<210> SEQ ID NO 206
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
aatgcccccc accaccccac ctcgggagaa atttccactt                              40

<210> SEQ ID NO 207
<211> LENGTH: 40

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cagagagctc ccccaccccg ccccggggct ccggttcgac                              40

<210> SEQ ID NO 208
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
agccctgccc cccaccccgc cccaggggac actgggtgat                              40

<210> SEQ ID NO 209
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cccaccccca cccccacccc atctctggcg ctctttgctt                              40

<210> SEQ ID NO 210
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cactcccacc cccaccccgc cacggggtag gtacccatga                              40

<210> SEQ ID NO 211
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
agaaagaccc cccaccccgc cccaggagag atgtattttc                              40

<210> SEQ ID NO 212
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
catcaacacc ccccacccca ccccgggcac cactggcccc                              40

<210> SEQ ID NO 213
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 213
tttaccaccc ccccaccccg cccctggcag gccccagtgt                              40

<210> SEQ ID NO 214
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tcgcagaccc ccccacccca ccccaggaac catcccagag                              40

<210> SEQ ID NO 215
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
catgcgtccc ccccccccg cctcaggcgc ccccgccca                                40

<210> SEQ ID NO 216
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
cctgtccctc cccacccgc cttggggcac tctgctttgc                               40

<210> SEQ ID NO 217
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tccagccccc acctccccgc ctcgggctcc tcccgcttcg                              40

<210> SEQ ID NO 218
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tggtcaccca ctactccccg cctcaggcca cctcgggctc                              40

<210> SEQ ID NO 219
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 219
taatgccccc caccacccca cccccggctc cacatgttga                              40

<210> SEQ ID NO 220
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220 gtccccccccc ccccccgcc tccggcctcc atcccttcag                              40

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221 tgtgggggt gagtgtgtgt gtgggggggc acttgtggag                               40

<210> SEQ ID NO 222
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tctgtgtggg tgagtgtgtg tgtgtggtgg gagtgagggg                              40

<210> SEQ ID NO 223
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cttggtgagt gtgtgtgtgc atgtgggcac acacatgagt                              40

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
actaggtgag caagtgtgtg tgtgtggggc gggggagggg                              40

<210> SEQ ID NO 225
<211> LENGTH: 40
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 225
ggggtgagtc agtgtgtgag tgaggtgtgt gtgtgtgtgt                            40

<210> SEQ ID NO 226
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
agtgagtgaa tgagtgtgtg tgtgtggggt cacacgtgtg                            40

<210> SEQ ID NO 227
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tgtgcgcgag tgagtgtgtg cgcggggtgc gcgcgcgggc                            40

<210> SEQ ID NO 228
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtgagtgagt gagtgagtga gtgaggaagt agattccccc                            40

<210> SEQ ID NO 229
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
atgtgtgggt gagtgtgtgc gtgaggacat ttaagatcta                            40

<210> SEQ ID NO 230
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ggtgtgtgag tgagtgtgtg tatggggggca gtgttcgggg                           40

<210> SEQ ID NO 231
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
ggagagagag tgagtgtgtg catgaggaac tgtcaaacac                              40

<210> SEQ ID NO 232
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cttggatgag tgagtgagtg agtggggagt gtctgtgaag                              40

<210> SEQ ID NO 233
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gtgggtgagt gagtgtgtgc gtgtggggtt gagggcgttg                              40

<210> SEQ ID NO 234
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gtgagtgagt aagtgagtga gtgagggagt gagttgggat                              40

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gtgtgagtga gtgtgtgtgt gtgagagaga gagagagaga                              40

<210> SEQ ID NO 236
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
agggtagagt gagtgtgtgt gtgtggtgag aagtatgtgc                              40

<210> SEQ ID NO 237
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
agtgagcgag tgagtgtgtg tgtgggggga gtggtggtgt          40

<210> SEQ ID NO 238
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ggggtgtggg tgagtgtgtg cgtgagagcg ctcatgtggt          40

<210> SEQ ID NO 239
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
atttgttgag tgaatgtgtg cgtgaggtca ggccaagaag          40

<210> SEQ ID NO 240
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gggagtgggt gagtgagtgc gtgcgggtgg cgatgcaagc          40

<210> SEQ ID NO 241
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggtggatgac tgtgtgtgtg ggggtgtgtg ttttcacacg          40

<210> SEQ ID NO 242
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gtgagtgagt gagtgagtga gtggggttgg gggaagcaca          40

<210> SEQ ID NO 243
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243 cagggtgga tgagtgtgtg tgtggggag tgcagggtg          40

<210> SEQ ID NO 244
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
atctgtgggt gagcatgtgc gtgaggggtg cacatgtgtg          40

<210> SEQ ID NO 245
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
agggtgagtg agtgtgtgtg tgagggtgta agggtgtgtg          40

<210> SEQ ID NO 246
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ctgtgagtga gtgtgtgtgt gtgagctgag agctctgttt          40

<210> SEQ ID NO 247
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gcgtgtgagt aagtgtgtgt gtgtggaggg ggtgggaggg          40

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
agtgagtgag tgagtgtgtg tgtgggggg actcggcttg          40

<210> SEQ ID NO 249
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gcgagcgagt gggtgtgtgc gtgggggtc agccaaactt                          40

<210> SEQ ID NO 250
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
atgtgtgagt gagtgtgtgc gtgtgatcct gggtgctgcc                         40

<210> SEQ ID NO 251
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
atggggtgaa tgagtgtgtg ctctggggat ggaagaaagc                         40

<210> SEQ ID NO 252
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gtgtgtgagt gagtgtgtgt gtgtgagtgt gtgtgtgaat                         40

<210> SEQ ID NO 253
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cagggtgagt aagtgtgagc gtaagggctc tggccgagga                         40

<210> SEQ ID NO 254
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggggactgtg tgagtgtgtg cgtgaggccc tgtgcacagg                         40

<210> SEQ ID NO 255
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
atctctggag tgagtgtgtg tgtgtggaga ggggcatgtt        40

<210> SEQ ID NO 256
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
gggtgtgagt gagtgtgtgt gtgtgagtgt gtgtgtgcgc        40

<210> SEQ ID NO 257
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tatgagtgtg tgagtgtgtg cgtgtggggg aggggggtga        40

<210> SEQ ID NO 258
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
taacgctgag tgagtgtatg cgtgtggctt tagcgggaag        40

<210> SEQ ID NO 259
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cgaggtgaga gagtgtgtgc acggggccac ttctccagac        40

<210> SEQ ID NO 260
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ctggtgtgtg agtgtgtgtg tgtggtccag ggggtggtgg        40

<210> SEQ ID NO 261
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gtagaagtcc gaggagagga agaaagggtt ctggagctct        40

<210> SEQ ID NO 262
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 262
gaggaggccg agcagaagaa agacggcgac agatgttggg                40

<210> SEQ ID NO 263
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 263
cctgagtccg agcagaagaa gaagggctcc catcacatca                40

<210> SEQ ID NO 264
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 264
ggggaatcca agcaggagaa gaaggaggga aaaaccactc                40

<210> SEQ ID NO 265
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 265
atgatcatcc aagcagaaga agaagagaag gattttggca                40

<210> SEQ ID NO 266
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 266
gtcagagtta gagcagaaga agaaaggcat ggagtaaagg                40

<210> SEQ ID NO 267
<211> LENGTH: 40
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 267
acaaagtctg agcacaagaa gaatggtgag aaggaataca                40

<210> SEQ ID NO 268
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
caaaacgtct gagcagaaga agaatggaca gaactctgag          40

<210> SEQ ID NO 269
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 269
cctgagtcct agcaggagaa gaagaggcag cctagagtct          40

<210> SEQ ID NO 270
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 270
ccagagcacg agcaagagaa gaagggaggc taccacaaca          40

<210> SEQ ID NO 271
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 271
caagagtcta agcagaagaa gaagagagcc actacccaac          40

<210> SEQ ID NO 272
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 272
tgaggagtcc gggaaggaga agaaaggctc agcgcggctt          40

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 273
gggtgggggg agtttgctcc tgg          23

-continued

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gaccccctcc accccgcctc cgg                                              23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gtcatcttag tcattacctg agg                                              23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gggaaagacc cagcatccgt ggg                                              23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ggtgagtgag tgtgtgcgtg tgg                                              23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gagtccgagc agaagaagaa ggg                                              23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gaacacaaag catagactgc ggg                                              23

<210> SEQ ID NO 280

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ggcccagact gagcacgtga tgg                                               23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ggaatccctt ctgcagcacc tgg                                               23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ggcactgcgg ctggaggtgg ggg                                               23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggatggaggg agtttgctcc tgg                                               23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gggtgggggg agtttgctcc tgg                                               23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tagtggaggg agcttgctcc tgg                                               23

<210> SEQ ID NO 286
<211> LENGTH: 23
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggggagggga agtttgctcc tgg                                          23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
gggagggtgg agtttgctcc tgg                                          23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cgggggaggg agtttgctcc tgg                                          23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ctggtggggg agcttgctcc agg                                          23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gggtgggggg agtttgcccc agg                                          23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gcgtgggggg tgtttgctcc cgg                                          23

<210> SEQ ID NO 292
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 292 gtggggtag agtttgctcc agg                                              23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gagggtgggg agtttactcc tgg                                             23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ggaggagggg agtctgctcc agg                                             23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ggtgggggtg ggtttgctcc tgg                                             23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296 gaggggagc agtttgctcc agg                                              23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gagtgggtgg agtttgctac agg                                             23

<210> SEQ ID NO 298
<211> LENGTH: 23
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 298
aggtggtggg agcttgttcc tgg                                              23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gggcaagggg aggttgctcc tgg                                              23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ggtgggggag agctagctcc ggg                                              23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
aggaaggagg agttagctcc tgg                                              23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ggttgagggg agtctgctcc agg                                              23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
aagtaaggga agtttgctcc tgg                                              23

<210> SEQ ID NO 304
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 304
aggaaggagg agttagctcc tgg                                              23

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
agtgagtgag tgtgtgtgtg ggg                                              23

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
agagagtgag tgtgtgcatg agg                                              23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggtgagtgag tgtgtgcgtg tgg                                              23

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tgtgggtgag tgtgtgcgtg agg                                              23

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gctgagtgag tgtatgcgtg tgg                                              23

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 310
ggtgagtgag tgtgtgcggg tgg                                             23

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gttgagtgaa tgtgtgcgtg agg                                             23

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
agtgaatgag tgtgtgtgtg tgg                                             23

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tgtgagtaag tgtgtgtgtg tgg                                             23

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
actgtgtgag tgtgtgcgtg agg                                             23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
agcgagtggg tgtgtgcgtg ggg                                             23

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 316
agtgtgtgag tgtgtgcgtg tgg                                          23

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tgtgggtgag tgtgtgcgtg aga                                          23

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
cgcgagtgag tgtgtgcgcg ggg                                          23

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ggtgagtgag tgtgtgtgtg agg                                          23

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
ctggagtgag tgtgtgtgtg tgg                                          23

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
agcgagtgag tgtgtgtgtg ggg                                          23

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 322
ggtgagtcag tgtgtgagtg agg                                           23

<210> SEQ ID NO 323
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ggtgtgtgag tgtgtgtgtg tgg                                           23

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tgtgagtgag tgtgtgtgtg tga                                           23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tgtgagtgag tgtgtgtatg ggg                                           23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
agtgagtgag tgagtgagtg agg                                           23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
tgtgggtgag catgtgcgtg agg                                           23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
```
gtagagtgag tgtgtgtgtg tgg                                            23

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ggtggatgag tgtgtgtgtg ggg                                            23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tgtgagtgag tgtgtgcgtg tga                                            23

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
catgagtgag tgtgtgggtg ggg                                            23

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
agtgagtatg tgtgtgtgtg ggg                                            23

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gatgagtgag tgagtgagtg ggg                                            23

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tgtgagtgag tgtgtgtgtg tga                                            23

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
ggagagtgag tgtgtgtgtg aga                                            23

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ggtgagtgtg tgtgtgcatg tgg                                            23

<210> SEQ ID NO 337
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ggtgagtaag tgtgagcgta agg                                            23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
agtgagtgag tgagtgagtg ggg                                            23

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gatgagtgtg tgtgtgtgtg agg                                            23

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ggtgaatgag tgtgtgctct ggg                                            23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
agggagtgac tgtgtgcgtg tgg                                                23

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
agtgagtgag tgtgtgtgtg aga                                                23

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
ggtgagcaag tgtgtgtgtg tgg                                                23

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
cgtgagtgag tgtgtacctg ggg                                                23

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ggtggatgac tgtgtgtgtg ggg                                                23

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ggtgtatgag tgtgtgtgtg agg                                                23

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
agtgagtaag tgagtgagtg agg                                              23

<210> SEQ ID NO 348
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tgtgggtgag tgtgtgtgtg tgg                                              23

<210> SEQ ID NO 349
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tgtgagtgag tatgtacatg tgg                                              23

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tgtgagtggg tgtgtgtgtg ggg                                              23

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
aatgagtgag tgtgtgtgtg tga                                              23

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
tgtgagtgag tgtgtgtgtg tga                                              23

```
<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ggtgagagag tgtgtgcgta gga                                         23

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
agtgagaaag tgtgtgcatg cgg                                         23

<210> SEQ ID NO 355
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
agtgagtgag tgtgagtgcg ggg                                         23

<210> SEQ ID NO 356
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tgtgagtgag tgtgtgtgtg tga                                         23

<210> SEQ ID NO 357
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
agtgagtgag tgtgtgtgtg tga                                         23

<210> SEQ ID NO 358
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ggagagtgag tgtgtgcatg tgc                                         23

<210> SEQ ID NO 359
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ggtgtgtggg tggggtgtg tgg                                             23

<210> SEQ ID NO 360
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
tgtgagagag tgtgtgtgtg gag                                            23

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
agggagtgag tgtgagagtg cgg                                            23

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
ggtgagagag tgtgtgcacg ggg                                            23

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
tgtgagagag agtgtgcgtg tgg                                            23

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364 gggggtgag tgtgtgtgtg ggg                                             23

<210> SEQ ID NO 365
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
ctacccctcc acccgcctc cgg                                              23

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366 attcccccc acccgcctc agg                                               23

<210> SEQ ID NO 367
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
acaccccccc acccgcctc agg                                              23

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368 tgccccccc accccacctc tgg                                              23

<210> SEQ ID NO 369
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369 ctccccccc accccgcctc agg                                              23

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gcttccctcc acccgcatc cgg                                              23

<210> SEQ ID NO 371
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 371
taccccccac accccgcctc tgg                                              23

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
tgcccctccc accccgcctc tgg                                              23

<210> SEQ ID NO 373
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
gacccctccc accccgactc cgg                                              23

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gtaccccacc accccgcccc agg                                              23

<210> SEQ ID NO 375
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
cccccccccc ccccgcctc cgg                                               23

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
ccccaccccc accccgcctc agg                                              23

<210> SEQ ID NO 377
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 377
cacccccccc ccccaccctc cgg                                              23

<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
cctcccccac accccgcatc cgg                                              23

<210> SEQ ID NO 379
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379 cccctcccc gccccgcccc cgg                                               23

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gaccccctcc accccgcctc cgg                                              23

<210> SEQ ID NO 381
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gggcccctcc accccgcctc tgg                                              23

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
cgccctcccc accccgcctc cgg                                              23

<210> SEQ ID NO 383
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 383
gacacacccc accccacctc agg                                              23

<210> SEQ ID NO 384
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gaccccaccc accccgcccc cgg                                              23

<210> SEQ ID NO 385
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tcccccccac ccccacctc agg                                               23

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gacaccttcc accccgtctc tgg                                              23

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
gcccccaccc accccgcctc tgg                                              23

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388 catcccccc accccacccc ggg                                               23

<210> SEQ ID NO 389
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 389 ctgcccccccc accccgccac tgg                                              23

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
cccccccccc ccccgcctc agg                                                23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391 gcccccacc accccacctc ggg                                                23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
cccccccccc ccccgcccc ggg                                                23

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
tgcccccccc accccgcccc cgg                                               23

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
cttcccccac accccgcccc agg                                               23

<210> SEQ ID NO 395
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 395
aggccccccc gccccgcctc agg                                              23

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
tacccccccc accccgccac agg                                              23

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
catacccccc accccgcccc ggg                                              23

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
cgccctcccc actccgcctc ggg                                              23

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gagctccccc accccgcccc ggg                                              23

<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gacccctcac accccgcccc tgg                                              23

<210> SEQ ID NO 401
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 401
cccccccacc accccgcccc ggg                                              23

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
ctcccccgcc accccgcccc agg                                              23

<210> SEQ ID NO 403
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403 ccacccccccc accccgcccc tgg                                             23

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
tccacccccc accccgcccc ggg                                              23

<210> SEQ ID NO 405
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gaccctgtcc accccacctc agg                                              23

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406 cactccccccc accccgcccc agg                                             23

<210> SEQ ID NO 407
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
agcccccccc accccgactc agg                                            23

<210> SEQ ID NO 408
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
cattcccccc accccacctc agg                                            23

<210> SEQ ID NO 409
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
cccccccccc gccccgcccc ccg                                            23

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410 atcccctcc accccacccc tgg                                             23

<210> SEQ ID NO 411
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
caaccccccc accccgcttc agg                                            23

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
cccccccccc accccgcccc cgg                                            23

<210> SEQ ID NO 413
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ccaccccccc accccgcccc agg                                               23

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ctccctcccc accccaccct tgg                                               23

<210> SEQ ID NO 415
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
aggcccccac accccgcctc agg                                               23

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416 gccccccccca accccgcccc cgg                                              23

<210> SEQ ID NO 417
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
accccccccc ccccgcccc cgg                                                23

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
cacccactac tccccgcctc agg                                               23

<210> SEQ ID NO 419
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419 cagtccccccc accccaccct tgg                                              23

<210> SEQ ID NO 420
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420 aagaccccc accccgcccc agg                                         23

<210> SEQ ID NO 421
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
ccgccccccc accccgccgc cgg                                        23

<210> SEQ ID NO 422
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422 aaccacccc accccacccc agg                                         23

<210> SEQ ID NO 423
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423 ctccccccc tccccgcctc ggg                                         23

<210> SEQ ID NO 424
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gtcactcccc accccgcctc tgg                                        23

<210> SEQ ID NO 425
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gtcctccacc accccgcctc tgg                                        23

<210> SEQ ID NO 426
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gaccccacct accccacctc agg                                              23

<210> SEQ ID NO 427
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427 gcccccacc accccacccc cgg                                               23

<210> SEQ ID NO 428
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
gggccctccc acctcgcccc tgg                                              23

<210> SEQ ID NO 429
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429 ctcaccccccc accccacctc tgg                                             23

<210> SEQ ID NO 430
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430 gtcccctcc tccccacctc cgg                                               23

<210> SEQ ID NO 431
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
atgccccacc ccccgcccc cgg                                               23

<210> SEQ ID NO 432
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gtccctcccc acccgccttt ggg                                           23

<210> SEQ ID NO 433
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
aacaccctcc accccaccac agg                                           23

<210> SEQ ID NO 434
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
gccgcccccc actccgcctc cgg                                           23

<210> SEQ ID NO 435
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ttctccctcc tcccgcctc ggg                                            23

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436 ctaccccac tcccgcctc cgg                                             23

<210> SEQ ID NO 437
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437 aagcccccc accccgcccc ggg                                            23

<210> SEQ ID NO 438

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
ccgcccctcc accccgccac tgg                                            23

<210> SEQ ID NO 439
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tatcctcccc accccgcccc ggg                                            23

<210> SEQ ID NO 440
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
tgcacccccc accccgcccc tgg                                            23

<210> SEQ ID NO 441
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
actcccctcc accccggctc ggg                                            23

<210> SEQ ID NO 442
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
atccctctcc accccacccc agg                                            23

<210> SEQ ID NO 443
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443 tgcccctct ccccgccccc gg                                              22

<210> SEQ ID NO 444
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
agccaacccc accccgcctc tgg                                            23

<210> SEQ ID NO 445
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
agcccccacc tccccgcctc ggg                                            23

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
aaccccaccc accccatctc agg                                            23

<210> SEQ ID NO 447
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
tcccaccccc accccgccac ggg                                            23

<210> SEQ ID NO 448
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tccccacccc gccccgcctc tgg                                            23

<210> SEQ ID NO 449
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
gacccctacc accccatctc agg                                            23

<210> SEQ ID NO 450
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 450
acaccccccc accccacccc agg                                              23

<210> SEQ ID NO 451
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ccgccccccc accccaactc cgg                                              23

<210> SEQ ID NO 452
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
aacctccccc accccacccc agg                                              23

<210> SEQ ID NO 453
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
gtccctcccc accccgcctc cag                                              23

<210> SEQ ID NO 454
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
tggcccctcc gccccacctc tgg                                              23

<210> SEQ ID NO 455
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
caccccctcc cctccgcctc agg                                              23

<210> SEQ ID NO 456
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 456
cccccctccc accccgcctc tag                                            23

<210> SEQ ID NO 457
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
agaccccccc accccacccc agg                                            23

<210> SEQ ID NO 458
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458 ctaccectcc accccgactc gga                                            23

<210> SEQ ID NO 459
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
cacacccacc accccgcctc aga                                            23

<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ggcccactcc actccgtctc cgg                                            23

<210> SEQ ID NO 461
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
acgccccccc accccacgtc tgg                                            23

<210> SEQ ID NO 462
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 462
cgcccacccc accccacctc agg                                                23

<210> SEQ ID NO 463
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
caccccccgc accccgcccc agg                                                23

<210> SEQ ID NO 464
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
ccaccatccc accccgcctc tgg                                                23

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
aacctccacc tccccgcctc agg                                                23

<210> SEQ ID NO 466
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
gacacacccc ccccgcctc cgg                                                 23

<210> SEQ ID NO 467
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467 gccaccccc accccacccc agg                                                 23

<210> SEQ ID NO 468
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 468
ccccaccccc acccgcccc cgg                                              23

<210> SEQ ID NO 469
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
aggccctccc accccgcatc agg                                             23

<210> SEQ ID NO 470
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cacctccaca actccgcctc tgg                                             23

<210> SEQ ID NO 471
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tctcccctcc accccgccct cgg                                             23

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tactcccccc acccagcctc agg                                             23

<210> SEQ ID NO 473
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
tcccccctcc acccccgccc ccg                                             23

<210> SEQ ID NO 474
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
actcccctcc acccccacctc tga                        23

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
cacccccccc ccccgcccc cgg                          23

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
agccgccccc accccgcccc cgg                         23

<210> SEQ ID NO 477
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477 tcccccacc accccacccc cgg                          23

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478 gcctccccccc acccagcctc ggg                        23

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
aacacccccc accccacccc ggg                         23

<210> SEQ ID NO 480
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ccccaccccc accccgcctc cag                                           23

<210> SEQ ID NO 481
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
ggccccaccc accccgcctt ctg                                           23

<210> SEQ ID NO 482
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
ccgcccctgc acccagcctc cgg                                           23

<210> SEQ ID NO 483
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483 cacccccgccc accccgcccc tgg                                          23

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484 cccctcccc accccgccgc agg                                            23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
cgtccccccc ccccgcctc agg                                            23

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486 ccgcccccccc atcccgcccc agg                                        23

<210> SEQ ID NO 487
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
agtcccatcc accccgccta agg                                         23

<210> SEQ ID NO 488
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
accccacccc accccgtctc cgg                                         23

<210> SEQ ID NO 489
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489 ctcccctcc accccacctc cag                                          23

<210> SEQ ID NO 490
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gacccccccc ccccgccccc ggg                                         23

<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
cccccccccc ccccgccccc ggg                                         23

<210> SEQ ID NO 492
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
agtagccccc accccgcctc ggg                                              23

<210> SEQ ID NO 493
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
tagcccctcc accccaccac agg                                              23

<210> SEQ ID NO 494
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
gaccccaccc accccgccgc agg                                              23

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
ggctccctcc gccccgcccc ggg                                              23

<210> SEQ ID NO 496
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
ttccccttcc acccagcctc tgg                                              23

<210> SEQ ID NO 497
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
gccacccacc accccacctc agg                                              23

<210> SEQ ID NO 498
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
aaccctctcc acccagtctc agg                                              23

<210> SEQ ID NO 499
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ggctcacccc accccacctc tgg                                            23

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500 gaccccccccc accccacccc agg                                           23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501 tgcccctcc accccacctc tga                                             23

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502 gtcccctcc tccccgtctc agg                                             23

<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
ggccctctcc actccacctc agg                                            23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
cccccccctc acccgcccc tgg                                             23

```
<210> SEQ ID NO 505
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505 ccccacccce accccacctc tgg                                              23

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
tttccccccc accccaactc agg                                              23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507 gtccectccc tccccgcctc tgg                                              23

<210> SEQ ID NO 508
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508 ccaccectcc accccgtccc agg                                              23

<210> SEQ ID NO 509
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
ctccccctac accccgcaac agg                                              23

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tcctccttcc actccgcctc tgg                                              23
```

```
<210> SEQ ID NO 511
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511 gaccccttc accccaccta tgg                                          23

<210> SEQ ID NO 512
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512 cctgccccc accccgcccc agg                                          23

<210> SEQ ID NO 513
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
ttccccccca accccacctc ggg                                         23

<210> SEQ ID NO 514
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514 cccccctcc accccacttc agg                                          23

<210> SEQ ID NO 515
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515 agccccccc tccccgcccc agg                                          23

<210> SEQ ID NO 516
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
cagcccctcc actccacccc cgg                                         23

<210> SEQ ID NO 517
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
gagtccgagc agaagaagaa ggg                                          23

<210> SEQ ID NO 518
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
gagttagagc agaagaagaa agg                                          23

<210> SEQ ID NO 519
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
gagtctaagc agaagaagaa gag                                          23

<210> SEQ ID NO 520
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gaggccgagc agaagaaaga cgg                                          23

<210> SEQ ID NO 521
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
gagtcctagc aggagaagaa gag                                          23

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
aagtctgagc acaagaagaa tgg                                          23

<210> SEQ ID NO 523
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gagtccggga aggagaagaa agg                                              23

<210> SEQ ID NO 524
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
gagccggagc agaagaagga ggg                                              23

<210> SEQ ID NO 525
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
aagtccgagg agaggaagaa agg                                              23

<210> SEQ ID NO 526
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gaatccaagc aggagaagaa gga                                              23

<210> SEQ ID NO 527
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
acgtctgagc agaagaagaa tgg                                              23

<210> SEQ ID NO 528
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
gagtaggagc aggagaagaa gga                                              23

<210> SEQ ID NO 529
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 529
aagtcccggc agaggaagaa ggg                                             23

<210> SEQ ID NO 530
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
tcatccaagc agaagaagaa gag                                             23

<210> SEQ ID NO 531
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
gagtctaagc aggagaataa agg                                             23

<210> SEQ ID NO 532
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gagcacgagc aagagaagaa ggg                                             23

<210> SEQ ID NO 533
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
ggaatccctt ctgcagcacc tgg                                             23

<210> SEQ ID NO 534
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ggaaccccgt ctgcagcacc agg                                             23

<210> SEQ ID NO 535
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 535
ggagtccctc ctacagcacc agg                                              23

<210> SEQ ID NO 536
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
agaggcccct ctgcagcacc agg                                              23

<210> SEQ ID NO 537
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
accatccctc ctgcagcacc agg                                              23

<210> SEQ ID NO 538
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ggattgccat ccgcagcacc tgg                                              23

<210> SEQ ID NO 539
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
tgaatcccat ctccagcacc agg                                              23

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ggagtccctc ctacagcacc agg                                              23

<210> SEQ ID NO 541
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 541
ggagtccctc ctgcagcacc tga                                          23

<210> SEQ ID NO 542
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
gggaaagacc cagcatccgt ggg                                          23

<210> SEQ ID NO 543
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
gggaaagtcc cagcatcctt tgg                                          23

<210> SEQ ID NO 544
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
gggaaaagcc cagcatccct tgg                                          23

<210> SEQ ID NO 545
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
gggaaggacc cagcatcctg ggg                                          23

<210> SEQ ID NO 546
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
gggaaatacc cagcatccaa tgg                                          23

<210> SEQ ID NO 547
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 547
caagaagacc cagcttccgt agg                                          23

<210> SEQ ID NO 548
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gagaaaagcc cagcatcctt agg                                          23

<210> SEQ ID NO 549
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
ggaaaagacc aagcatcagt ggg                                          23

<210> SEQ ID NO 550
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
atgaaagacc cagcatccat tga                                          23

<210> SEQ ID NO 551
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
gggaaggacc cagcattcct ggg                                          23

<210> SEQ ID NO 552
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
gaacacaaag catagactgc ggg                                          23

<210> SEQ ID NO 553
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 553
gaacacaatg catagattgc cgg                                              23

<210> SEQ ID NO 554
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
aaacataaag catagactgc aaa                                              23

<210> SEQ ID NO 555
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
ggcccagact gagcacgtga tgg                                              23

<210> SEQ ID NO 556
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
cacccagact gagcacgtgc tgg                                              23

<210> SEQ ID NO 557
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
gacacagact gggcacgtga ggg                                              23

<210> SEQ ID NO 558
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
agctcagact gagcaagtga ggg                                              23

<210> SEQ ID NO 559
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 559
agaccagact gagcaagaga ggg                                          23

<210> SEQ ID NO 560
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
gagccagaat gagcacgtga ggg                                          23

<210> SEQ ID NO 561
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
tgcactgcgg ccggaggagg tgg                                          23

<210> SEQ ID NO 562
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
ggctctgcgg ctggagggg tgg                                           23

<210> SEQ ID NO 563
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
ggcacgacgg ctggaggtgg ggg                                          23

<210> SEQ ID NO 564
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
ggcatcacgg ctggaggtgg agg                                          23

<210> SEQ ID NO 565
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
```

```
ggcactgcgg ctggaggtgg ggg                                            23
```

<210> SEQ ID NO 566
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566

```
ggcgctgcgg cgggaggtgg agg                                            23
```

<210> SEQ ID NO 567
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567

```
ggcactgaga ctgggggtgg ggg                                            23
```

<210> SEQ ID NO 568
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568

```
agcagtgcgg ctagaggtgg tgg                                            23
```

<210> SEQ ID NO 569
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569

```
ggcactgctg ctgggggtgg tgg                                            23
```

<210> SEQ ID NO 570
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570

```
ggcactgggg ctgggggagg ggg                                            23
```

<210> SEQ ID NO 571
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
ggcactgggg ttggaggtgg ggg                                              23

<210> SEQ ID NO 572
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
aggactgcgg ctgggggtgg tgg                                              23

<210> SEQ ID NO 573
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
ggcactgagg gtggaggtgg ggg                                              23

<210> SEQ ID NO 574
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
gacaccacgg ctggagatgg tgg                                              23

<210> SEQ ID NO 575
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
ggcactgtgg ctgcaggtgg agg                                              23

<210> SEQ ID NO 576
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
agcactgtgg ctgggggagg ggg                                              23

<210> SEQ ID NO 577
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
ggcaatgtgg ctgaaggtgg ggg                                              23

<210> SEQ ID NO 578
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
ggcacagcag ctggaggtgc tgg                                              23

<210> SEQ ID NO 579
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
gccactgggg ctgggggtgg ggg                                              23

<210> SEQ ID NO 580
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
tgcactgtgg ctggagatgg ggg                                              23

<210> SEQ ID NO 581
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
ggctctgtgg ctggaggagg tgg                                              23

<210> SEQ ID NO 582
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
gccactgcag ctagaggtgg agg                                              23

<210> SEQ ID NO 583
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
ggcactgcgg gtggaggcgg ggg                                              23

<210> SEQ ID NO 584
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
agcactgtgc ctgggggtgg ggg                                            23

<210> SEQ ID NO 585
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
ggcaatgcgg ctggaggcgg agg                                            23

<210> SEQ ID NO 586
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
gaggctgcgg ctgggggtgg agg                                            23

<210> SEQ ID NO 587
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
ggctccgcag ctggaggtgg ggg                                            23

<210> SEQ ID NO 588
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
agcactgtgg ctgggggagg cgg                                            23

<210> SEQ ID NO 589
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
gtcactgcag ctggaggagg ggg                                            23

```
<210> SEQ ID NO 590
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
ggctctgagg ccagaggtgg tgg                                              23

<210> SEQ ID NO 591
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
agcacggcag ctggaggagg ggg                                              23

<210> SEQ ID NO 592
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
agcactgcag ctgggagtgg agg                                              23

<210> SEQ ID NO 593
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
gggactgcgg ctggaggtgg gaa                                              23

<210> SEQ ID NO 594
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
ggcactgctg ctagaggtgc agg                                              23

<210> SEQ ID NO 595
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
ggctgtgcgg ccagaggtgg agg                                              23

<210> SEQ ID NO 596
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
gacactgagg caggaggtgg ggg                                              23

<210> SEQ ID NO 597
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
ggcacaatgg ctggaggtga agg                                              23

<210> SEQ ID NO 598
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
agcactgggg ctgggggagg ggg                                              23

<210> SEQ ID NO 599
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
gacaccgtga ctggaggtgg agg                                              23

<210> SEQ ID NO 600
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
ggcactgcca ctgggggtga ggg                                              23

<210> SEQ ID NO 601
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
cacactgcag ctggaggtgg tgg                                              23

<210> SEQ ID NO 602
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
agcactgcag atggaggagg cgg                                          23

<210> SEQ ID NO 603
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
ggctctgtgg ccggaggagg cgg                                          23

<210> SEQ ID NO 604
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ggcacttcgg ttggggtgg ggg                                           23

<210> SEQ ID NO 605
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
gccactgcga ctggaggagg ggg                                          23

<210> SEQ ID NO 606
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ggcgctgcgg ccggaggtgg ggc                                          23

<210> SEQ ID NO 607
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
cccactgggg ctggaggtgg ggg                                          23

<210> SEQ ID NO 608
<211> LENGTH: 23
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 608
ggtactctgg ctggaggtgg tgg                                    23

<210> SEQ ID NO 609
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 609
ggcactgcag cctggggtg ggg                                     23

<210> SEQ ID NO 610
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 610
ggaactgtgg ctggaggtgg cag                                    23

<210> SEQ ID NO 611
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 611
gccacagcgg ccggaggtgg cag                                    23

<210> SEQ ID NO 612
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 612
gccactgtgg ctggaggtgg gga                                    23

<210> SEQ ID NO 613
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 613
ggcacggagg ctggaagtgg ggg                                    23

<210> SEQ ID NO 614
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 614
ggcactgggg caggagatgg ggg                                           23

<210> SEQ ID NO 615
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
ggcactgaat ctggaggtgg ggg                                           23

<210> SEQ ID NO 616
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
gtcactgcgg ctgcagatgg cgg                                           23

<210> SEQ ID NO 617
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ggctcttcgg ctggaggtag cgg                                           23

<210> SEQ ID NO 618
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
ggtacagcgg ctgggggagg cgg                                           23

<210> SEQ ID NO 619
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
tggactgcgg ctggagaggg agg                                           23

<210> SEQ ID NO 620
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 620
ggcaccgcgg ccggagctgt ggg                                          23

<210> SEQ ID NO 621
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
ggcacagcag gtggaggtgg agg                                          23

<210> SEQ ID NO 622
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
agcactgtag caagaggtgg agg                                          23

<210> SEQ ID NO 623
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
ggcactgaga ccagaggtgg tgg                                          23

<210> SEQ ID NO 624
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
gacactgcag ctggaggtgg ggt                                          23

<210> SEQ ID NO 625
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
gacacaacgg caggaggtgg cgg                                          23

<210> SEQ ID NO 626
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 626
ggcgctgcgg ctggagccgg cgg                                         23

<210> SEQ ID NO 627
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
cagactgcgg caggggtgg cgg                                          23

<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gacacagtgg ctggaggtgt ggg                                         23

<210> SEQ ID NO 629
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
gtaactgcgg ctggcggtgg tgg                                         23

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
ggcactctgg ctggagctgg ggg                                         23

<210> SEQ ID NO 631
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ggccctgggg ctggaggtgt tgg                                         23

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 632
agcactgggg atggaggtgt agg                                               23

<210> SEQ ID NO 633
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
aacactgtgg ccgggggtgg tgg                                               23

<210> SEQ ID NO 634
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
ggcagggcgg ctggaggagg tgg                                               23

<210> SEQ ID NO 635
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
ggggctgcgg ccggaggtgg tgg                                               23

<210> SEQ ID NO 636
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
ggcactgcag acggaggtgt ggg                                               23

<210> SEQ ID NO 637
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
tacactgcgg ccgggagtgg tgg                                               23

<210> SEQ ID NO 638
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 638
ggcactgggg ctggggtgc agg                                            23

<210> SEQ ID NO 639
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
gccaccgcgg caggaggcgg agg                                           23

<210> SEQ ID NO 640
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
ggcactgtgg caagaggtgg gag                                           23

<210> SEQ ID NO 641
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
ggcactgcgg gaggaggtgg gcg                                           23

<210> SEQ ID NO 642
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
ggcgcagcgg ctggaggagg tgc                                           23

<210> SEQ ID NO 643
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
ggccctgcgg ctggagatat ggg                                           23

<210> SEQ ID NO 644
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
```

-continued agcacagcgg ctggagaagg cag                                            23

<210> SEQ ID NO 645
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ggcactgcag cagggatgg ggg                                             23

<210> SEQ ID NO 646
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
tgcactgcag ctgcaggtgg agg                                            23

<210> SEQ ID NO 647
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
agcactgcgc ttggggtgg ggg                                             23

<210> SEQ ID NO 648
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
ggaacggcgg ccggaggtgt agg                                            23

<210> SEQ ID NO 649
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
ggcactgggg ctggagacgg ggg                                            23

<210> SEQ ID NO 650
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650

-continued gacactaggg caggaggtgg agg                                                23

<210> SEQ ID NO 651
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
ggcactgaga aaggaggtgg agg                                                23

<210> SEQ ID NO 652
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
ggcacagggg ctgaaggtga tgg                                                23

<210> SEQ ID NO 653
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ggcactgggt ctgaaggtgg agg                                                23

<210> SEQ ID NO 654
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
gacactgtgg ctggaagtgg aag                                                23

<210> SEQ ID NO 655
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
cccactgtgg ctggaggtgt ggg                                                23

<210> SEQ ID NO 656
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
ggcactacag ctggaggtgg caa                                                23

<210> SEQ ID NO 657
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
tgctctgcgg caggaggagg agg                                           23

<210> SEQ ID NO 658
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
aagactgggg ctggaggtgg ggg                                           23

<210> SEQ ID NO 659
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
ggcagtccgg atggaggtgg ggg                                           23

<210> SEQ ID NO 660
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
agcacagagg ctggaggtgg ggt                                           23

<210> SEQ ID NO 661
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
ggcactgcgg ccagagggag cgg                                           23

<210> SEQ ID NO 662
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
gacactaagg ctggaggtgg gga                                           23

<210> SEQ ID NO 663
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
ggcagtgcgg ctggagctgc ggg                                           23

<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
agcaccgctg ctgggggcgg ggg                                           23

<210> SEQ ID NO 665
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
ggccctgcgg ccgggggtgg aga                                           23

<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
agctctgtgg ctggaggtgt gag                                           23

<210> SEQ ID NO 667
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
ggcactgggg caggagttgg ggg                                           23

<210> SEQ ID NO 668
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
ggcactggga atggaggttg ggg                                           23

```
<210> SEQ ID NO 669
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
agcacagcag ctgcaggtgg ggg                                              23

<210> SEQ ID NO 670
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
ggcactgagg ccggaggagg aag                                              23

<210> SEQ ID NO 671
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
agcactgggg ccagaggtga ggg                                              23

<210> SEQ ID NO 672
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
tgcaccgcgg ctggggctgg agg                                              23

<210> SEQ ID NO 673
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
caggctgcgc ctggaggtgg ggg                                              23

<210> SEQ ID NO 674
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
agcactgcag cgggaggtga gag                                              23

<210> SEQ ID NO 675
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
ggcaccttgg ctgaaggtgg ggg                                              23

<210> SEQ ID NO 676
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
ggcaccgagg ccggaggtgc tgg                                              23

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
gccactgggg ctggaggggg agg                                              23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
agcaccatgg ctagaggtgt ggg                                              23

<210> SEQ ID NO 679
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
agcacagcga ctgaaggtga ggg                                              23

<210> SEQ ID NO 680
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
ggcgctgcgg cccgaggggg tgg                                              23

<210> SEQ ID NO 681
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
ggcaccaggc ctggaggtgt ggg                                           23

<210> SEQ ID NO 682
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
agaactgctg ctggaggtgg tgg                                           23

<210> SEQ ID NO 683
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
gccactgagg ccggaggtgg aga                                           23

<210> SEQ ID NO 684
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gctgctgcgg ctggaggtgg gga                                           23

<210> SEQ ID NO 685
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
ggcactgagg ctgcaggcgg cgg                                           23

<210> SEQ ID NO 686
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
gccactgggc ctggggtgg ggg                                            23

<210> SEQ ID NO 687
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 687
gggcacgcgg ctggaggagg ggg                                    23

<210> SEQ ID NO 688
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
agcactgtta caggaggtgg ggg                                    23

<210> SEQ ID NO 689
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
ggcactgcag ctggcggtgc tgg                                    23

<210> SEQ ID NO 690
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
cacactgcgg ccggaggtga ccg                                    23

<210> SEQ ID NO 691
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
ggcactgcaa ctggaagtga tgg                                    23

<210> SEQ ID NO 692
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
ggcacagggg ctggaggtgg ggc                                    23

<210> SEQ ID NO 693
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
gggcatgcgg ctggaagtgg tgg                                          23

<210> SEQ ID NO 694
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
gacactgcct ctgggggtgg ggg                                          23

<210> SEQ ID NO 695
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
gtcatcttag tcattacctg agg                                          23

<210> SEQ ID NO 696
<211> LENGTH: 55
<212> TYPE: DNA
<213> ORGANISM: Homo sapiens

<400> SEQUENCE: 696
tcagaaatag ggggtccagg agcaagctcc ctccactaaa ctcctgcagc actgt        55

<210> SEQ ID NO 697
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
tcagaaatag ggggtccagc aagctccctc cactaaactc ctgcag                 46

<210> SEQ ID NO 698
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
tcagaaatag ggggtccctc cactaaactc ctgcagcact gt                     42

<210> SEQ ID NO 699
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
tcagaaatag ggggtccact aaactcctgc agcactgt                                    38

<210> SEQ ID NO 700
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700 ggggaaata                                                                    9

<210> SEQ ID NO 701
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
cctccactaa actcctgcag cactgt                                                 26

<210> SEQ ID NO 702
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
tcagaaatag ggggtcc                                                           17

<210> SEQ ID NO 703
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703 ctgccatc                                                                     8

<210> SEQ ID NO 704
<211> LENGTH: 55
<212> TYPE: DNA
<213> ORGANISM: Homo sapiens

<400> SEQUENCE: 704
ctgccctcca gccagccagg agcaaactcc ccccacccc tttccaaagc ccatt                  55

<210> SEQ ID NO 705
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
ttgccctccc gccagccaaa ctccccccac cccctttcca aacctcatt                        49

<210> SEQ ID NO 706
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
ctgccctcca gccagctccc cccacccct ttccaaagcc catt                        44

<210> SEQ ID NO 707
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
ctgccctcca gcccctttcc aaagcccatt                                       30

<210> SEQ ID NO 708
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708 ccaccctc                                                                8

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709 cccctttcc aaagcccatt                                                   20

<210> SEQ ID NO 710
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710 tcccctc                                                                 8

<210> SEQ ID NO 711
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
cccaccccct ttccaaagcc catt                                             24

<210> SEQ ID NO 712
<211> LENGTH: 55
<212> TYPE: DNA
<213> ORGANISM: Homo sapiens

<400> SEQUENCE: 712
gaagctgagc tgccctccag ccagccagga tcctggaccc cctatttctg acctc    55

<210> SEQ ID NO 713
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
gaagctgagc tgccctccag ccagtcctgg accccctatt tctgacctc    49

<210> SEQ ID NO 714
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
gaagctgagc tgccctccag ccagcctgga ccccctattt ctgacctc    48

<210> SEQ ID NO 715
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
gaagctgagc tgcccctgg accccctatt tctgacctc    39

<210> SEQ ID NO 716
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
gaagctgagc tgccctccag cccctatttc tgacctc    37

<210> SEQ ID NO 717
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
gaagctgagc tgccctggac cccctatttc tgacctc    37

<210> SEQ ID NO 718
<211> LENGTH: 55
<212> TYPE: DNA
<213> ORGANISM: Homo sapiens -continued

<400> SEQUENCE: 718
tttggaaagg gggtgggggg agtttgcgca agctccctcc actaaactcc tgcag    55

<210> SEQ ID NO 719
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
tttggaaagg gggtgggggg agtttagctc cctacactaa actcctgcag    50

<210> SEQ ID NO 720
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
tttggaaagg gggtgggggg cag    23

<210> SEQ ID NO 721
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
tttggaaagg gggtggggg    19

<210> SEQ ID NO 722
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722 tccctgcc    8

<210> SEQ ID NO 723
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723 ctgcttcc    8

<210> SEQ ID NO 724
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724 tgcag                                                                                5

<210> SEQ ID NO 725
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
tttggaaagg gggtgggggg agttt                                                         25

<210> SEQ ID NO 726
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726 ctaatctt                                                                             8

<210> SEQ ID NO 727
<211> LENGTH: 58
<212> TYPE: DNA
<213> ORGANISM: Homo sapiens

<400> SEQUENCE: 727
gccggcccct cagcttccct ccaccccgcg tggggggggg ggggtgctca gagctgca        58

<210> SEQ ID NO 728
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
gccggcccct cagctcagag ctgca                                                         25

<210> SEQ ID NO 729
<211> LENGTH: 58
<212> TYPE: DNA
<213> ORGANISM: Homo sapiens

<400> SEQUENCE: 729
ctatggccgg cccctcagct tccctccacc ccgcctccgg tcagcccag gcactgca        58

<210> SEQ ID NO 730
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
ctatggccgg cccctcagct tccctccacc ccgcacctcc ggtcagcccc aggcactg        58

<210> SEQ ID NO 731
<211> LENGTH: 43

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
ctatggccgg cccctcagcc tccggtcagc cccaggcact gca                     43

<210> SEQ ID NO 732
<211> LENGTH: 58
<212> TYPE: DNA
<213> ORGANISM: Homo sapiens

<400> SEQUENCE: 732
cttcctggat gctctcccgg atgtgggggg ggggggtgc tcagagctgc aggagcct      58

<210> SEQ ID NO 733
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733 aggc                                                                 4

<210> SEQ ID NO 734
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
ttttgagcct aagtcg                                                   16

<210> SEQ ID NO 735
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
acctcctctg c                                                        11

<210> SEQ ID NO 736
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
tcagagctgc aggagcct                                                 18

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 737 gtgggggag tttgctcctg g           21

<210> SEQ ID NO 738
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
gagtgagtgt gtgcgtgtgg            20

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
gtccgagcag aagaagaagg g          21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
gtggagggag cttgctcctg g          21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741 gtgggggag tttgctcctg g           21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
atggagggag tttgctcctg g          21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 743
gtggggggag tttgccccag g                                              21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744 gtgggggtg tttgctcccg g                                               21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
ggggagggag tttgctcctg g                                              21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
gggggggcag tttgctcctg g                                              21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
gtgtggggaa tttgctccag g                                              21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
gtgggtggag tttgctacag g                                              21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 749 ggtggggag cttgctccag g                                              21

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
gagtgagtgt gtgcgtgtgg                                               20

<210> SEQ ID NO 751
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
gagtgagtgt gtgtgtgggg                                               20

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
gagtgagtgt atgcgtgtgg                                               20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
gtgtgagtgt gtgcgtgagg                                               20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
gagtgagtgt gtgcatgagg                                               20

<210> SEQ ID NO 755
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
```
gagtgagtgt gtgtgtgtgg                                                    20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
gagtgaatgt gtgcgtgagg                                                    20

<210> SEQ ID NO 757
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
gggtgagtgt gtgcgtgagg                                                    20

<210> SEQ ID NO 758
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
gtgtgagtgt gtgcgtgggg                                                    20

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
gagtgagtgt gtgtgtgtgg                                                    20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
gagtgagtgt gtgtgtggtg                                                    20

<210> SEQ ID NO 761
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761

-continued gagtgagtgt gtgcgtgtga                                        20

<210> SEQ ID NO 762
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
gagtgagtgt gtgcgcgggg                                        20

<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
gagtgagagt gagcgtgagg                                        20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
gggtgagggt gtgcgggtga                                        20

<210> SEQ ID NO 765
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
atgtgagtgt gtatgtgtgg                                        20

<210> SEQ ID NO 766
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
gtccgagcag aagaagaagg g                                      21

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
gtctgagcag aagaagaatg g                                      21

```
<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
atccaagcag aagaagaaga g                                              21

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
ctccaagcag aagaagaaga g                                              21
```